(12) United States Patent  (10) Patent No.: US 8,685,304 B2
Arora et al.  (45) Date of Patent: Apr. 1, 2014

(54) PROCESS FOR MANUFACTURING IMPROVED DISPENSING DEVICES

(75) Inventors: Nevin Arora, Princeton, NJ (US); Christopher King, Montvale, NJ (US); Robert Zhong Lu, Montvale, NJ (US); Tri Nguyen, Succasunna, NJ (US); Dana Phieff, Bethlehem, PA (US); Steven Wu, Montvale, NJ (US)

(73) Assignee: Reckitt Benckiser LLC, Parsippany, NJ (US)

( * ) Notice: Subject to any disclaimer, the term of this patent is extended or adjusted under 35 U.S.C. 154(b) by 0 days.

(21) Appl. No.: 13/430,962

(22) Filed: Mar. 27, 2012

(65) Prior Publication Data

US 2012/0228800 A1  Sep. 13, 2012

Related U.S. Application Data

(62) Division of application No. 11/911,406, filed as application No. PCT/GB2007/001008 on Mar. 21, 2007.

(60) Provisional application No. 60/784,686, filed on Mar. 11, 2006.

(51) Int. Cl.
  *B29B 13/00* (2006.01)
(52) U.S. Cl.
  USPC .............................. 264/271.1; 4/231; 510/191
(58) Field of Classification Search
  USPC ............ 4/231; 510/191, 192, 193; 264/271.1, 264/177.17
  See application file for complete search history.

(56) References Cited

U.S. PATENT DOCUMENTS

| | | | |
|---|---|---|---|
| 104,077 | A | 6/1870 | Strausbourgh, Jr. |
| 849,978 | A | 4/1907 | Cox |
| 886,791 | A | 5/1908 | Gaines |
| 1,974,955 | A | 9/1930 | Foltis |
| 1,815,197 | A | 7/1931 | Gamel et al. |
| 2,011,732 | A | 8/1935 | Saeks |
| 2,984,841 | A | 5/1961 | Wilson |
| 2,985,377 | A | 5/1961 | Saeks |
| 3,088,126 | A | 5/1963 | Klingler |
| 3,217,338 | A | 11/1965 | Wilson |
| 3,290,699 | A | 12/1966 | Weinstein |
| 3,604,021 | A | 9/1971 | Nolte, Jr. |
| 3,668,717 | A * | 6/1972 | Curran .............................. 4/231 |
| 3,675,254 | A | 7/1972 | Brownstein |

(Continued)

FOREIGN PATENT DOCUMENTS

| | | |
|---|---|---|
| AT | 293965 B | 11/1971 |
| CH | 675140 A5 | 8/1990 |

(Continued)

OTHER PUBLICATIONS

English Language abstract XP002452702 of CN1702240 taken from esp@cenet.

(Continued)

*Primary Examiner* — Galen Hauth
(74) *Attorney, Agent, or Firm* — Norris McLaughlin & Marcus PA

(57) ABSTRACT

The present invention relates to a method for the manufacture of a lavatory dispensing device useful for the delivery of at least one treatment composition, preferably a cleaning composition and/or a sanitizing composition to a sanitary appliance.

24 Claims, 18 Drawing Sheets

(56) References Cited

U.S. PATENT DOCUMENTS

| | | | |
|---|---|---|---|
| 3,694,354 A | 9/1972 | Nolte, Jr. | |
| 3,943,243 A | 3/1976 | Kook | |
| 3,947,901 A | 4/1976 | Willert | |
| 4,067,946 A * | 1/1978 | Rickert | 264/150 |
| 4,320,033 A | 3/1982 | Yoshikawa | |
| 4,460,490 A * | 7/1984 | Barford et al. | 510/192 |
| 4,587,069 A * | 5/1986 | Meloy | 264/102 |
| 4,670,916 A | 6/1987 | Bloom | |
| 5,206,959 A | 5/1993 | Provenzano | |
| 5,449,473 A | 9/1995 | Bunczk et al. | |
| 5,698,513 A | 12/1997 | Schulz | |
| 5,987,655 A * | 11/1999 | Smet | 4/225.1 |
| 6,230,334 B1 | 5/2001 | Camp et al. | |
| 6,517,761 B2 | 2/2003 | Yoshida et al. | |
| 6,544,537 B1 | 4/2003 | Mahaffey et al. | |
| 6,651,261 B1 | 11/2003 | Leonard et al. | |
| 6,654,971 B1 | 12/2003 | Middleton | |
| 7,056,873 B1 | 6/2006 | Sidgwick et al. | |
| 2002/0035049 A1 | 3/2002 | Suri et al. | |
| 2006/0230576 A1 | 10/2006 | Meine | |
| 2006/0246149 A1 | 11/2006 | Buchholz et al. | |
| 2007/0039088 A1 | 2/2007 | Nguyen et al. | |
| 2007/0092477 A1 | 4/2007 | Cheung et al. | |
| 2007/0204389 A1 | 9/2007 | Graefe et al. | |
| 2009/0119825 A1 | 5/2009 | Wilson et al. | |
| 2009/0235443 A1 | 9/2009 | Arora et al. | |

FOREIGN PATENT DOCUMENTS

| | | |
|---|---|---|
| CN | 1702240 A | 11/2005 |
| CN | 1813111 A | 8/2006 |
| DE | 8906140 U1 | 11/1989 |
| EP | 0023059 A1 | 1/1981 |
| EP | 0879877 A1 | 11/1998 |
| EP | 1046755 B1 | 10/2000 |
| EP | 1048687 A | 11/2000 |
| EP | 1418225 A1 | 5/2004 |
| GB | 460041 A | 1/1937 |
| GB | 813392 A | 5/1959 |
| GB | 2287712 A | 9/1995 |
| GB | 2322632 A | 9/1998 |
| GB | 2338496 A | 12/1999 |
| GB | 2369377 A | 5/2002 |
| GB | 2407825 A | 5/2005 |
| GB | 2416784 A | 2/2006 |
| JP | 2003-002733 A | 1/2003 |
| WO | 9316242 A1 | 8/1993 |
| WO | 9940169 A | 8/1999 |
| WO | 9940169 A1 | 8/1999 |
| WO | 2005052110 A1 | 6/2005 |
| WO | 2006013318 A1 | 2/2006 |
| WO | 2007107750 A1 | 9/2007 |
| WO | 2007107755 A1 | 9/2007 |
| WO | 2007107769 A1 | 9/2007 |
| WO | 2007148054 A1 | 12/2007 |

OTHER PUBLICATIONS

English language abstract for EP1418225 which published May 12, 2004.

English language abstract for JP2003002733 which published Jan. 8, 2003.

English language abstract for EP0879877 which published Nov. 25, 1998.

* cited by examiner

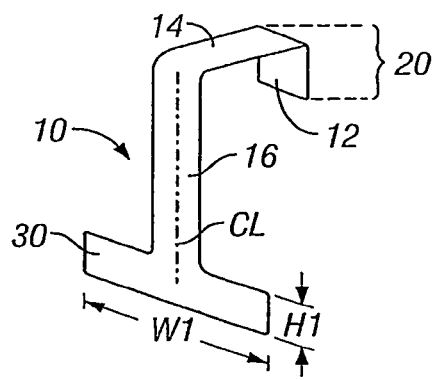
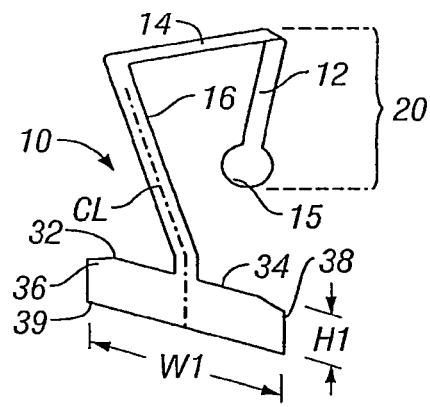
FIG. 1     FIG. 3
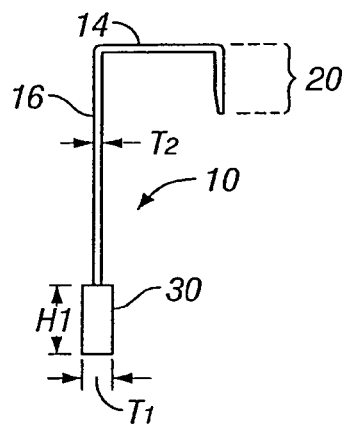
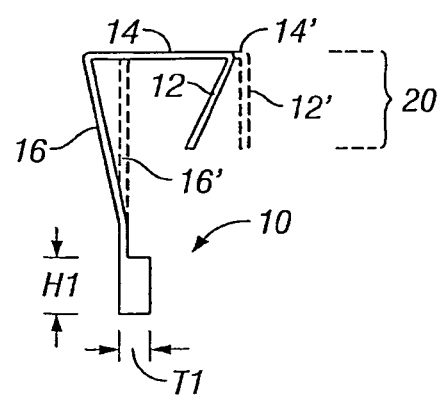
FIG. 2     FIG. 4

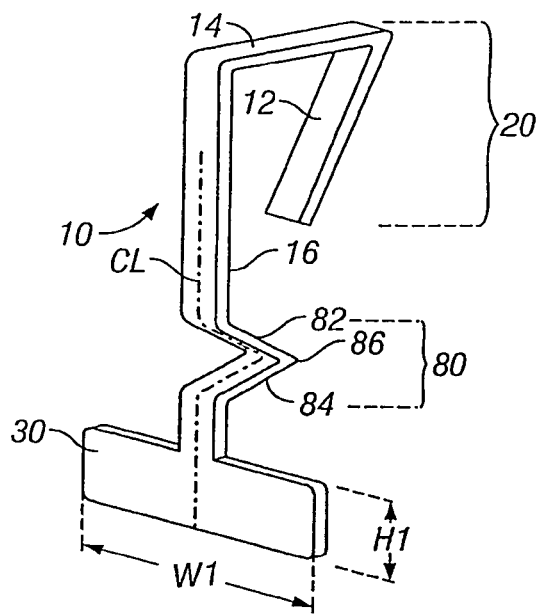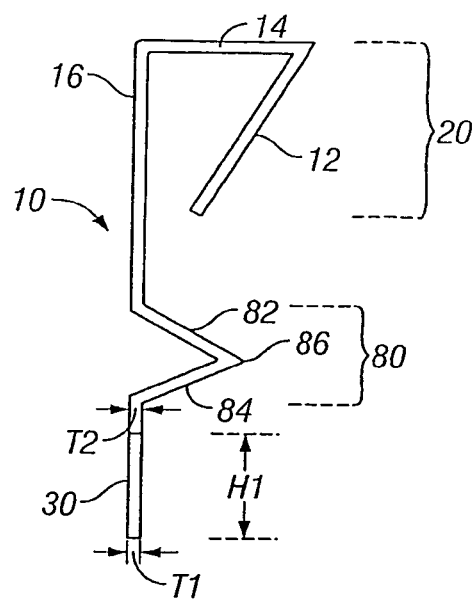
*FIG. 9A*  *FIG. 9B*
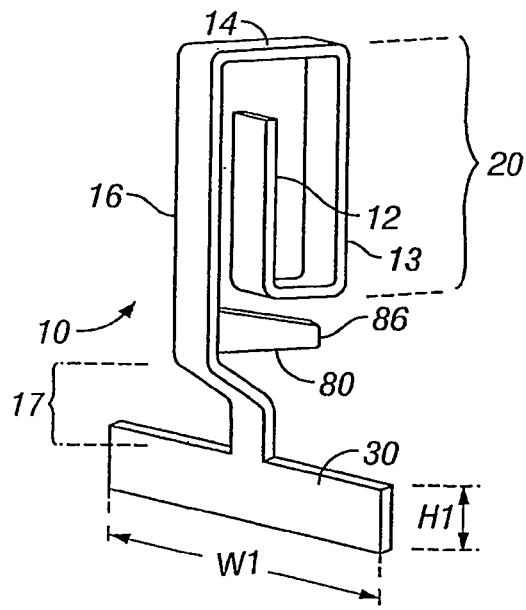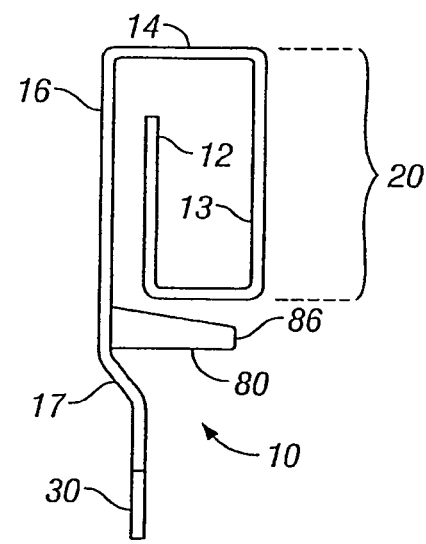
*FIG. 10A*  *FIG. 10B*

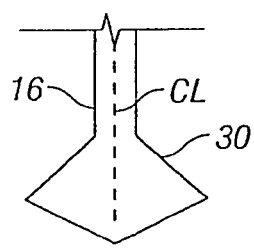
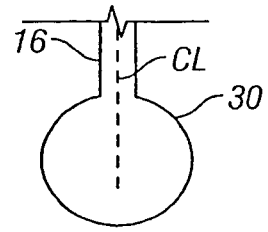
FIG. 13A  FIG. 13B
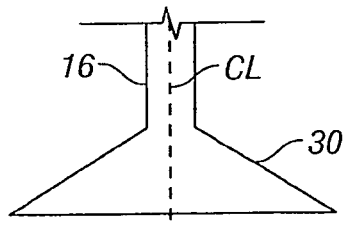
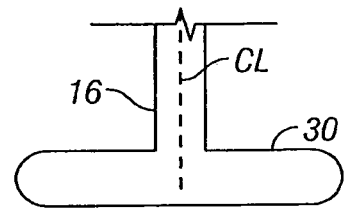
FIG. 13C  FIG. 13D
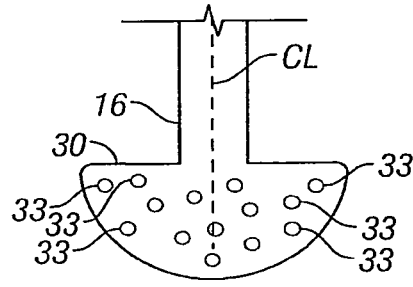
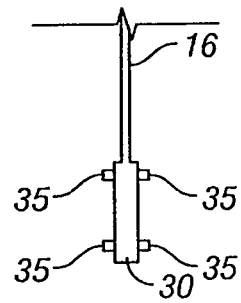
FIG. 14  FIG. 15B
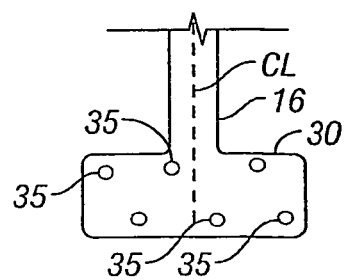
FIG. 15A

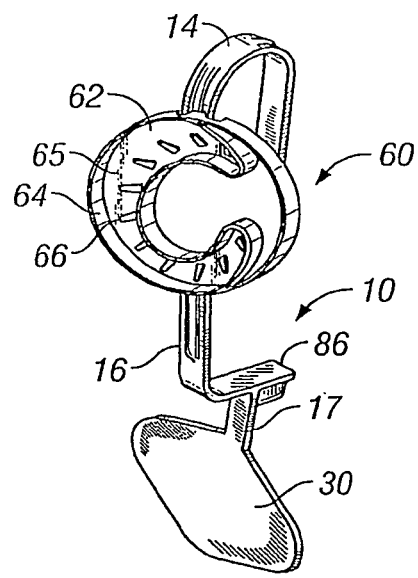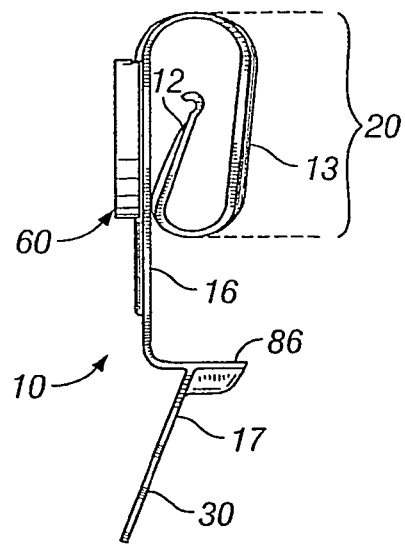
FIG. 16A                FIG. 16B
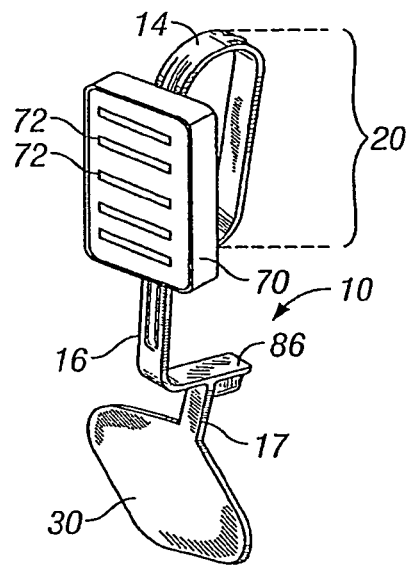
FIG. 17

PROCESS FOR MANUFACTURING IMPROVED DISPENSING DEVICES

This is a divisional patent application of U.S. Ser. No. 11/911,406, filed Oct. 12, 2007, which in turn is an application filed under 35 USC 371 of PCT/GB2007/001008.

The present invention relates to improvements in manufacture of dispensing devices. More particularly the present invention relates to improved processes for the manufacture of a device used to deliver a treatment composition to a sanitary appliance, particularly to a toilet, which treatment composition contains one or more chemical constituents e.g., coloring agents, cleaning agents, disinfecting agents, anti-lime scale agents in the form of a block. The treatment composition is formed by water contacting the block of the device coming into contact with the one or more chemical constituents; the block provides for the long term release of the one or more active agents during sequential contacts with water contacting the block of the toilet dispensing device.

Since the advent of sanitary appliances and in particular modern flush toilets, there has been a continuing need in the art to provide effective ways to maintain these appliances in a satisfactory condition between uses. The art is replete with devices which are intended to be used as "in the bowl" (or ITB) or "in the cistern" (or ITC) in order to provide a coloring and/or cleaning and/or fragrancing and/or sanitizing effect to such sanitary devices, particularly toilet bowls.

One common approach known to the art is to provide a device which is at least immersed within the cistern or tank of a toilet, which may be either placed wholly within the interior of the toilet such as by placement at the bottom of a toilet tank so that the entire device is wholly immersed in water when the tank is full, or is at least partially immersed within the water present in a toilet tank, such as wherein such a device is suspended from a part of the toilet tank, such as a lip or rim of the tank. Such are generally referred to as ITC devices.

A further common approach known to the art is to provide a device which is suspended from the rim of the toilet bowl and which is placed at or near the interior sidewall of the toilet bowl. Such are generally referred to as ITB devices. Such a device is designed to typically dispense a treatment composition to the interior of a toilet when a gel or block compositions is contacted with flushing water, or alternately, dispensing a fragrancing composition to the toilet bowl which is intended to counteract or mask malodors. Typically such devices include a hanger portion which is used to suspend a cage portion from the rim of the toilet bowl, such that the cage portion is positioned within the path of flowing water which is dispensed with each flush operation of the toilet. The cage portion typically comprises a plurality of holes or apertures which permit for the flush water to both enter and to exit the cage portion of the device. Typically a solid block composition or a gel composition is present within the cage. The solid block composition and/or gel composition typically comprises one or more cleaning constituents, e.g., one or more surfactants which provide a good cleaning and/or foaming benefit. Often the solid block composition and/or gel composition comprises a fragrance constituent as well which is provided to provide some degree of malodor suppression. For most such devices, the use of a cage is essential as in the case of a gel compositions, as gels are not self supporting and would not be useful without the physical supporting structure provided by the cage. With regard to solid block compositions, such compositions are notoriously prone to weakening and softening over time and most are known to sell or sag over their lifetime, particularly when approaching the end of their useful service life. The cage acts then as a porous receptacle and support for said blocks which would otherwise prematurely soften or disintegrate and fall into the toilet bowl and be flushed away before their composition is substantially consumed.

While the use of a cage is beneficial, the use of a cage is not without attendant problems. The use of a cage requires increased material costs, and additional manufacturing steps. Further as such ITB devices are typically single use type devices, once the gel or block composition is consumed or otherwise exhausted, the consumer discards the entire ITB device which is wasteful and contributes to the problems associated with proper garbage disposal. With regard to costs, in most conventional rim suspended lavatory devices comprising a hanger portion and a cage portion, the bulk of the material is typically used to form the cage. As such cages are typically fabricated from a synthetic polymer, such requires specific molding operations in order to form the rim suspended lavatory device, and to fill the cage with the solid block composition and/or gel composition prior to use and or sale.

Known to the art are rim suspended lavatory devices which are lavatory blocks of paradichlorobenzene which provide no cleaning benefit, but provide only a fragrancing benefit. Such blocks typically erode per sublimation of the paradichlorobenzene and/or by contact with flush water. Such rim suspended are lavatory blocks of paradichlorobenzene are typically packaged as a solid block or cake having extending from one side a loop of bendable wire. A portion of the bendable wire is embedded within the paradichlorobenzene block. The consumer is required to form the wire into a hanger appropriate to the particular geometry of their toilet so that the paradichlorobenzene block is positioned with the interior of the toilet bowl.

Apart from the foregoing, while the elimination of a cage from a conventional, rim suspended lavatory device would be beneficial such are not believed to be known. This is due to the fact that surfactant containing solid block compositions are known to soften quickly and this in turn eliminates any reasonable prospect of a useful service life when used in conjunction with a toilet absent the support provided by the cage.

Thus, while certain known-art dispensing devices provide beneficial malodor treatment effects, there is nonetheless a real and continuing need in the art to provide still further improved devices which can provide to a sanitary appliance a useful treatment benefit, preferably a useful cleaning benefit.

The present invention, in its various aspects, provides a method for the manufacture of a lavatory dispensing device useful for the delivery of at least one treatment composition, preferably a cleaning composition and/or a sanitizing composition to a sanitary appliance, e.g. a toilet bowl. The device can be used either as an ITC type device, or an ITB type device for a sanitary appliance such as a urinal, toilet tank or toilet bowl. In certain preferred embodiments the device according to the invention is used as an ITB type device. In certain alternate preferred embodiments the device according to the invention is used as an ITC type device.

According to a first aspect of the invention there is provided a method for the manufacture of a cageless lavatory device comprising a hanger and a compressed solid block comprising one or more chemical constituents for use with a sanitary appliance.

According to a second aspect of the invention there is provided a method for the manufacture of a cageless lavatory device comprising a hanger having a part adapted to be suspended from a part of a sanitary appliance, and a compressed solid block comprising one or more chemical constituents, wherein the device is adapted to be suspended within the interior of the toilet bowl.

In accordance with a third aspect of the invention there is provided a method for the manufacture of a cageless lavatory device comprising a hanger adapted to be suspended from the rim of a sanitary appliance, particularly a toilet bowl, and block comprising at least one or more chemical constituents adapted to be suspended within the interior of the toilet bowl, wherein the block composition is long lasting.

According to a fourth aspect of the invention there is provided a method for the delivering a treatment composition to a sanitary appliance, especially preferably, to the interior of a toilet bowl, which process comprises: providing a cageless lavatory device produced according to one or more of the improved methods described hereinafter, the device comprising a hanger adapted to be suspended from a part of a sanitary appliance, and a compressed block comprising at least one or more chemical constituents adapted to be suspended within the sanitary appliance, and, periodically flushing water about the exterior of the compressed block to elute at least one chemical constituent to form a treatment composition with said water which treatment composition is used to treat a part of the sanitary appliance.

According to a fifth aspect of the invention there is provided a cageless lavatory device comprising a hanger having a part thereof adapted to be suspended from a part of a sanitary appliance, particularly from a part a toilet cistern or toilet tank, and a compressed solid block comprising one or more chemical constituents, wherein the device is adapted to be suspended within the interior of said cistern or tank.

According to a sixth aspect of the invention there is provided a cageless lavatory device comprising a hanger having a part thereof adapted to be suspended from a part of a sanitary appliance, particularly from a part a toilet cistern or toilet tank, and a compressed solid block comprising one or more chemical constituents, wherein the device is adapted to be suspended within the interior of said cistern or tank.

In accordance with a seventh aspect of the invention there is provided a cageless lavatory device comprising a hanger adapted to be suspended from the rim of a sanitary appliance, particularly a part of a toilet cistern or toilet tank such as from a part of a rim of a toilet cistern or toilet tank comprising at one or more chemical constituents adapted to be suspended within the interior of said cistern or tank, wherein the block composition is long lasting.

In accordance with a still further aspect of the invention there is provided as a vendible article, a cageless lavatory device comprising a hanger and a compressed solid block comprising one or more chemical constituents for use with a sanitary appliance, particularly a toilet produced by one or more of the processes defined herein.

These and other aspects of the invention will be more evident from a reading of the following specification.

BRIEF DESCRIPTION OF THE DRAWINGS

FIG. 1 depicts an embodiment of a hanger of a cageless lavatory device.
FIG. 2 depicts a side view of a further embodiment of hanger.
FIG. 3 depicts a further embodiment of a hanger.
FIG. 4 depicts the hanger of FIG. 3 in alternate configurations.
FIGS. 9A and 9B depict two views of an embodiment of a hanger.
FIGS. 10A and 10B depict two views of a further embodiment of a hanger.
FIGS. 13A though 13D depict various embodiments of plates.
FIG. 14A depicts a further embodiment of a plate.
FIGS. 15A and 15B depicts a further embodiment of a plate.
FIGS. 16A and 16B illustrates a further embodiment of a hanger which includes an air treatment dispenser.
FIG. 17 depicts a further embodiment of a hanger which includes an air treatment dispenser.

Figure 5:
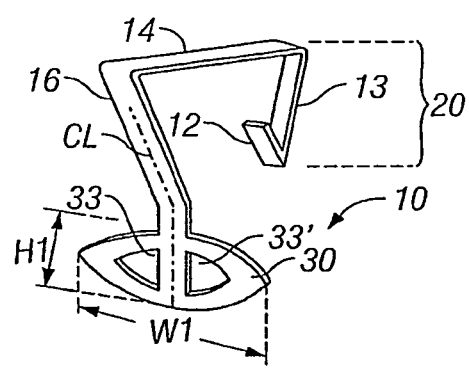
FIG. 5 depicts a further embodiment of a hanger.

Broadly defined, the present invention relates to a method of making a cageless lavatory device comprising a hanger and a compressed solid block comprising one or more chemical constituents for use with a sanitary appliance, as well as methods for its use of the cageless lavatory device in the treatment of sanitary appliances, particularly toilets.

The inventors have surprisingly found that notwithstanding the existing prejudice in the prior art which dictates the use of cages to support and contain lavatory treatment blocks, that it has been discovered by the inventors that it is now possible to fabricate cageless lavatory devices which comprise a hanger and a compressed solid block composition depending from the hanger which solid block compositions comprise one or more chemical constituents, preferably at least a surfactant composition, which cageless lavatory devices are useful in providing a treatment composition to a sanitary appliance over repeated flushes of water and/or repeated immersions in water wherein the compressed blocks to not fall away from or break away from the hanger for a reasonable duration of time. This result is unexpected as the prior art dictates the use of a cage as previously described, and as is also widely known in the art to support a lavatory block composition over its useful lifespan, particularly wherein the lavatory block comprises one or more surfactants. As is known to the art, with repeated flushes of water, many such surfactant containing lavatory blocks tend to swell and/or soften and very frequently disintegrate or slump, thus requiring a cage to contain the lavatory block. Alternately as is known in the art, with long term immersion in water such as in a toilet cistern or toilet tank, such surfactant containing lavatory blocks tend to swell and/or soften and very frequently disintegrate or slump, thus requiring a cage to contain the lavatory block.

The inventors have discovered that cageless lavatory devices which comprise a hanger and a compressed solid block composition depending from the hanger which solid block compositions include one or more chemical constituents, preferably at least a surfactant, may be formed by a process which contemplates: (a) forming a mass comprising at least one or more chemical constituents; (b) compressing a quantity of the mass to encase a portion of the hanger. A cage is not required to encase any part of the compressed solid block so formed which block encases a portion of the hanger. Optionally but preferably, the mass comprising the at least one or more chemical constituents is mixed and extruded into a preform shape, thereafter a portion of the hanger is inserted into the preform shape or between a plurality of preform shapes, and subsequently the perform shape(s) are compressed in a die to provide the final form of the compressed solid block composition of the cageless lavatory device. The compressed solid blocks are retained on a part of the hanger without the need of an enclosing cage, as well as without the need of any separate adhesive material or composition which is placed between the compressed solid block and the part of the hanger which the compressed solid block contacts.

In its simplest form the hanger is merely an article which comprises at one end, a hook end which is adapted to or configured to suspend the hanger from a part of a sanitary appliance. The hanger is preferably configured so to permit its use either as an ITB device or as an ITC device. The hanger also includes an element, preferably a plate, which is adapted to be embedded within the compressed solid block composition. While the hook end may be integrally formed and approximate to the plate, quite frequently the hanger includes an intermediate stalk connecting the hook end with the plate. The hanger itself may be a single element of a unitary construction, or alternately, may be formed from a plurality of elements which are adapted to be linked or connected together. When the hanger is formed from two or more such discrete elements, the individual elements can be affixed, attached, or linked together to ultimately form the hanger of the invention. The cageless lavatory dispensing device of the invention may be provided as a multiple-use article, wherein the consumer retains a part said device on the sanitary appliance, but replaces a part of the said device periodically as may be needed. In such a configuration, usually a part of the hanger is retained and reused by a consumer, but upon consumption of the compressed solid block, a new compressed solid block is provided to the sanitary appliance where it may be removably affixed to the retained part of the cageless lavatory dispensing device. Most conveniently however the hanger is a single piece article.

With regard to the hook end, it is to be understood that the hook end of the hanger can be of any configuration which is suitable to provide a hook-type support for suspending the plate and the compressed solid block within the interior of a sanitary appliance. Ideally, the hook is configured such that it is adapted to be suspended over at least a part of the rim of sanitary appliance. Such may be a rim of a urinal, a toilet bowl, or toilet cistern or tank. The hook may be of any suitable dimension, and as it is understood that as the configuration and geometry of sanitary appliances vary, naturally the hook can be adapted to suit the particular dimensional or geometric configurations of toilets. Alternately and preferably the hook end is flexible and configurable to adapt to various configurations and geometries so that it may be used with different sanitary appliances. Typically however, the hook end may be configured into a "U" shaped portion of the hanger such that it may be used to suspend the hanger and plate bearing the compressed solid block composition.

The hook may be provided in a rigid, preformed configuration which is non-flexible or only sparingly flexible in order to accommodate the dimensions of the hook to a particular sanitary appliance. For example wherein the hook is provided as a rigid, preformed configuration to be used in suspending the cageless lavatory dispensing device in an ITC application the hook may be a discrete element which is dimensioned to have a cross-section which in adapted to accommodate a part of the upper rim or edge of a toilet cistern or toilet tank. Such a hook may merely suspend the device on the rim, or the hook may be configured so that when applied to the part of the upper rim or edge of a toilet it functions as a mechanical clip such that it is generally retained at its point of installation and resists accidental misplacement or movement. Additionally or alternately such a hook may further include a connector element which may take any physical shape or form and which is configured to cooperatively connect with a the remaining element or elements of the cageless lavatory dispensing device so that said remaining element or elements may be removably affixed to such a hook. In such manner, the hook may be retained although the remaining elements, viz., the plate bearing the compressed block and/or the stalk may be replaced a number of times once the compressed block is exhausted. Any suitable mechanical or chemical fastener means may be used to provide such a function. By way of non-limiting example may be used any of a number of cooperating mechanical elements such as clips, hook-and-loop fasteners, pins, springs, elastic bands, loops, eyelets as well as chemical means including adhesives such as light or medium duty adhesives may be used as the fastener means. Other fastener means not elucidated herein but known to the art may also be used. In one preferred embodiment the hook includes a part which includes a mortise shaped element, which cooperates with the stalk or plate which is configured as a cooperating tenon which is removably insertable into the mortise shaped element. In another preferred embodiment the hook includes a peg or hook, and the stalk or plate includes a cooperating loop or eye from which the stalk and/or plate bearing the compressed block may be suspended. The use of such two-part embodiments of the inventive cageless lavatory block is in certain embodiments of the invention preferred as such provide a great deal of flexibility and also permits for the reuse of at least one element of the cageless lavatory dispensing device multiple times without requiring replacement of the complete cageless lavatory dispensing device when a compressed lavatory block is exhausted. Thus is certain embodiments, certain elements of the cageless lavatory dispensing device may be reused, while others are intended to be single-use elements.

Conveniently however, the hook end is provided as one or more articulated elements which can be flexed or bent from a first or a "folded" configuration to a second or "open hook" configuration. It is to be understood that according to preferred embodiments, in order to minimize the volume of the hanger and in particular the hook end thereof, the hanger may be provided in a collapsed or folded configuration when placed into a package. Upon opening of the package, the consumer is then expected to easily unfold, extend, or otherwise stretch a portion of the hanger in order to form the hook end. A further important advantage is that the degree of flexibility provided into the hanger in order to provide for such a foldable and unfoldable hook end also introduces a degree of tension when the hook end is configured to be hung upon a sanitary appliance, and in particular the rim of a urinal, a toilet tank or cistern, or the rim of a toilet bowl. In such a configuration, the tension actually aids in the gripping of the hook upon the portion of the sanitary appliance upon which it is originally positioned by the consumer. Such tension reduces the likelihood of lateral movement or translation from its initial placement by a consumer unless desired by the consumer. Thus, specific placement of the cageless lavatory dispensing device, and a reasonable expectation that it will be retained at or near the position in which it was originally installed by a consumer relative upon a sanitary appliance is provided. Furthermore, the tension provided also provides for a degree of resiliency and also aids in the positioning of the compressed solid block at, or near, a specific part of the sloping interior wall of a sanitary appliance, e.g., a toilet bowl. Such can be beneficially particularly due to the fact that flush water from the toilet bowl typically exits from beneath the rim. Utilizing the tensile property of the hanger, the continuous positioning of the compressed solid block within the path of the flowing flush water is assured under most circumstances.

As has been noted above, in certain preferred embodiments and indeed, according to most preferred embodiments a stalk exists to connect the plate with the hook end of the hanger. The stalk itself may be of any dimension or length, however when used in an embodiment of the invention wherein the device is an ITC type device, desirably the stalk is of sufficient length to ensure that the compressed block will be at least partially immersed, but preferably wholly immersed, in the water present in the toilet tank or cistern between flushes. When the stalk is used in an ITB type device, advantageously once the hook end is suspended upon a sanitary appliance, particularly the rim of a toilet bowl, the stalk extends a sufficient length to the plate such that ultimately, the positioning of the hook and the length of the stalk as such that the compressed solid block enrobing the plate is positioned in the path of the flush water. Again, the dimensions and in particular the length of the stalk can be varied in order to meet the specific requirements of a specific configuration of a sanitary appliance, particularly in the case of a toilet bowl, the distance from the top of the rim downwardly into the interior of the toilet bowl, or in the case of a cistern or tank, the distance from the top of the rim of the tank or cistern downwardly such that the plate intersects or is beneath the waterline of the water present in the tank or cistern between flushes. For example, when used as an ITB device, in toilets typically found in use in North America, the interior sloping walls of the toilet bowl are typically of a smaller and a more circular radius, thereby providing a "shallower" distance between the top of the rim of the toilet bowl, and the sump or water outlet at the bottom of the toilet bowl. In such a circumstance, a shorter stalk length is typically adequate in order to ensure that the compressed solid block is placed within the path of the flush water. In European toilets, typically, the configuration of the toilet bowl and its sloping walls are usually in the form of a more frusto-conical configuration, thus providing a "deeper" toilet bowl as measured from the rim to the top level of the water in the sump. In such configuration, frequently, a longer stalk length then would be required for a North American toilet is typically preferred. Of course, different configurations of other toilet bowls are contemplated as well.

The hanger is used to support the compressed solid block composition, and accordingly part of the hanger is adapted to be embedded and/or enrobed within the compressed solid block composition. While the compressed solid block composition may depend from any part of the hanger, preferably the compressed solid block composition encases a part of the hanger other than the hook end thereof, and advantageously encases a part of the stalk, preferably a part of the stalk which is distal to the hook end of the hanger.

The hanger of the invention desirably necessarily includes a plate which is adapted to be embedded and/or enrobed within the compressed solid block composition. The plate itself is at the end distal to the hook end of the hanger and typically is integrally formed with the stalk, or where a stalk is not provided, with the hook end of the hanger. The plate itself may be essentially of any useful configuration, but desirably, the plate is dimensioned such that it is completely encased by the compressed solid block composition. Conveniently, the plate has a geometry which is symmetrical about the longitudinal center line or axis of the stalk and/or hook and depends directly from the stalk where present, or from the end of the hook end of the hanger. Conveniently, the plate is generally of a flat, planar configuration, and has a uniform thickness across its surface. However, it is also contemplated that the plate may include regions of diminishing thickness i.e. such as tapered sections or margins at or near the boundaries of the plate.

The plate itself need not necessarily be limited to a generally planar, and generally two-dimensional configuration, but may include elements or sections which extend outwardly from the top and/or bottom surfaces of the plate, such as in the form of one or more pegs, studs, pins, fins, rods, loops or the like which might be useful in providing further physical support between the plate, and the compressed solid block composition enrobing it. Alternately, the plate may include one or more perforations passing therethrough whereby, upon compression adjacent portions of the solid block composition meet and pass through one or more perforations which may be provided within the plate.

The plate itself may be of any configuration and when in a planar form can be square, rectangular, triangular, polygonal, ellipsoid, circular, oblate, or for that matter any configuration which may be embedded within the interior of the compressed solid block. Alternately, the plate can may be one or more elements such as rods or tubes, which depend from and extend outwardly from the stalk. While the thickness of the plate may vary, preferably it is between 0.05-3 mm thick, preferably between 0.1 and 2 mm thick, and most preferably between 0.25 and 1.5 mm thick. The thickness of the plate may vary across its surface, and in certain embodiments the thickness of the plate decreases across its dimensions with the thickest portion of the plate being near its geometric center, and the thinnest parts of the plate being one or more of the margins or peripheral sections of the plate. Such may be used to form a plate of tapering dimensions. Preferably however the plate is of generally uniform in thickness with at least 90%, preferably at least 95% of its surface being of a constant thickness with a variance of not more than +/−5%.

Alternately the plate can be of a configuration other than a planar configuration, e.g., the plate may be one or more elements such as rods or tubes, which depend from and extend outwardly from the stalk. Still alternately a separate plate may be omitted and the compressed solid block composition merely encasing or enrobing a part of the hanger, especially a part of the stalk.

Optionally but in certain embodiments necessarily, the hanger of the invention also includes a standoff element. The standoff element may conveniently be a formed section of the hanger or stalk such that the standoff element is an integral part thereof. Alternately the standoff element may be a discrete element or discrete part of the hanger, preferably a part of the stalk when present in a hanger according to the invention. The standoff element may be provided preassembled or pre-affixed to the stalk or may require that such be attached by a user or consumer. The hanger standoff element may be positioned or located anywhere on the hanger, but is preferably located between the hook and the compressed treatment block. Advantageously the hanger standoff element is positioned or located such that with respect to the total length of the hanger as measured from the end of the hook end, to the distal end of the hanger, the standoff element is within the lower half of this length. Preferably the standoff element is within the lower 40% of the distance, more preferably is within the lower 33% of this distance. In particularly preferred embodiments the standoff element is at a position proximate to or adjacent to the compressed solid block encasing or enrobing a part of the hanger, or at a position proximate to or adjacent the plate.

When a hanger is provided with a plate, the inventors have unexpectedly observed that the preferred configuration of the plate is a generally planar plate which has sloping top edges which are angled downwardly and form an obtuse angle with the center line (or center-axis) of the stalk or hook of the hanger, as measured from the points from which the edges of plate intersect the stalk or hook end. The downwardly sloping edges may be linear or straight-edged, or arcuate. The inventors have found that downwardly sloping edges are advantageous in resisting pooling of water, and permit for the runoff of water during the service life of the cageless lavatory dispensing devices when the compressed solid blocks may have sufficiently eroded to expose part of the plate from within the interior of the said blocks. Surprisingly, the inventors have found that the best configuration for the plate is indeed a generally planar plate having a generally uniform thickness across its surface. The dimensions of the plate should be such that when considering the cross-sectional area of the plate with that of the cross-sectional laminar layer of the block within which it is positioned, the percent coverage of the plate area to the laminar compressed solid block area should be not more than about 90%, more preferably the ratio is between about 10% and 90%, more preferably between about 20% and 80% of the surface area of the laminar layer or plane of the compressed solid block composition within which the plate lies.

The inventors have also surprisingly found that while many plate configurations are possible, the longest service life of the cageless lavatory dispensing devices were observed with generally planar plates which were substantially embedded and enrobed within the interior of the compressed solid block composition. The compressed solid blocks do not require the use of an adhesive substance or material intermediate the plate and the compressed solid block in order to retain the compressed solid block on the faces of the plate. While not wishing to be bound by the following, it was theorized that when used as an ITB type device, during repeated flushes of water coming into contact with the upper surface of the compressed solid block, viz, the region from which the stalk or hook end extends, minimal cracking or delamination of the regions of the block which had been joined together by the compression of the solid block was observed. This reduction of delamination or otherwise observed as splitting of the block in this region ensured the longer term retention of the compressed solid block composition upon the plate, and thereby the improved duration of the service life of the cageless lavatory dispensing device used in conjunction with the sanitary appliance. Surprisingly, it was observed that when perforations, including large diameter circles or other discontinuities were present passing through the plate, the compressed solid blocks mounted upon the plates were observed to often prematurely fail. Again, and while I am not wishing to be bound by the following theory, it is believed that the formation of miniscule channels in the region of the compressed solid block which had been laminated may have formed during repeated flush cycles, and these channels passing into the interior of the block formed cavities and/or otherwise soften the interior of the compressed solid block in the region of such discontinuities in the plate, thereby mechanically softening the block and weakening its hold upon the plate. Similarly, it is also observed that when the plate had a more three-dimensional shape, that is to say included elements such as studs, or pins extending outwardly from one or more faces of the plate, that again, premature failure of the compressed solid block compositions was observed. Again, it is believed that a similar phenomenon also occurred, namely in the formation of microchannels in the region of the lamination of portions of the block were formed, and provided for the flow of flush water into the interior of the block and to the region of the plate and particularly to the regions surrounding the extended studs or pins. Again, this was believed to be responsible for premature softening of the interior of the compressed solid block, and its premature failure.

Thus, in particularly preferred embodiments, the plate configuration is absent any perforations, as well as being absent of any elements or protrusions extending outwardly from one or more faces of the plate.

Referring again to the standoff element, in embodiments of the hanger which comprise a standoff element, the standoff element is suitably dimensioned such that it is adapted to extend from the stalk or other part of the hanger in a direction rearwardly of the stalk, that is to say, in the direction which is coincident with the direction of the hook end relative to the stalk. Thus, when the cageless lavatory device is mounted on the rim of a toilet bowl or on the rim of a toilet cistern or toilet tank, the standoff element extends in generally the same direction as the hook end. Desirably this direction is also generally perpendicular, viz., 90°, +/−15°) relative to the plane defined by the plate, where such a plate is also present as part of the hanger. The standoff element has a height dimension at which is forms a peak point which is the maximum distance from which it extends from the hanger, preferably the stalk. Desirably the height of the standoff element is such that when the cageless lavatory dispensing device is initially installed in a sanitary appliance, the height of the standoff element is sufficient to impede some physical contact between the compressed solid block and a sidewall or other part of a sanitary appliance adjacent to the said block, and/or when the said block is partially eroded due to dissolution or other cause the height of the standoff element is sufficiently great such that the peak point of the standoff element contacts the sidewall or other part of the sanitary appliance and acts to lift the compressed solid block such that a gap is formed between the said sidewall or other part and the solid block. In certain embodiments, such occurs when less than 50% of the total mass of the compressed solid lock, preferably when less than 65% of the compressed solid block is eroded or dissolved. The formation of such a gap, particularly prior to the substantial erosion of the compressed solid block is surprisingly advantageous from several technical perspectives. First, the formation of such a gap permits for the composition of the compressed solid block to be out of contact with a wet sidewall between flush cycles when the cageless lavatory device is used in a toilet bowl. Such improves the service life of the compressed solid block. Second, when the compressed solid block includes a surfactant constituent, and is spaced-apart from the sidewall of a toilet bowl, during the flush cycle improved foam formation is observed to occur. While not wishing to be bound by the following the inventors believe that the gap between the surface of the compressed solid block suspended on the hanger and the adjacent sidewall of the toilet bowl provides for some cavitation and air entrainment within this gap space during the flushing operation. Such is believed to improve the formation of bubbles and a more visible foam. Preferably the gap between the gap between the surface of the compressed solid block suspended on the hanger and the adjacent sidewall of the sanitary appliance should be in the range of from 0.1 mm-10 mm, preferably 0.1-7 mm, still more preferably 0.2-5 mm, and most preferably 0.2-3 mm at the closest point between the block surface and the adjacent sidewall.

While it is understood that various configurations and geometries of the compressed block compositions, as well as various configurations and geometries of the hanger and standoff element are possible, it is nonetheless preferred that the relative dimensions of these elements is such that when the cageless lavatory dispensing device which includes a standoff element is formed but has not been put into service, when the said device is laid upon a flat horizontal surface, the standoff element has a sufficient height such that the peak point is sufficient to raise at least a part of the rearward face of the compressed solid block from contacting the horizontal surface. Preferably as well, after the lavatory dispensing device is put into service and installed in a sanitary appliance, preferably a toilet bowl and at least 50% of the mass is eroded, desirably the height of the standoff element is sufficient that the peak point contacts the surface of the sanitary appliance adjacent to the compressed solid block and is sufficient to cause a gap of at least 0.2 mm, preferably a gap of between 0.2 and 5 mm between the closest point between the block surface and the adjacent sidewall.

The hanger and where present, a standoff element, whether provided as a single unitary piece or assembled from a composite of discrete pieces or elements, may be formed from any of a variety of materials which can be used for the purpose described herein. Exemplary and preferred materials include metals including wires or rods which are bendable and are preferably coated with flexible non-metallic material such as a flexible polymer, a paint or a sheath, as well as one or more synthetic polymers which are preferred. Preferably the hanger may be formed of any of a number of thermosettable or thermoformable synthetic polymers such as are widely used in casting or injection molding. Exemplary synthetic polymers such as polyamides, polyolefins (e.g., polypropylene, polyethylene) as well as polyalkyleneterephalates (i.e., polyethylene terephthalate, polybutylene terephthalate), polystyrenes, polysulfones, polycarbonates as well as copolymers formed from monomers of one or more of the foregoing being several nonlimiting examples of useful synthetic polymers. Preferably the material of construction is at least somewhat flexible. As to the material of construction of the hanger, the only criteria being that the selected materials used to fabricate the hanger is not deleteriously affected by the chemical constituents of the compressed solid block composition with which part of the hanger, viz., the plate and possibly part of the stalk, contacts.

The dispensing devices according to the invention may optionally include an air treatment dispenser which may be an article or element which forms part of the dispensing device of the present invention. The air treatment dispenser may be affixed to or form part of the hanger and provides for the release of a fragrance or other air treatment composition to the ambient environment of a toilet or other lavatory appliance, e.g. a lavatory or bathroom. The fragrance may be any composition which is known to the art to provide a perceptible fragrancing benefit, any may be based on naturally occurring materials such as one or more essential oils, or may be based on synthetically produced compounds as well. Examples of essential oils include pine oil, Anetlhole 20/21 natural, Aniseed oil china star, Aniseed oil globe brand, Balsam (Perui), Basil oil (India), Black pepper oil, Black pepper oleoresin 40/20, Bois de Rose (Brazil) FOB, Bomneol Flakes (China), Camphor oil, White, Camphor powder synthetic technical, Canaga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Counmarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), and Wintergreen oil.

Many of these essential function as a fragrance agent, which fragrance agent which may be a substance or mixture of various substances including those which are naturally derived (i.e., obtained by extraction of flower, herb, blossom or plant), those which are artificially derived or produced (i.e., mixture of natural oils and/or oil constituents), and those which are synthetically produced substances (odiferous substances). Generally fragrance agents are complex mixtures or blends various organic compounds including, but not limited to, certain alcohols, aldehydes, ethers, alamatic compounds and varying amounts of essential oils such as from about 0 to about 25% by weight, usually from about 0.05 to about 12% by weight, the essential oils themselves being volatile odiferous compounds and also functioning to aid in the dissolution of the other components of the fragrance agent. In the present invention, the precise composition of the fragrance agent desirably emanates a pleasing fragrance, but the nature of the fragrance agent is not critical to the success of the invention.

In addition to a fragrance or in place thereof, the air treatment dispensers may be used to deliver one or more further compositions or constituent which provide a further or different air treatment benefit. Such may be any other material which is useful in providing treatment of ambient air, such as a sanitizing agents. e.g., one or more glycols or alcohols, or materials which are intended to counteract, neutralize, or mask odors in the absence of, or in conjunction with, the fragrance composition of the present invention. Alternatively, the air treatment constituent may be one or more materials which provide and effective insecticide repelling or insecticidal benefit; such would be particularly useful in climates or environments where insects present a nuisance or health hazard According to certain preferred embodiments of the invention, the fragrance composition or other air treatment composition is associated solely with the air treatment dispenser of the invention. In this preferred that such an air treatment dispenser containing a fragrance composition or other air treatment composition be positioned with respect to a sanitary appliance, particularly a toilet bowl, such that the air treatment dispenser does not come into contact with water during the useful life of the device. This provides several simultaneous benefits including, the longevity of the fragrance composition, the improved delivery characteristic of the fragrance composition which does not become submerged or diluted with water associated with the sanitary appliance, as well as the fact that a much broader range of fragrance compositions (or other air treatment compositions as noted above) can be utilized as, there is no concern regarding the compatibility of fragrance with the materials in the compressed solid block composition. Furthermore, the utilization of the fragrance composition solely in conjunction with the air treatment dispenser also provides a constant release of the fragrance composition to the ambient environment of the sanitary appliance even when the sanitary appliance is not being the used. In the case where pleasant fragrance and/or odor masking composition is provided in the fragrance composition, a beneficial consumer perception of the use of the products can be realized. Alternately, where a sanitizing agent and/or an insecticidal agent is utilized as all or part of the fragrance composition of the air treatment dispenser, the continual benefits of continuous release of such agency may be provided. Advantageously the air treatment dispenser may be affixed to or form part of the hanger, preferably either on part of the stalk such that the air treatment dispenser faces the interior of the toilet bowl or other sanitary appliance or alternately the air treatment dispenser may be affixed to or form part of the hook end, preferably on a part thereof such that the air treatment dispenser is positioned on the exterior of the toilet bowl or other sanitary appliance. Alternately the air treatment dispenser may be an article which is removable from the hook end, such as wherein the hook end includes a fastener component and the air treatment dispenser includes a complimentary fastener component which provides means to affix the air treatment dispenser to the hanger. By way of non-limiting example, fastener components include, but are not limited to: hook-and-loop type fasteners (VELCRO®), clips, pins, snaps, adhesive strips, screw type fasteners as well as hook and eye type fasteners which may provide for removal of an replacement of the air treatment dispenser. By way of non-limiting example fastener components providing a permanent connection between the air treatment dispenser and the hanger include adhesives, spot welds, pins, rivets, screw-type fasteners and of course the air treatment dispenser may be integrally formed as part of the hanger.

The form of the fragrance composition or other air treatment composition provided in the air treatment dispenser can take any form including, liquid, solid, or gel form. Advantageously fragrance composition or other air treatment composition is provided as one or more of: a gel contained in a cavity, such as part of the air treatment dispenser or a removeable tray; a bottle or vessel which comprises a wick having one end extending into its interior which contains a quantity of the fragrance composition or other air treatment composition and the other end of said wick being exposed to the exterior of the bottle or vessel and into the ambient environment of the toilet or lavatory appliance; a canister or container such as a pressurized aerosol container or a pump supplied with a non-pressurized vessel or container, said container containing a quantity of the fragrance composition or other air treatment composition which may be manually dispensed by a consumer to the ambient environment of the toilet or lavatory appliance; as well as a film, sheet or fibrous pad or other porous substrate which contains a quantity of a fragrance composition or other air treatment composition which volatilizes into the ambient environment of the toilet or lavatory appliance. Preferably however, the fragrance composition or other air treatment composition is a gel system which is then deposited in a chamber or cavity present in the air treatment dispenser. The gel system can be formed by a variety of components known to those of ordinary skill in the art. For example, it can be formed from absorbents, starch based systems, modified celluloses, natural gums and other materials which can form a gel when the fragrance composition, aforementioned gel components, and water or hydrophilic solvents are mixed together. According to certain particularly advantageous embodiments of the invention the fragrance composition is a gel system as it is described in U.S. Pat. No. 5,780,527, the contents of which are hereby incorporated by reference.

The lavatory dispensing devices according to the invention necessarily also comprise a compressed solid block comprising at least one or more chemical constituents such that when the block is immersed, rinsed or washed with water, said chemical constituents are eluted or dissolved into said water and forms a treatment composition which is useful in treating a sanitary appliance, and particularly a toilet tank or cistern or a toilet bowl. Such a treatment composition may provide a cleaning and/or sanitizing and/or disinfecting benefit to the toilet or other sanitary appliance being treated with the devices of the invention.

As chemical constituents the compressed solid block may include any known art cleaning agents or cleaning constituents known to those of ordinary skill in the relevant art, and without limitation include one or more detersive surfactants selected from anionic, cationic, nonionic as well as amphoteric or zwitterionic surfactants. Certain detersive surfactants may also provide a dual role in providing detergency as well as a disinfecting effect, viz, certain cationic surfactants, which are described hereinafter as a disinfecting agent. These one or more cleaning agents or cleaning constituents may be used with or without other constituents being present in the compressed solid blocks of the invention.

The solid block composition of the invention desirably comprises a surfactant constituent which may be one or more detersive surfactants. Exemplary useful surfactants include anionic, nonionic, cationic, amphoteric, and zwitterionic surfactants, particularly those whose melting points are sufficiently high, above about 110° F., preferably above 125° F., to permit processing according to known art techniques. However, small amounts of low melting point surfactants and even liquid surfactants may be used in providing the surfactant constituent.

Exemplary useful anionic surfactants which may be used in the compressed solid block composition of the invention can be broadly described as the water-soluble salts, particularly the alkali metal salts, of organic sulfuric acid reaction products having in their molecular structure an alkyl or alkaryl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic surfactants which can be employed in practiing the present invention are the sodium or potassium alkyl sulfates, especially those obtained by sulfating the higher alcohols ($C_8$-$C_{18}$ carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); paraffin sulfonate surfactants having the general formula $RSO_3$ M, wherein R is a primary or secondary alkyl group containing from about 8 to about 22 carbon atoms (preferably 10 to 18 carbon atoms) and M is an alkali metal, e.g., sodium, lithium or potassium; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 10 moles of ethylene oxide; sodium or potassium salts of alkyl phenol ethylene oxide ether sulfates with about 1 to about 10 units of ethylene oxide per molecule and in which the alkyl radicals contain from about 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium β-acetoxy- or β-acetamido-alkanesulfonates where the alkane has from 8 to 22 carbon atoms.

A preferred class of anionic surfactants are linear alkyl benzene sulfonate surfactant wherein the alkyl portion contains 8 to 16 carbon atoms, and most preferably about 11 to 13 carbon atoms. According to particularly preferred embodiments of the invention, the solid block compositions necessarily include an anionic surfactant.

A further preferred class of anionic surfactants are alpha olefin sulfonates, as well as salts thereof, e.g., alkali metal salts. Preferred are $C_8$ through $C_{22}$ alpha olefin sulfonates, particularly $C_{12}$ through $C_{18}$, and especially $C_{14}$, and $C_{16}$ alpha olefin sulfonates as well as blends of two or more thereof. According to particularly preferred embodiments of the invention, the solid block compositions necessarily include an alpha olefin sulfonate anionic surfactant.

The detersive surfactant constituent of the solid block composition of the invention may include one or more nonionic surfactants. Practically any hydrophobic compound having a carboxy, hydroxy, amido, or amino group with a free hydrogen attached to the nitrogen can be condensed with an alkylene oxide, especially ethylene oxide or with the polyhydration product thereof, a polyalkylene glycol, especially polyethylene glycol, to form a water soluble or water dispersible nonionic surfactant compound. Further, the length of the polyethenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

One class of useful nonionic surfactants include polyalkylene oxide condensates of alkyl phenols. These compounds include the condensation products of alkyl phenols having an alkyl group containing from about 6 to 12 carbon atoms in either a straight chain or branched chain configuration with an alkylene oxide, especially an ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

A further class of useful nonionic surfactants include the condensation products of aliphatic alcohols with from about 1 to about 60 moles of an alkylene oxide, especially an ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol and the condensation product of about 9 moles of ethylene oxide with coconut alcohol (a mixture of fatty alcohols with alkyl chains varying in length from about 10 to 14 carbon atoms). Other examples are those $C_6$-$C_{11}$ straight-chain alcohols which are ethoxylated with from about 3 to about 6 moles of ethylene oxide. Their derivation is well known in the art. Examples include Alfonic® 810-4.5, which is described in product literature from Sasol as a $C_8$-$C_{10}$ straight-chain alcohol having an average molecular weight of 356, an ethylene oxide content of about 4.85 moles (about 60 wt. %), and an HLB of about 12; Alfonic® 810-2, which is described in product literature as a $C_8$-$C_{10}$ straight-chain alcohols having an average molecular weight of 242, an ethylene oxide content of about 2.1 moles (about 40 wt. %), and an HLB of about 12; and Alfonic® 610-3.5, which is described in product literature as having an average molecular weight of 276, an ethylene oxide content of about 3.1 moles (about 50 wt. %), and an HLB of 10. Other examples of alcohol ethoxylates are $C_{10}$ oxo-alcohol ethoxylates available from BASF under the Lutensol® ON tradename. They are available in grades containing from about 3 to about 11 moles of ethylene oxide (available under the names Lutensol® ON 30; Lutensol® ON 50; Lutensol® ON 60; Lutensol® ON 65; Lutensol® ON 66; Lutensol® ON 70; Lutensol® ON 80; and Lutensol®ON 110). Other examples of ethoxylated alcohols include the Neodol® 91 series non-ionic surfactants available from Shell Chemical Company which are described as $C_9$-$C_{11}$ ethoxylated alcohols. The Neodol® 91 series non-ionic surfactants of interest include Neodol® 91-2.5, Neodol® 91-6, and Neodol® 91-8. Neodol® 91-2.5 has been described as having about 2.5 ethoxy groups per molecule; Neodol 91-6 has been described as having about 6 ethoxy groups per molecule; and Neodol 91-8 has been described as having about 8 ethoxy groups per molecule. Further examples of ethoxylated alcohols include the Rhodasurf® DA series non-ionic surfactants available from Rhodia which are described to be branched isodecyl alcohol ethoxylates. Rhodasurf® DA-530 has been described as having 4 moles of ethoxylation and an HLB of 10.5; Rhodasurf® DA-630 has been described as having 6 moles of ethoxylation with an HLB of 12.5; and Rhodasurf® DA-639 is a 90% solution of DA-630. Further examples of ethoxylated alcohols include those from Tomah Products (Milton, Wis.) under the Tomadol® tradename with the formula $RO(CH_2CH_2O)_nH$ where R is the primary linear alcohol and n is the total number of moles of ethylene oxide. The ethoxylated alcohol series from Tomah include 91-2.5; 91-6; 91-8—where R is linear $C_9/C_{10}/C_{11}$ and n is 2.5, 6, or 8; 1-3; 1-5; 1-7; 1-73B; 1-9; where R is linear $C_{11}$ and n is 3, 5, 7 or 9; 23-1; 23-3; 23-5; 23-6.5—where R is linear $C_{12}/C_{13}$ and n is 1, 3, 5, or 6.5; 25-3; 25-7; 25-9; 25-12—where R is linear $C_{12}/C_{13}/$ $C_{14}/C_{15}$ and n is 3, 7, 9, or 12; and 45-7; 45-13—where R is linear $C_{14}/C_{15}$ and n is 7 or 13.

A further class of useful nonionic surfactants include primary and secondary linear and branched alcohol ethoxylates, such as those based on $C_6$-$C_{18}$ alcohols which further include an average of from 2 to 80 moles of ethoxylation per mol of alcohol. These examples include the Genapol® UD (ex. Clariant, Muttenz, Switzerland) described under the tradenames Genapol® UD 030, $C_{11}$-oxo-alcohol polyglycol ether with 3 EO; Genapol® UD, 050 $C_{11}$-oxo-alcohol polyglycol ether with 5 EO; Genapol® UD 070, $C_{11}$-oxo-alcohol polyglycol ether with 7 EO; Genapol® UD 080, $C_{11}$-oxo-alcohol polyglycol ether with 8 EO; Genapol® UD 088, $C_{11}$-oxo-alcohol polyglycol ether with 8 EO; and Genapol® UD 110, $C_{11}$-oxo-alcohol polyglycol ether with 11 EO.

Exemplary useful nonionic surfactants include the condensation products of a secondary aliphatic alcohols containing 8 to 18 carbon atoms in a straight or branched chain configuration condensed with 5 to 30 moles of ethylene oxide. Examples of commercially available nonionic detergents of the foregoing type are those presently commercially available under the trade name of Tergitol® such as Tergitol 15-S-12 which is described as being $C_{11}$-$C_{15}$ secondary alkanol condensed with 9 ethylene oxide units, or Tergitol 15-S-9 which is described as being $C_{11}$-$C_{15}$ secondary alkanol condensed with 12 ethylene oxide units per molecule.

A further class of useful nonionic surfactants include those surfactants having a formula:

$$RO(CH_2CH_2O)_nH$$

wherein;
R is a mixture of linear, even carbon-number hydrocarbon chains ranging from $C_{12}H_{25}$ to $C_{16}H_{33}$ and n represents the number of ethoxy repeating units and is a number of from about 1 to about 12.

Surfactants of this formula are presently marketed under the Genapol® tradename (ex. Clariant), which surfactants include the "26-L" series of the general formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from 1 to about 12, such as 26-L-1,26-L-1,6,26-L-2,26-L-3,26-L-5,26-L-45, 26-L-50, 26-L-60, 26-L-60N, 26-L-75, 26-L-80, 26-L-98N, and the 24-L series, derived from synthetic sources and typically contain about 55% $C_{12}$ and 45% $C_{14}$ alcohols, such as 24-L-3,24-L-45, 24-L-50, 24-L-60, 24-L-60N, 24-L-75, 24-L-92, and 24-L-98N, all sold under the Genapol® tradename.

Further useful non-ionic surfactants which may be used in the inventive compositions include those presently marketed under the trade name Pluronics® (ex. BASF). The compounds are formed by condensing ethylene oxide with a hydrophobic base formed by the condensation of propylene oxide with propylene glycol. The molecular weight of the hydrophobic portion of the molecule is of the order of 950 to 4,000 and preferably 200 to 2,500. The addition of polyoxyethylene radicals of the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants are in liquid form and particularly satisfactory surfactants are available as those marketed as Pluronics® L62 and Pluronics® L64.

Further nonionic surfactants which may be included in the inventive compositions include alkoxylated alkanolamides, preferably $C_8$-$C_{24}$ alkyl di($C_2$-$C_3$ alkanol amides), as represented by the following formula:

$$R_5—CO—NH—R_6—OH$$

wherein $R_5$ is a branched or straight chain $C_8$-$C_{24}$ alkyl radical, preferably a $C_{10}$-$C_{16}$ alkyl radical and more preferably a $C_{12}$-$C_{14}$ alkyl radical, and $R_6$ is a $C_1$-$C_4$ alkyl radical, preferably an ethyl radical.

According to certain particularly preferred embodiments the detersive surfactant constituent necessarily comprises a nonionic surfactant based on a linear primary alcohol ethoxylate particularly wherein the alkyl portion is a $C_8$ to $C_{16}$, but particularly a $C_9$ to $C_{11}$ alkyl group, and having an average of between about 6 to about 8 moles of ethoxylation.

One further useful class of nonionic surfactants include those in which the major portion of the molecule is made up of block polymeric $C_2$-$C_4$ alkylene oxides, with alkylene oxide blocks containing $C_3$ to $C_4$ alkylene oxides. Such nonionic surfactants, while preferably built up from an alkylene oxide chain starting group, can have as a starting nucleus almost any active hydrogen containing group including, without limitation, amides, phenols, and secondary alcohols.

One group of nonionic surfactants containing the characteristic alkylene oxide blocks are those which may be generally represented by the formula (A):

$$HO\text{-}(EO)_x(PO)_y(EO)_z\text{—}H \qquad (A)$$

where
EO represents ethylene oxide,
PO represents propylene oxide,
y equals at least 15,
$(EO)_{x+z}$ equals 20 to 50% of the total weight of said compounds, and, the total molecular weight is preferably in the range of about 2000 to 15,000.

Another group of nonionic surfactants appropriate for use in the new compositions can be represented by the formula (B):

$$R\text{-}(EO,PO)_a(EO,PO)_b\text{—}H \qquad (B)$$

wherein R is an alkyl, aryl or aralkyl group,
the alkoxy group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by Formula B include butoxy derivatives of propylene oxide/ethylene oxide block polymers having molecular weights within the range of about 2000-5000.

Still further useful nonionic surfactants containing polymeric butoxy (BO) groups can be represented by formula (C) as follows:

$$RO\text{—}(BO)_n(EO)_x\text{—}H \qquad (C)$$

wherein R is an alkyl group containing 1 to 20 carbon atoms, n is about 15 and x is about 15.

Also useful as the nonionic block copolymer surfactants which also include polymeric butoxy groups are those which may be represented by the following formula (D):

$$HO\text{-}(EO)_x(BO)_n(EO)_y\text{—}H \qquad (D)$$

wherein
n is about 15,
x is about 15 and
y is about 15.

Still further useful nonionic block copolymer surfactants include ethoxylated derivatives of propoxylated ethylene diamine, which may be represented by the following formula:

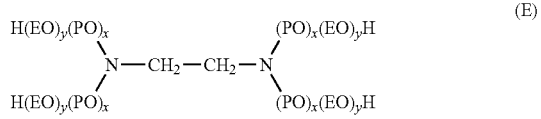

where
(EO) represents ethoxy,
(PO) represents propoxy,
the amount of $(PO)_x$ is such as to provide a molecular weight prior to ethoxylation of about 300 to 7500, and the amount of $(EO)_y$ is such as to provide about 20% to 90% of the total weight of said compound.

Further useful nonionic surfactants include nonionic amine oxide constituent. Exemplary amine oxides include:

A) Alkyl di(lower alkyl)amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide;

B) Alkyl di(hydroxy lower alkyl)amine oxides in which the alkyl group has about 10-20, and preferably 12-16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide;

C) Alkylamidopropyl di(lower alkyl)amine oxides in which the alkyl group has about 10-20, and preferably 12-16 carbon atoms, and can be straight or branched chain, saturated or unsaturated. Examples are cocoamidopropyl dimethyl amine oxide and tallowamidopropyl dimethyl amine oxide; and D) Alkylmorpholine oxides in which the alkyl group has about 10-20, and preferably 12-16 carbon atoms, and can be straight or branched chain, saturated or unsaturated.

Preferably the amine oxide constituent is an alkyl di (lower alkyl) amine oxide as denoted above and which may be represented by the following structure:

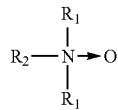

wherein each:
$R_1$ is a straight chained $C_1$-$C_4$ alkyl group, preferably both $R_1$ are methyl groups; and,
$R_2$ is a straight chained $C_8$-$C_{18}$ alkyl group, preferably is $C_{10}$-$C_{14}$ alkyl group, most preferably is a $C_{12}$ alkyl group. Each of the alkyl groups may be linear or branched, but most preferably are linear. Most preferably the amine oxide constituent is lauryl dimethyl amine oxide. Technical grade mixtures of two or more amine oxides may be used, wherein amine oxides of varying chains of the $R_2$ group are present. Preferably, the amine oxides used in the present invention include $R_2$ groups which comprise at least 50% wt., preferably at least 60% wt. of $C_{12}$ alkyl groups and at least 25% wt. of $C_{14}$ alkyl groups, with not more than 15% wt. of $C_{16}$, $C_{18}$ or higher alkyl groups as the $R_2$ group.

Still further exemplary useful nonionic surfactants which may be used include certain alkanolamides including monoethanolamides and diethanolamides, particularly fatty monoalkanolamides and fatty dialkanolamides.

A cationic surfactant may be incorporated as a germicide or as a detersive surfactant in the solid block composition of the present invention, particularly wherein a bleach constituent is absent from the solid block composition. Cationic surfactants are per se, well known, and exemplary useful cationic surfactants may be one or more of those described for example in *McCutcheon's Functional Materials*, Vol. 2, 1998; *Kirk-Othmer, Encyclopedia of Chemical Technology*, 4th Ed., Vol. 23, pp. 481-541 (1997), the contents of which are herein incorporated by reference. These are also described in the respective product specifications and literature available from the suppliers of these cationic surfactants.

Examples of preferred cationic surfactant compositions useful in the practice of the instant invention are those which provide a germicidal effect to the concentrate compositions, and especially preferred are quaternary ammonium compounds and salts thereof, which may be characterized by the general structural formula:

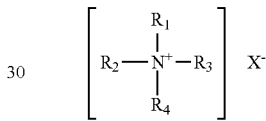

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

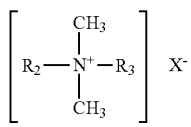

wherein $R_2$ and $R_3$ are the same or different $C_8$-$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Such useful quaternary compounds are available under the BARDAC®, BARQUAT®, HYAMINE®, LONZABAC®, and ONYXIDE® trademarks, which are more fully described in, for example, *McCutcheon's Functional Materials* (Vol. 2), North American Edition, 1998, as well as the respective product literature from the suppliers identified below. For example, BARDAC® 205M is described to be a liquid containing alkyl dimethyl benzyl ammonium chloride, octyl decyl dimethyl ammonium chloride; didecyl dimethyl ammonium chloride, and dioctyl dimethyl ammonium chloride (50% active) (also available as 80% active (BARDAC® 208M)); described generally in McCutcheon's as a combination of alkyl dimethyl benzyl ammonium chloride and dialkyl dimethyl ammonium chloride); BARDAC® 2050 is described to be a combination of octyl decyl dimethyl ammonium chloride/didecyl dimethyl ammonium chloride, and dioctyl dimethyl ammonium chloride (50% active) (also available as 80% active (BARDAC® 2080)); BARDAC® 2250 is described to be didecyl dimethyl ammonium chloride (50% active); BARDAC® LF (or BARDAC® LF-80), described as being based on dioctyl dimethyl ammonium chloride (BARQUAT® MB-50, MX-50, OJ-50 (each 50% liquid) and MB-80 or MX-80 (each 80% liquid) are each described as an alkyl dimethyl benzyl ammonium chloride; BARDAC® 4250 and BARQUAT® 4250Z (each 50% active) or BARQUAT® 4280 and BARQUAT 4280Z (each 80% active) are each described as alkyl dimethyl benzyl ammonium chloride/alkyl dimethyl ethyl benzyl ammonium chloride. Also, HYAMINE® 1622, described as diisobutyl phenoxy ethoxy ethyl dimethyl benzyl ammonium chloride (50% solution); HYAMINE® 3500 (50% actives), described as alkyl dimethyl benzyl ammonium chloride (also available as 80% active (HYAMINE® 3500-80)); and HYAMINE® 2389 described as being based on methyldodecylbenzyl ammonium chloride and/or methyldodecylxylene-bis-trimethyl ammonium chloride. (BARDAC®, BARQUAT® and HYAMINE® are presently commercially available from Lonza, Inc., Fairlawn, N.J.). BTC® 50 NF (or BTC® 65 NF) is described to be alkyl dimethyl benzyl ammonium chloride (50% active); BTC® 99 is described as didecyl dimethyl ammonium chloride (50% active); BTC® 776 is described to be myrisalkonium chloride (50% active); BTC® 818 is described as being octyl decyl dimethyl ammonium chloride, didecyl dimethyl ammonium chloride, and dioctyl dimethyl ammonium chloride (50% active) (available also as 80% active (BTC® 818-80%)); BTC® 824 and BTC® 835 are each described as being of alkyl dimethyl benzyl ammonium chloride (each 50% active); BTC® 885 is described as a combination of BTC® 835 and BTC® 818 (50% active) (available also as 80% active (BTC® 888)); BTC® 1010 is described as didecyl dimethyl ammonium chloride (50% active) (also available as 80% active (BTC® 1010-80)); BTC® 2125 (or BTC® 2125 M) is described as alkyl dimethyl benzyl ammonium chloride and alkyl dimethyl ethylbenzyl ammonium chloride (each 50% active) (also available as 80% active (BTC® 2125 80 or BTC® 2125 M)); BTC® 2565 is described as alkyl dimethyl benzyl ammonium chlorides (50% active) (also available as 80% active (BTC® 2568)); BTC® 8248 (or BTC® 8358) is described as alkyl dimethyl benzyl ammonium chloride (80% active) (also available as 90% active (BTC® 8249)); ONYXIDE® 3300 is described as n-alkyl dimethyl benzyl ammonium saccharinate (95% active). (BTC® and ONYXIDE® are presently commercially available from Stepan Company, Northfield, Ill.) Polymeric quaternary ammonium salts based on these monomeric structures are also considered desirable for the present invention. One example is POLYQUAT®, described as being a 2-butenyldimethyl ammonium chloride polymer.

Preferred quaternary germicides used in the compressed solid block compositions are those which are supplied in a solid or powdered form, as such greatly facilitates the manufacture of the compressed solid block compositions.

When present in a compressed solid block composition, it is preferred that the germicidal cationic surfactant(s) are present in amounts so to dispense at least about 200 parts per million (ppm) in the water flushed into the sanitary appliance, e.g., toilet bowl, or into the water retained in the sanitary appliance at the conclusion of the flush cycle.

Further detersive surfactants which may be included are amphoteric and zwitterionic surfactants which provide a detersive effect. Exemplary useful amphoteric surfactants include alkylbetaines, particularly those which may be represented by the following structural formula:

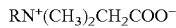

wherein R is a straight or branched hydrocarbon chain which may include an aryl moiety, but is preferably a straight hydrocarbon chain containing from about 6 to 30 carbon atoms. Further exemplary useful amphoteric surfactants include amidoalkylbetaines, such as amidopropylbetaines which may be represented by the following structural formula:

wherein R is a straight or branched hydrocarbon chain which may include an aryl moiety, but is preferably a straight hydrocarbon chain containing from about 6 to 30 carbon atoms.

As noted above, preferred detersive surfactants are those which exhibit a melting points above about 110° F., preferably above 125° F., in order to permit convenient processing according to known art techniques. Nonetheless small amounts of low melting point surfactants, i.e., those exhibiting melting points below about 110° F. and even liquid surfactants may be used in providing the surfactant constituent of the solid block composition.

As the performance requirements of the compressed solid blocks may differ according to their use as either an ITB or as an ITC block, the amounts of the constituents present in the block may vary as well depending upon the final intended use of the treatment block.

When intended for use as an ITB block, the detersive surfactant constituent may be present in any effective amount and generally comprises up to about 90% wt. of the total weight of the solid block composition, and the resultant treatment block formed therefrom. Preferably the detersive surfactant constituent comprises about 20-90% wt., more preferably 35-80% wt. of the solid block composition, and when used as an ITB block the detersive surfactant constituent most preferably comprises about 50-75% wt. of the solid block composition, and the resultant treatment block formed therefrom. When intended for use as an ITC block, the detersive surfactant constituent may be present in any effective amount and generally comprises up to about 60% wt. of the total weight of the solid block composition, and the resultant treatment block formed therefrom. Preferably the detersive surfactant constituent comprises about 10-55% wt., more preferably 20-50% wt. of the solid block composition, and the resultant treatment block formed therefrom.

In particularly preferred embodiments the compressed solid blocks of the invention necessarily comprise at least one surfactant, preferably at least one anionic surfactant.

Further exemplary chemical constituents may be one or more sanitizing agents or germicides which may be present with our without other constituents being present in the compressed solid blocks of the cageless lavatory dispensing devices.

The sanitizing agent can be any sanitizing composition known to those of ordinary skill in the relevant art, and without limitation exemplary sanitizing compositions include materials containing alkyl halohydantoins, alkali metal haloisocyanurates, bleach, essential oils, non-quaternary ammonium based germicidal compounds as well as quaternary ammonium germicidal compounds.

By way of non-limiting example, exemplary a bleach constituent. The bleach constituent is relatively inert in the dry state but, which on contact with water, releases oxygen, hypohalite or a halogen especially chlorine. Representative examples of typical oxygen-release bleaching agents, suitable for incorporation in the solid block composition include the alkali metal perborates, e.g., sodium perborate, and alkali metal monopersulfates, e.g., sodium monopersulfates, potassium monopersulfate, alkali metal monoperphosphates, e.g., disodium monoperphosphate and dipotassium monoperphosphate, as well as other conventional bleaching agents capable of liberating hypohalite, e.g., hypochlorite and/or hypobromite, include heterocyclic N-bromo- and N-chloro-cyanurates such as trichloroisocyanuric and tribromoiscyanuric acid, dibromocyanuric acid, dichlorocyanuric acid, N-monobromo-N-mono-chlorocyanuric acid and N-monobromo-N, N-dichlorocyanuric acid, as well as the salts thereof with water solubilizing cations such as potassium and sodium, e.g., sodium N-monobromo-N-monochlorocyanurate, potassium dichlorocyanurate, sodium dichlorocyanurate, as well as other N-bromo and N-chloro-imides, such as N-brominated and N-chlorinated succinimide, malonimide, phthalimide and naphthalimide. Also useful in the solid block composition as hypohalite-releasing bleaches are halohydantoins which may be used include those which may be represented by the general structure:

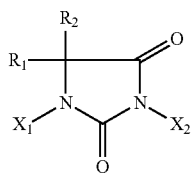

wherein:

$X_1$ and $X_2$ are independently hydrogen, chlorine or bromine; and, $R_1$ and $R_2$ are independently alkyl groups having from 1 to 6 carbon atoms. Examples of halohydantoins include, for example, N,N'-dichloro-dimethyl-hydantoin, N-bromo-N-chloro-dimethyl-hydantoin, N,N'-dibromo-dimethyl-hydantoin, 1,4-dichloro, 5,5-dialkyl substituted hydantoin, wherein each alkyl group independently has 1 to 6 carbon atoms, N-monohalogenated hydantoins such as chlorodimethylhydantoin (MCDMH) and N-bromo-dimethylhydantoin (MBDMH); dihalogenated hydantoins such as dichlorodimethylhydantoin (DCDMH), dibromodimethylhydantoin (DBDMH), and 1-bromo-3-chloro-5,5,-dimethylhydantoin (BCDMH); and halogenated methylethylhydantoins such as chloromethylethylhydantion (MCMEH), dichloromethylethylhydantoin (DCMEH), bromomethylethylhydantoin (MBMEH), dibromomethylethylhydantoin (DBMEH), and bromochloromethylethylhydantoin (BCMEH), and mixtures thereof. Other suitable organic hypohalite liberating bleaching agents include halogenated melamines such as tribromomelamine and trichloromelamine. Suitable inorganic hypohalite-releasing bleaching agents include lithium and calcium hypochlorites and hypobromites. The various chlorine, bromine or hypohalite liberating agents may, if desired, be provided in the form of stable, solid complexes or hydrates, such as sodium p-toluene sulfobromamine trihydrate; sodium benzene sulfochloramine dihydrate; calcium hypobromite tetrahydrate; and calcium hypochlorite tetrahydrate. Brominated and chlorinated trisodium phosphates formed by the reaction of the corresponding sodium hypohalite solution with trisodium orthophosphate (and water, as necessary) likewise comprise useful inorganic bleaching agents for incorporation into the inventive solid block composition and the treatment blocks formed therefrom.

When present, preferably the bleach constituent is a hypohalite liberating compound and more preferably is a hypohalite liberating compound in the form of a solid complex or hydrate thereof. Particularly preferred are chloroisocynanuric acids and alkali metal salts thereof, preferably potassium, and especially sodium salts thereof. Examples of such compounds include trichloroisocyananuric acid, dichloroisocyanuric acid, sodium dichloroisocyanurate, potassium dichloroisocyanurate, and trichloro-potassium dichloroisocyanurate complex. The most preferred chlorine bleach material is sodium dichloroisocyanurate; the dihydrate of this material being particularly preferred.

When present, the bleach constituent may be present in any effective amount and may comprise up to about 90% wt., preferably at least about 0.1-60% wt of the compressed solid block composition. More preferably, when present, the bleach constituent comprises about 0.5-50% wt., more preferably at least 1-40% wt. of the compressed solid block composition.

Other germicidally effective agents useful as sanitizing agents include sodium dichloroisocyanurate (DCCNa) and sodium dibromoisocyanurate. Further examples of non-quaternary ammonium based sanitizing agents include pyrithiones, dimethyldimethylol hydantoin, methylchloroisothiazolinone/methylisothiazolinone sodium sulfite, sodium bisulfite, imidazolidinyl urea, diazolidinyl urea, benzyl alcohol, 2-bromo-2-nitropropane-1,3-diol, formalin (formaldehyde), iodopropenyl butylcarbamate, chloroacetamide, methanamine, methyldibromonitrile glutaronitrile, glutaraldehyde, 5-bromo-5-nitro-1,3-dioxane, phenethyl alcohol, o-phenylphenol/sodium o-phenylphenol, sodium hydroxymethylglycinate, polymethoxy bicyclic oxazolidine, dimethoxane, thimersal dichlorobenzyl alcohol, captan, chlorphenenesin, dichlorophene, chlorbutanol, glyceryl laurate, halogenated diphenyl ethers, phenolic compounds, mono- and poly-alkyl and aromatic halophenols, resorcinol and its derivatives, bisphenolic compounds, benzoic esters (parabens), halogenated carbanilides, 3-trifluoromethyl-4,4'-dichlorocarbanilide, and 3,3',4-trichlorocarbanilide. More preferably, the non-cationic antimicrobial agent is a mono- and poly-alkyl and aromatic halophenol selected from the group p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, and 5-chloro-2-hydroxydiphenylmethane.

Quaternary ammonium based sanitizing agents include any cationic surfactant which is known or may be found to provide a broad antibacterial or sanitizing function; these have been described above with reference to detersive surfactants.

As a further chemical constituent, the compressed solid block compositions of the invention may also comprise a coloring agent which imparts either a color to the compressed solid blocks, to the water in which it comes into contact, but especially which imparts color to the water contained within the sanitary appliance. Where the sanitary appliance is a toilet, desirably the coloring agent imparts a color to the water contained within the cistern, or within the toilet bowl particularly following the flush cycle of a toilet, or may impart a color in both locations. Such coloring agents have great consumer appeal, and indeed any known art coloring agent may be provided in any effective amount in order to impart a coloring effect. Colorants, especially dyes, are preferred when formulated as dry powders to enable direct incorporation into compressed solid blocks of the invention, however, liquid colorants may be employed in conjunction with suitable carriers. Useful colorants include any materials which may provide a desired coloring effect. Exemplary useful coloring agents include dyes, e.g., Alizarine Light Blue B (C.I. 63010), Carta Blue VP (C.I. 24401), Acid Green 2G (C.I. 42085), Astragon Green D (C.I. 42040) Supranol Cyanine 7B (C.I. 42675), Maxilon Blue 3RL (C.I. Basic Blue 80), acid yellow 23, acid violet 17, a direct violet dye (Direct violet 51), Drimarine Blue Z-RL (C.I. Reactive Blue 18), Alizarine Light Blue H-RL (C.I. Acid Blue 182), FD&C Blue No. 1, FD&C Green No. 3 and Acid Blue No. 9. When a bleach constituent is included in the compressed solid block composition, the colorant, e.g., dye, should be selected so to ensure the compatibility of the colorant with the bleach constituent, or so that its color persists despite the presence in the toilet bowl of a concentration of hypochlorite which is effective to maintain sanitary conditions. Frequently however, a compressed solid block composition which includes a bleach constituent do not comprise any colorants. Desirably the colorants, when present, do not exceed 15% wt. of the compressed solid block composition, although generally lesser amounts are usually effective. When present, colorants are desirably present in an amount from about 0.1 to 15 percent of the total weight of the chemical composition.

The compressed solid block compositions may include a fragrance or other air treatment constituent. The fragrance may be any composition which is known to the art to provide a perceptible fragrancing benefit, any may be based on naturally occurring materials such as one or more essential oils, or may be based on synthetically produced compounds as well. Examples of essential oils include pine oil, Anetlhole 20/21 natural, Aniseed oil china star, Aniseed oil globe brand, Balsam (Perui), Basil oil (India), Black pepper oil, Black pepper oleoresin 40/20, Bois de Rose (Brazil) FOB, Bomneol Flakes (China), Camphor oil, White, Camphor powder synthetic technical, Canaga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Counmarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), and Wintergreen oil.

Many of these essential function as a fragrance agent, which fragrance agent which may be a substance or mixture of various substances including those which are naturally derived (i.e., obtained by extraction of flower, herb, blossom or plant), those which are artificially derived or produced (i.e., mixture of natural oils and/or oil constituents), and those which are synthetically produced substances (odiferous substances). Generally fragrance agents are complex mixtures or blends various organic compounds including, but not limited to, certain alcohols, aldehydes, ethers, alamatic compounds and varying amounts of essential oils such as from about 0 to about 25% by weight, usually from about 0.05 to about 12% by weight, the essential oils themselves being volatile odiferous compounds and also functioning to aid in the dissolution of the other components of the fragrance agent. In the present invention, the precise composition of the fragrance agent desirably emanates a pleasing fragrance, but the nature of the fragrance agent is not critical to the success of the invention.

As noted above, in conjunction with or in the absence of a fragrance constituent, the compressed solid block compositions may comprise an air treatment constituent. Such may be any other material which is useful in providing treatment of ambient air, such as a sanitizing agents. e.g., one or more glycols or alcohols, or materials which are intended to counteract, neutralize, or mask odors in the absence of, or in conjunction with, the fragrance composition of the present invention. Alternatively, the air treatment constituent may be one or more materials which provide and effective insecticide repelling or insecticidal benefit; such would be particularly useful in climates or environments where insects present a nuisance or health hazard.

As further chemical constituents, the compressed solid block compositions of the invention may comprise an anti-limescale agent, which can be generally classified as a cleaning agent in that it provides a cleaning effect to treated lavatory device surfaces. The anti-limescale agent can virtually any known anti-limescale agent compositions known to those of ordinary skill in the relevant art. For example, compositions containing anionic and/or nonionic surfactants together with typical anti-limescale agents, for example, amidosulfonic acid, bisulfate salts, organic acids, organic phosphoric salts, alkali metal polyphosphates, and the like. Examples of anti-limescale agent compositions can be found in, for example, U.S. Pat. Nos. 5,759,974; 4,460,490; and 4578207, the contents of which are herein incorporated by reference. Further examples of anti-limescale agents include organic acids (for example, citric acid, lactic acid, adipic acid, oxalic acid and the like), organic phosphoric salts, alkali metal polyphosphates, sulfonic, and sulfamic acids and their salts, bisulfate salts, EDTA, phosphonates, and the like.

The compressed solid block compositions may comprise stain inhibiting materials. The solid block composition of the invention may, for example, include an effective amount of a manganese stain inhibiting agent which is advantageously included wherein the sanitary appliance is supplied by a water source having an appreciable or high amount of manganese. Such water containing a high manganese content are known to frequently deposit unsightly stains on surfaces of sanitary appliances, especially when the solid block composition also contains a bleach source which provides a hypochlorite. To counteract such an effect the solid block composition of the present invention may comprise a manganese stain inhibiting agent, such as a partially hydrolyzed polyacrylamide having a molecular weight of about 2000 to about 10,000, a polyacrylate with a molecular weight of about 2000 to about 10,000, and/or copolymers of ethylene and maleic acid anhydride with a molecular weight of from about 20,000 to about 100,000. When present the satin inhibiting materials may comprise to about 10% wt. of the weight of the compressed solid block composition.

The compressed solid block compositions of the invention may include one or more preservatives. Such preservatives are primarily included to reduce the growth of undesired microorganisms within the treatment blocks formed from the solid block composition during storage prior to use or while used, although it is expected that the such a preservative may impart a beneficial antimicrobial effect to the water in the sanitary appliance to which the treatment block is provided. Exemplary useful preservatives include compositions which include parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. For reasons of availability, the most preferred preservative are those commercially available preservative comprising a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.). Further useful preservative compositions include KATHON® CG/ICP II, a further preservative composition presently commercially available from Rohm and Haas (Philadelphia, Pa.), PROXEL® which is presently commercially available from Zeneca Biocides (Wilmington, Del.), SUTTOCIDE® A which is presently commercially available from Sutton Laboratories (Chatam, N.J.) as well as TEXTAMER® 38AD which is presently commercially available from Calgon Corp. (Pittsburgh, Pa.). When present, the optional preservative constituent should not exceed about 5% wt. of the solid block composition, although generally lesser amounts are usually effective.

The inventive compressed solid block compositions may include a binder constituent. The binder may function in part controlling the rate of dissolution of the tablet. The binder constituent may be a clay, but preferably is a water-soluble or water-dispersible gel-forming organic polymer. The term "gel-forming" as applied to this polymer is intended to indicate that on dissolution or dispersion in water it first forms a gel which, upon dilution with further water, is dissolved or dispersed to form a free-flowing liquid. The organic polymer serves essentially as binder for the tablets produced in accordance with the invention although, as will be appreciated, certain of the polymers envisaged for use in accordance with the invention also have surface active properties and thereby serve not only as binders but also enhance the cleansing ability of the tablets of the invention. Further certain organic polymers, such as substituted celluloses, also serve as soil antiredeposition agents. A wide variety of water-soluble organic polymers are suitable for use in the solid block composition of the present invention. Such polymers may be wholly synthetic or may be semi-synthetic organic polymers derived from natural materials. Thus, for example, on class of organic polymers for use in accordance with the invention are chemically modified celluloses such as ethyl cellulose, methyl cellulose, sodium carboxymethyl cellulose, hydroxypropyl cellulose, hydroxypropyl methyl cellulose, ethyl hydroxyethyl cellulose, carboxymethyl hydroxyethyl cellulose, and hydroxyethyl cellulose. Another class of organic polymers which may be used include naturally derived or manufactured (fermented) polymeric materials such as alginates and carageenan. Also, water-soluble starches and gelatin may be used as the optional binder constituent. The cellulose based binders are a preferred class of binders for use in the solid block composition and may possess the property of inverse solubility that is their solubility decreases with increasing temperature, thereby rendering the tablets of the invention suitable for use in locations having a relatively high ambient temperature.

The optional binder constituent may also be one or more synthetic polymers e.g., polyvinyl alcohols; water-soluble partially hydrolyzed polyvinyl acetates; polyacrylonitriles; polyvinyl pyrrolidones; water-soluble polymers of ethylenically unsaturated carboxylic acids, such as acrylic acid and methacrylic acid, and salts thereof; base-hydrolysed starch-polyacrylonitrile copolymers; polyacrylamides; ethylene oxide polymers and copolymers; as well as carboxypolymethylenes.

In the case of the organic polymeric binders it may be noted that, in general, the higher the molecular weight of the polymer the greater the in-use life of the treatment block of the invention. When present, the total binder content may comprise up to 75% wt. of the solid block composition, but preferably is from 0.5 to 70% by weight, preferably from 1 to 65% by weight, more preferably from 5 to 60% by weight.

The solid block composition may optionally include one or more dissolution control agents. Such dissolution control agent are materials which provide a degree of hydrophobicity to the treatment block formed from the solid block composition whose presence in the treatment block contributes to the slow uniform dissolution of the treatment block when contacted with water, and simultaneously the controlled release of the active constituents of the solid block composition. Preferred for use as the dissolution control agents are mono- or di-alkanol amides derived from $C_8$-$C_{16}$ fatty acids, especially $C_{12}$-$C_{14}$ fatty acids having a $C_2$-$C_6$ monoamine or diamine moiety. When included the dissolution control agent may be included in any effective amount, but desirably the dissolution control agent is present in an amount not to exceed about 600% wt. of the solid block composition, although generally lesser amounts are usually effective. Generally wherein the treatment block is to be used in an ITB application the dissolution control agent is present to about 12% wt., more preferably is present from 0.1-10% wt. and most preferably is present from about 3-8% wt. of the solid block compositions, as well as in the treatment blocks formed therefrom. Generally wherein the treatment block is to be used in an ITC application the dissolution control agent is present to about 50% wt., more preferably is present from 1-50% wt. and most preferably is present from about 10-40% wt. of the solid block compositions, as well as in the treatment blocks formed therefrom.

The compressed solid block compositions may optionally include one or more water-softening agents or one or more chelating agents, for example inorganic water-softening agents such as sodium hexametaphosphate or other alkali metal polyphosphates or organic water-softening agents such as ethylenediaminetetraacetic acid and nitrilotriacetic acid and alkali metal salts thereof. When present, such water-softening agents or chelating agents should not exceed about 20% wt. of the solid block composition, although generally lesser amounts are usually effective.

The compressed solid block composition may optionally include one or more solid water-soluble acids or acid-release agents such as sulphamic acid, citric acid or sodium hydrogen sulphate. When present, such solid water-soluble acids or acid-release agents should not exceed about 20% wt. of the solid block composition, although generally lesser amounts are usually effective.

The compressed solid block compositions may include diluent materials may be included to provide additional bulk of the product solid block composition and may enhance leaching out of the surfactant constituent when the solid block composition is placed in water. Exemplary diluent materials include any soluble inorganic alkali, alkaline earth metal salt or hydrate thereof, for example, chlorides such as sodium chloride, magnesium chloride and the like, carbonates and bicarbonates such as sodium carbonate, sodium bicarbonate and the like, sulfates such as magnesium sulfate, copper sulfate, sodium sulfate, zinc sulfate and the like, borax, borates such as sodium borate and the like, as well as others known to the art but not particularly recited herein. Exemplary organic diluents include, inter alia, urea, as well as water soluble high molecular weight polyethylene glycol and polypropylene glycol. When present, such diluent materials should not exceed about 80% wt. of the compressed solid block composition, although generally lesser amounts are usually effective.

The compressed solid block composition and treatment blocks formed therefrom may include one or more fillers. Such fillers are typically particulate solid water-insoluble materials which may be based on inorganic materials such as talc or silica, particulate organic polymeric materials such as finely comminuted water insoluble synthetic polymers. When present, such fillers should not exceed about 30% wt. of the compressed solid block composition, although generally lesser amounts are usually effective.

Preferably the compressed solid block of the invention includes silica. Silica has been observed to aid in the controlling the rate of dissolution of the compressed solid blocks of the invention.

The compressed solid block composition and treatment blocks formed therefrom may include one or more further processing aids. For example, the solid block composition may also include other binding and/or plasticizing ingredients serving to assist in the manufacture thereof, for example, polypropylene glycol having a molecular weight from about 300 to about 10,000 in an amount up to about 20% by weight, preferably about 4% to about 15% by weight of the mixture may be used. The polypropylene glycol reduces the melt viscosity, acts as a demolding agent and also acts to plasticize the block when the composition is prepared by a casting process. Other suitable plasticizers such as pine oil fractions, d-limonene, dipentene and the ethylene oxide-propylene oxide block copolymers may be utilized. Other useful processing aids include tabletting lubricants such as metallic stearates, stearic acid, paraffin oils or waxes or sodium borate which facilitate in the formation of the treatment blocks in a tabletting press or die.

One advantageously utilized processing aid is a diester constituent which may be represented by the following structure:

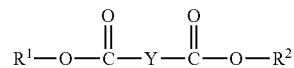

wherein:
$R^1$ and $R^2$ can independently be $C_1$-$C_6$ alkyl which may optionally substituted,
Y is $(CH_2)_x$, wherein x is 0-10, but is preferably 1-8, and while Y may be a linear alkyl or phenyl moiety, desirably Y includes one or more oxygen atoms and/or is a branched moiety.

Exemplary diester constituents include the following diester compounds according to the foregoing structure: dimethyl oxalate, diethyl oxalate, diethyl oxalate, dipropyl oxalate, dibutyl oxalate, diisobutyl oxalate, dimethyl succinate, diethyl succinate, diethylhexyl succinate, dimethyl glutarate, diisostearyl glutarate, dimethyl adipate, diethyl adipate, diisopropyl adipate, dipropyl adipate, dibutyl adipate, diisobutyl adipate, dihexyladipate, di-$C_{12-15}$-alkyl adipate, dicapryl adipate, dicetyl adipate, diisodecyl adipate, diisocetyl adipate, diisononyl adipate, diheptylundecyl adipate, ditridecyl adipate, diisostearyl adipate, diethyl sebacate, diisopropyl sebacate, dibutyl sebacate, diethylhexylsebacate, diisocetyl dodecanedioate, dimethyl brassylate, dimethyl phthalate, diethyl phthalate, dibutyl phthalate.

Preferred diester constituents include those wherein Y is —$(CH_2)_x$— wherein x has a value of from 0-6, preferably a value of 0-5, more preferably a value of from 1-4, while $R^1$ and $R^2$ are $C_1$-$C_6$ alkyl groups which may be straight chained alkyl but preferably are branched, e.g, iso- and tert-moieties. Particularly preferred diester compounds are those in which the compounds terminate in ester groups.

A further advantageously utilized processing aid is a hydrocarbon solvent constituent. The hydrocarbon solvents are immiscible in water, may be linear or branched, saturated or unsaturated hydrocarbons having from about 6 to about 24 carbon atoms, preferably comprising from about 12 to about 16 carbon atoms. Saturated hydrocarbons are preferred, as are branched hydrocarbons. Such hydrocarbon solvents are typically available as technical grade mixtures of two or more specific solvent compounds, and are often petroleum distillates. Nonlimiting examples of some suitable linear hydrocarbons include decane, dodecane, decene, tridecene, and combinations thereof. Mineral oil is one particularly preferred form of a useful hydrocarbon solvent. Further preferred hydrocarbon solvents include paraffinic hydrocarbons including both linear and branched paraffinic hydrocarbons. The former are commercially available as NORPAR solvents (ex. ExxonMobil Corp.) while the latter are available as ISOPAR solvents (ex. ExxonMobil Corp.) Mixtures of branched hydrocarbons especially as isoparaffins form a further particularly preferred form of a useful hydrocarbon solvent of the invention. Particularly useful technical grade mixtures of isoparaffins include mixtures of isoparaffinic organic solvents having a relatively narrow boiling range. Examples of these commercially available isoparaffinic organic solvents include ISOPAR C described to be primarily a mixture of $C_7$-$C_8$ isoparaffins, ISOPAR E described to be primarily a mixture of $C_8$-$C_9$ isoparaffins, ISOPAR G described to be primarily a mixture of $C_{10}$-$C_{11}$ isoparaffins, ISOPAR H described to be primarily a mixture of $C_{11}$-$C_{12}$ isoparaffins, ISOPAR J, ISOPAR K described to be primarily a mixture of $C_{11}$-$C_{12}$ isoparaffins, ISOPAR L described to be primarily a mixture of $C_{11}$-$C_{13}$ isoparaffins, ISOPAR M described to be primarily a mixture of $C_{13}$-$C_{14}$ isoparaffins, ISOPAR P and ISOPAR V described to be primarily a mixture of $C_{12}$-$C_{20}$ isoparaffins.

When present such further processing aids are typically included in amounts of up to about 30% by weight, preferably to 20% wt. of the solid block composition, although generally lesser amounts are usually effective.

Optionally but in some cases, preferably one or more of the foregoing constituents may be provided as an encapsulated, particularly a microencapsulated material. That is to say, quantities of one or more constituents are provided covered or encapsulated in an encapsulating material. Methods suitable for such an encapsulation include the customary methods and also the encapsulation of the granules by a melt consisting e.g. of a water-soluble wax, coacervation, complex coacervation and surface polymerization. Non-limiting examples of useful encapsulating materials include e.g. water-soluble, water-dispersible or water-emulsifiable polymers and waxes. Advantageously, reactive chemical constituents, particularly the fragrance composition when present, may be provided in an encapsulated form so to ensure that they do not prematurely degrade during processing of the constituents used to form the compressed solid block composition and that they are retained with minimal degradation in the compressed solid block composition prior to their use. The use of water soluble encapsulating material is preferred as such will release the one or more chemical constituents when the compressed solid block composition is contacted with water supplied either in the cistern or in the toilet bowl.

Ideally the compressed solid blocks exhibit a density greater than that of water which ensures that they will sink when suspended in a body of water, e.g., the water present within a cistern. Preferably the treatment blocks formed from the solid block composition exhibit a density in excess of about 1 g/cc of water, preferably a density in excess of about 1.5 g/cc of water and most preferably a density of at least about 2 g/cc of water.

While the mass of the compressed solid blocks may vary, and amount of up to an including 500 grams may be practiced, generally the mass of the compressed solid block compositions do not exceed about 150 grams. Advantageously the mass of the compressed solid blocks is between about 20 and 100 grams. It is appreciated that compressed solid blocks having great mass should provide a longer useful service life of the cageless lavatory dispensing devices, with the converse being equally true.

The compressed solid blocks according to the present invention may also be provided with a coating of a water-soluble film, such as polyvinyl acetate following the formation of the treatment blocks from the recited solid block composition. Such may be desired for improved handling, however such is often unnecessary as preferred embodiments of the compressed blocks exhibit a lower likelihood of sticking to one another following manufacture than many prior art treatment block compositions.

It will be appreciated by those of ordinary skill in the art that several of the components which are directed to provide a chemical composition can be blended into one chemical composition with the additional appreciation that potential blending of incompatible components will be avoided. For example, those of ordinary skill in the art will appreciate that certain anionic surfactants may have to be avoided as some may be incompatible with certain sanitizing agents and/or certain anti-lime scale agents mentioned herein. Those of ordinary skill in the art will appreciate that the compatibility of the anionic surfactant and the various sanitizing and anti-limescale agents can be easily determined and thus incompatibility can be avoided in the situations.

The compressed solid blocks may be formed of a single chemical composition, or may formed of two (or more) different chemical compositions which may be provided as separate regions of a solid block, such as a first layer of a solid block consisting of a first chemical composition, alongside a second layer of a the solid block consisting of a second chemical composition which is different than the first chemical composition. The block may also be formed of two or more separate blocks which are simply layered or otherwise assembled, without or without the use of an adhesive. Further layers of still further different chemical compositions may also be present. Such solid blocks formed having two or more discrete layers or regions of, respectively, two or more different chemical compositions may be referred to as composite blocks.

Any form of the compressed solid blocks may also be provided with a coating film or coating layer, such as a water soluble film which is used to overwrap the chemical composition provided in the device which film provides a vapor barrier when dry, but which dissolves when contacted with water. Alternately the compressed solid blocks may be oversprayed or dipped into a bath of a water soluble film forming constituent, and thereafter removed and thus allowing the water soluble film forming constituent to dry and form a coating layer on the compressed solid block.

Exemplary materials which may be used to provide such a coating on some or all of the surfaces of the compressed solid block compositions include one or more of the following: Rhodasurf TB-970 described by its supplier to be a tridecyl alcohol having a degree of ethoxylation of approximately 100 having an HLB of 19, and exhibiting a melting point in the range of 52-55° C.; Antarox F-108 which is described to be an EO-PO block copolymer having a degree of ethoxylation of approximately 80% and having a melting point in the range of 54-60° C.; further materials including those identified as Pluriol Z8000, and Pluriol E8000 which are believed to be optionally substituted, high molecular weight polyethylene glycols ("PEG") having a sufficiently high molecular weight such that they have a melting point of at least 25° C., preferably a melting point of at least about 30° C. may also be used. Other water soluble materials, desirably those which have a melting point in the range of about 30-70° C., and which may be used to provide a water soluble or water dispersible coating on the compressed solid blocks are also contemplated to be useful, especially synthetic or naturally occurring waxy materials, and high molecular weight polyalkylene glycols, especially polyethylene glycols. Certain of these coating materials may be surfactants. Generally such materials may be provided as a dispersion in water, an organic solvent or in an aqueous/organic solvent, but preferably are used as supplied from their respective supplier and are heated to at least their melting points in order to form a liquid bath. Conveniently, the compressed solid blocks affixed to the plate of a hanger are then conveniently dipped into the said bath, thereby providing a coating layer to the compressed solid blocks. Alternately, the coating materials may be sprayed, brushed on or padded onto at least part of the surfaces of the previously formed compressed solid blocks.

The application of a water soluble film or coating is preferred in certain embodiments of the invention as the surface film may facilitate the handling of the blocks during packaging and storage prior to use of the cageless lavatory dispensing devices. Further, the application of a water soluble film or coating is preferred as certain water soluble film former compositions may impart a desirable surface gloss to the compressed lavatory blocks.

Preferably the compressed solid block compositions useful in the cageless lavatory dispensing devices include those which comprise at least one surfactant, preferably at least one anionic or nonionic surfactant.

Exemplary compositions which can be used to form the compressed solid blocks of the present invention are shown in the following table below; the amounts indicates are in % wt. of the "as supplied" constituent used to form an example block compositions, labeled A through F.

| Component | A | B | C | E | F |
|---|---|---|---|---|---|
| Dodecyl Benzene Sulfonate Na[1] | 25 | 10 | 40 | 35 | 35 |
| Alfa Olefine Sulfonate Na[2] | 25 | 10 | 5 | 32 | 32 |
| Lauryl monoethanolamide[3] | 10 | 8 | 5 | 2 | 5 |
| Sodium Lauryl Ether Sulfate[4] | 10 | — | — | 4.5 | 5 |
| Pluronic 68[5] | 10 | — | — | 3 | — |
| Na Sulfate | 20 | — | — | 21.5 | 21 |
| Pluronic 87 or 88[6] | — | 70 | 50 | — | — |
| Alcohol ethoxylate $C_9$-$C_{11}$ 6EO[7] | — | 2 | — | — | — |
| Silica | — | — | — | 2 | 2 |

[1]Dodecyl Benzene Sulfonate Sodium (80-90% active) -- anionic
[2]Alpha Olefin Sulfonate Sodium -- anionic
[3]Lauryl Monoethanolamide -- non-ionic
[4]Sodium Lauryl Ether Sulfate (70% active) -- anionic
[5]Polyoxyethylene (160) polyoxypropylene (30) glycol - non-ionic
[6]Pluronic 87 $E_{61}$ $P_{41.5}$ $E_{61}$ -- Molecular Weight 7700 -- HLB 24 -- non-ionic
Pluronic 88 $E_{98}$ $P_{41.5}$ $E_{98}$ -- Molecular Weight 10800 -- HLB 28-- non-ionic
[7]Alcohol ethoxylate $C_9$-$C_{11}$ 6EO -- non-ionic Further exemplary bleach containing compositions which can be used to form the compressed solid blocks of the present invention include compositions indicated on the next table having the general ranges as follows:

| | % w/% w |
|---|---|
| alpha olefin sulfonate | 0-35 |
| Sodium lauryl ether sulfate | 3.0-6.0 |
| Bleaching agent (e.g., DCCNa or Hydantoin) | 0.5-25 |
| Lauryl monoethanolamide | 2.0-5.0 |
| Dodecyl benzene sulfonate Na | 50-70 |
| Na sulfate anhydrous | 15-25 |
| Silica | 1.0-2.0 |

Further exemplary preferred embodiments of blocks which are useful as compressed solid blocks of the present invention include those which comprise:

10-35% wt., preferably 15-30% wt. of an alpha olefin sulfonate anionic surfactant;

10-35% wt., preferably 15-30% wt. of a linear monoethanolamide;

5-50% wt., preferably 15-35% wt. of a linear dodecylbenzene sulfonate anionic surfactant;

5-50% wt., preferably 20-35% wt. of sodium sulfate 0.1-15% wt., preferably 0.5-5% wt. of silica 0.1-25% wt., preferably 1-10% wt. sodium lauryl ether sulfate optionally to 40% wt. further additive constituents, including but not limited to further surfactants, fillers, binders, fragrances, processing aids such as lubricants and tabletting aids, bleaches, sanitizing compositions and the like.

Yet further exemplary compositions which include a bleach constituent which find use as compressed solid blocks of the present invention include those recited on the following tables, and labeled as G through N:

| | G | H | I | J | K | L |
|---|---|---|---|---|---|---|
| dodecylbenzene sulfonate, sodium salt (80%) | 27.0 | 22.0 | 32.0 | 35.00 | 37.8 | 32.0 |
| sodium C14/C16 olefin sulfonates (80%) | 15.0 | 20.0 | 15.0 | 22.0 | 23.62 | 20.0 |
| silica | 2.0 | 2.0 | 2.0 | 2.0 | 1.89 | 2.0 |
| lauramide monoethanol amide (98%) | 30.0 | 30.0 | 25.0 | 15.00 | 12.28 | 20.0 |
| sodium sulfate | 20.5 | 20.5 | 20.5 | 20.50 | 18.90 | 20.5 |
| dichlorocyanurate dihydrate, sodium salt (56% bleach) | 2.5 | 2.5 | 2.5 | 2.4 | 2.41 | 2.5 |
| paraffinic hydrocarbons | 3.0 | 3.0 | 3.0 | 3.1 | 3.09 | 3.0 |

| | M | N | O |
|---|---|---|---|
| dodecylbenzene sulfonate, sodium salt (80%) | 35.0 | 37.0 | 32.0 |
| sodium C14/C16 olefin sulfonates (80%) | 22.0 | 25.0 | 20.0 |
| silica | 2.0 | 2.0 | 2.0 |
| lauramide monoethanol amide (98%) | 15.0 | 10.0 | 20.0 |
| sodium sulfate | 20.5 | 20.5 | 18.5 |
| dichlorocyanurate dihydrate, sodium salt (56% bleach) | 2.5 | 2.5 | 2.5 |
| paraffinic hydrocarbons | 3 | 3 | 5 |

The identity of the constituents used to form the foregoing compressed solid blocks G-O are identified more specifically on the following table.

| | |
|---|---|
| dodecylbenzene sulfonate, sodium salt (80%) | anionic surfactant, dodecylbenzene sulfonate, 80% wt. actives |
| sodium C14/C16 olefin sulfonates (80%) | anionic surfactant, sodium C14/C16 olefin sulfonates, 80% wt. actives |
| silica | filler anhydrous silica, 100% wt. actives. |

-continued

| | |
|---|---|
| lauramide monoethanol amide (98%) | solubility control agent, lauramide monoethanol amide, 98% wt. actives |
| sodium sulfate | diluent, sodium sulfate, 100% wt. actives |
| dichlorocyanurate dihydrate, sodium salt (56%) | bleach constituent, dichlorocyanurate dihydrate, sodium salt, 56% wt. bleach actives |
| Isopar M | hydrocarbon solvent, isoparaffinic organic solvents, 100% wt. actives |
| mineral oil | Hydrocarbon solvent, mineral oil, 100% wt. actives |
| paraffinic hydrocarbons | Hydrocarbon solvent, white paraffin oil, 100% wt. actives |

Still further exemplary compositions which include diisopropyl adipates which find use as compressed solid blocks of the present invention include those recited on the following tables, and labeled as P through W:

| | P | Q | R | S |
|---|---|---|---|---|
| dodecylbenzene sulfonate, sodium salt (80%) | 55.85 | 58.85 | 62.51 | 62.51 |
| silica | 2.41 | 2.41 | 2.56 | 2.56 |
| lauramide monoethanolamide (98%) | 6.01 | 6.01 | 6.38 | 6.38 |
| sodium sulfate | 12 | 12 | 12.75 | 12.75 |
| dichlorocyanurate dihydrate, sodium salt (56%) | 14.63 | 14.63 | 9.32 | 9.32 |
| diisopropyl adipate | 6.1 | 6.1 | 6.48 | 6.48 |

| | T | U | V | W |
|---|---|---|---|---|
| dodecylbenzene sulfonate, sodium salt (80%) | 58.61 | 67.27 | 69.25 | 70.83 |
| silica | 2.40 | 1.91 | 1.96 | 2.01 |
| lauramide monoethanolamide (98%) | 5.98 | 4.74 | 4.88 | 4.99 |
| sodium sulfate | 11.95 | 17.37 | 17.88 | 18.29 |
| dichlorocyanurate dihydrate, sodium salt (56%) | 14.6 | 4.98 | 2.41 | 0.55 |
| diisopropyl adipate | 6.46 | 3.73 | 3.61 | 3.33 |

The identity of the constituents used to form the foregoing compressed solid blocks labeled P through W are identified more specifically on the following table:

| | |
|---|---|
| dodecylbenzene sulfonate, sodium salt (80%) | anionic surfactant, dodecylbenzene sulfonate, 80% wt. actives |
| silica | anhydrous silica, 100% wt. actives. |
| lauramide monoethanolamide (98%) | solubility control agent, lauramide monoethanolamide, 98% wt. actives |
| sodium sulfate | diluent, sodium sulfate, 100% wt. actives |
| dichlorocyanurate dihydrate, sodium salt (56%) | bleach constituent, dichlorocyanurate dihydrate, sodium salt, 56% wt. bleach actives |
| diisopropyl adipate | diester constituent, diisopropyl adipate, 100% wt. actives |

Yet further exemplary compositions which include paraffinic hydrocarbon solvents or mineral oil which find use as compressed solid blocks of the present invention include those recited on the following tables, and labeled as AA through AK:

| | AA | AB | AC | AD | AE |
|---|---|---|---|---|---|
| dodecylbenzene sulfonate, sodium salt (80%) | 65.8 | 65.8 | 65 | 64.17 | 69.25 |
| silica | 2.69 | 2.69 | 2.66 | 2.63 | 1.96 |
| lauramide monoethanolamine (98%) | 6.72 | 6.72 | 6.64 | 6.55 | 4.88 |
| sodium sulfate | 13.42 | 13.42 | 13.26 | 13.09 | 17.88 |
| dichlorocyanurate dihydrate, sodium salt (56% bleach) | 8.89 | 8.89 | 8.78 | 9.57 | 2.41 |
| Isopar M | 2.47 | 2.47 | — | — | — |
| mineral oil | — | — | 3.66 | 3.99 | 3.61 |

| | AF | AG | AH | AI | AJ | AK |
|---|---|---|---|---|---|---|
| dodecylbenzene sulfonate, sodium salt (80%) | 70.83 | 69.25 | 69.25 | 69.25 | 70.83 | 68.31 |
| silica | 2.01 | 1.96 | 1.96 | 1.96 | 2.01 | 2.90 |
| lauramide monoethanolamine (98%) | 4.99 | 4.88 | 4.88 | 4.88 | 4.99 | 4.88 |
| sodium sulfate | 18.29 | 17.88 | 17.88 | 17.88 | 18.29 | 17.88 |
| dichlorocyanurate dihydrate, sodium salt (56% bleach) | 0.55 | 2.41 | 2.41 | 2.41 | 0.55 | 2.41 |
| Isopar M | 3.33 | 3.61 | 3.61 | — | — | 3.61 |
| mineral oil | — | — | — | 3.61 | 3.33 | — |

The identity of the constituents used to form the foregoing blocks AA through AK are identified more specifically on the following table:

| | |
|---|---|
| dodecylbenzene sulfonate, sodium salt (80%) | anionic surfactant, dodecylbenzene sulfonate, 80% wt. actives |
| silica | filler anhydrous silica, 100% wt. actives. |
| lauramide monoethanolamide (98%) | solubility control agent, lauramide monoethanolamide, 98% wt. actives |
| sodium sulfate | diluent, sodium sulfate, 100% wt. actives |
| dichlorocyanurate dihydrate, sodium salt (56%) | bleach constituent, dichlorocyanurate dihydrate, sodium salt, 56% wt. bleach actives |
| Isopar M | hydrocarbon solvent, isoparaffinic organic solvents, 100% wt. actives |
| Mineral oil | Hydrocarbon solvent, mineral oil, 100% wt. actives |

Yet further and particularly preferred embodiments of compressed solid blocks and their compositions include those which are recited on Table 1.

The manufacture of the cageless lavatory dispensing device first contemplates mixing the constituents of the block composition into a generally homogenous mass such as by noodling, as well as by plodding, but preferably by extruding, and thereafter forming a "preform" from a measured quantity of the homogenous mass. Usually all of the solid ingredients are mixed in any suitable blending equipment followed by the addition of liquid ingredients under blending conditions. In an extrusion process a mixture of the chemical constituents used to ultimately form the compressed solid block composition is made, followed by extrusion of this mixture into a rod or bar form which is then cut into appropriately sized pieces or blocks which are to be used in the subsequent, separate compression process. These pieces or blocks of extrudate are the preforms. When the compressed solid block is formed from a single preform it is required to provide a cavity, channel or recess within the preform of suitable dimensions to accept a part of the hanger, advantageously a plate. Conveniently a channel may be provided by cutting a slot in the preform of sufficient depth and width such that the plate may be fully inserted into the interior of the preform prior to the subsequent compression process. The channel may be cut, or carved such as by the use of a saw, or other cutting device which will either split or shape the preform adequately to provide such a suitable sized channel or recess. Alternately a channel may be providing by extruding through a die which includes a blade or other cutter means which extends into the open cross-section of the die such that as the extrudate exits the die, it is provided with such a channel which partially splits the extrudate into the legs of a "V", which remain attached however at the base of each leg. Such a channel may extend across the length of the preform and through the ends thereof. Alternately, subsequent to extrusion a tool such as a plunging blade may be used to partially split a portion of a preform in order to provide a cavity or slot which is of sufficient width and depth to accommodate at least the plate of the hanger. Such a cavity formed by such blade typically does not extend across the length of the preform nor through the ends thereof.

In a next process step, the plate of a hanger is inserted within the interior of the channel or cavity such that the plate is preferably wholly encased within the interior of the preform. Preferably also the hanger extends outwardly from the preform at an angle which is approximately perpendicular to, more specifically $90°\pm/-10°$, preferably $90°\pm/-5°$ with respect to tangent of the surface from which point the hanger extends outwardly therefrom. Such ensures that consistent loading and proper weight distribution of the hook, and proper placement of the cageless device in the sanitary appliance, especially a toilet is maintained.

Advantageously the cavity, channel or recess is essentially planar in configuration and is situated within the compressed solid block such that the plate is not placed within the symmetrical center or the mid-plane of the said block but rather is positioned to be parallel to a face or surface of the block such that the plate is positioned within a plane which is at a distance between 10%-80%, preferably 30%-70% of the distance between the face of surface of the said block, and the symmetrical center or the mid-plane of the said block. Further preferably, the hanger and the compressed solid block is so positioned with respect to one another that the face of the said block nearest to the embedded plate is on the side opposite of the hook end of the hanger.

Alternately the extrudate may be of an alternate configuration, e.g., a rectangular, square or oblate cross-sectional configuration, which is formed into preforms. A cavity, channel or recess within the preform is not required as in an alternative process to the above, two or more discrete preforms are used together with then plate of the hanger positioned intermediate two adjacent preforms which are subsequently compressed.

The preform comprising the hanger is then compressed in a die which imparts the final shape to the compressed solid block. This compression step may be practiced as a single compression operation or as a series of compression steps, i.e., with two or more stamping or compression operations. Advantageously the preform(s) are positioned in a die such that the plane of the plate of the hanger is parallel to the opposing major faces of the compression dies which are brought together. Optionally a mold release agent, such as a waxy material or an oil, such as a paraffin oil or mineral oil may be applied to one or more surfaces of the die. Such may improve the ease of release of the compressed solid block, and/or aid in the formation of a smooth external surface to the compressed solid block. Following compression the compressed solid block are affixed onto the hanger, and may be removed from or ejected from the die. The cageless delivery device thus formed is ready for use.

As noted previously the preform used to form the compressed solid blocks may be formed from a plurality of preforms which are conveniently layered in register, with the hanger inserted between two preforms in the orientation as described above. For example, two or more physically separate preforms may be layered in register to form a laminated compressed solid block. Such may be desired when it is intended that the compressed solid block be formed from two or more masses having different chemical compositions. For example, it is contemplated that the compressed solid mass may be formed from a first preform having a first chemical composition, compressed to a second preform having a second chemical composition which is different than the first chemical composition. By way of non-limiting example, the first preform may be of a first color, while the second preform may be of different, second color so that when compressed the preforms are compressed to form a single compressed solid block having two different colored layers. Of course, three or more preforms may be compressed to form a single compressed block. Again the chemical compositions of the first, second and third preforms may be of the same, similar or of different compositions.

During the compression step, several simultaneous technical effects occur. The block compositions are densified due to the compression, and concurrently the embedded hanger is sealed and mechanically anchored within the interior of the block. Preferably the density of the compressed solid block as at least 1% greater, preferably at least 1.5% greater than the density of the density of the extrudate. Preferably the density of the compressed solid block is at least 2%, more preferably at least 3% greater than the density of the preform or extrudate from which it is formed. Additionally during the compression step, the channel, slot or recess which had been formed to accept the hanger is sealed to form a smooth surface. Still further the exterior surface of the block composition takes on the volume configuration and the surface shape of the die. Such is particularly advantageous when the interior surface of the die is smooth walled which will, in preferred embodiments, impart a smooth exterior surface to the compressed solid block.

In certain particularly preferred embodiments the compressed solid blocks of the present invention weigh from 15 to 150 grams, preferably from about 20 to about 75 grams. The blocks are typically oblate in shape, having a length of from about 1 to about 4 inches and having a thickness of from about 0.5-1.5 inches.

The service life of the compressed solid blocks should be from about 10 to about 90 days, based on 12 flushes per day. Preferably the service life of the compressed solid blocks is at least about 14 days when installed on the rim of a toilet bowl such that the said block is positioned adjacent to the sloping interior sidewall of the toilet bowl and is subjected to between 6-12 flushes per day. Preferably the temperature of the water which is flushed is in the range of 16-24° C. The length of life of the compressed solid blocks will of course depend on a variety of factors including product formulation, water temperature, tank size, the number of flushes over the period of use and the volume of the water which contacts the compressed solid blocks.

Various configurations of the cageless lavatory dispensing device, including certain particularly preferred embodiments, are depicted on the following figures. In the accompanying figures, like elements are indicated using the same numerals throughout the figures.

FIG. 1 depicts a hanger 10 comprising a hook end 20 comprising an end member 12 flexibly attached to a top member 14 as well as part of the stalk 16. Depending from the end of the stalk 16 distally from the hook end 20 is a plate 30. As can be seen from the perspective view provided by FIG. 1, the plate itself is generally rectangular in configuration, and it is coplanar with the ribbon-type or strip-type configuration and construction of both the stalk 16 and hook end 20. The plate 30 has a width dimension "W1" as well as a height dimension "H1" and as depicted, desirably the width is greater than the height. As is visible from the figure, the hanger 10 is generally symmetrical about a center line "CL" which is drawn with respect to the midline of the stalk 16. The center line does not exist as an actual element of the device but is illustrated for the sake of convenient reference. While not illustrated with sufficient particularity in the figure, it is of course understood that the plate, stalk 16 and the hook end 20 all have a thickness which may be consistent throughout, or which can vary.

FIG. 2 depicts a side view of a further embodiment of the hanger 10 of FIG. 1. As is more clearly seen in this figure, the hook end 20 is formed from first and second elements 12, 14 and part of the stalk 16. Depending from the stalk 16 is the plate 30. In this embodiment the plate 30 has a thickness "T1" which is greater than the thickness "T2" of the stalk 16 and the hook end 20. Of course, it will be understood that each of the hook end, stalk, and plate can have different thicknesses or can all share the same thickness as illustrated in FIG. 1.

FIG. 3 depicts a further embodiment of a hanger 10 according to the invention, in which the hook end 20 is a flexible element. As can be seen from the figure, the hook end is comprised of an end member 12 flexibly connected to a top element 14 which in turn is flexibly connected to the stalk 16. At the end opposite the hook end, depends the plate 30. With regard to the hook end, as can be seen, at the terminal end of the end member 12 is seen a broadened region which is referred to as a "pad" 15. The pad region is of the same thickness as the end member 12, but is slightly broader. The width of the pad end 15 is greater than the width of the end member 12. This increased width is sometimes useful to stabilize the hook end of the cageless lavatory dispensing device when suspended upon part of a sanitary appliance. As is further visible from FIG. 3, the plate 30 is substantially planar in configuration has a width W1 as well as height H1 and is symmetric around the center line CL of the stalk 16. The plate has a generally linear bottom edge 39 at opposite ends thereof to generally straight end walls 36, 38 which end walls proceed and extend to the stalk 16 via sloping top walls 32, 34.

FIG. 4 depicts the hanger 10 of FIG. 3 in both a "folded" as well as in an "unfolded" configuration.

As seen from the solid line elements depicted on FIG. 4, the hanger 10 on the folded configuration illustrates, that when the hook end and the stalk are untensioned, the hook end 20 is retained in a closed configuration. In the unfolded configuration, as depicted by the elements depicted in a broken line format, the end member 12' and the pad 15' are extended away from the stalk 16 and are more distantly positioned with respect to the stalk than in the prior, folded configuration. Typically, this also causes a degree of translation of the top element 14' which may extend down to, include a portion of the stalk 16' as well. When made of a flexible material, in the unfolded configuration as depicted in FIG. 4, the elastic bias of the material of construction, such as a polymer, tends to cause the hook end to seek to return to the folded configuration. However, when placed about the rim of a portion of a sanitary device, i.e. a toilet bowl, this action causes the hook end to impart a degree of gripping to that portion of the rim upon which it is mounted. This is turn helps retain the relative position of the hook end, as well as that of the cageless lavatory dispensing device until repositioned, or removed by a consumer.

FIG. 5 depicts a still further embodiment of a hanger 10. In this embodiment, the hanger includes a coiled hook end 20 comprised of the end member 12, the second element 13 and a top element 14 which is in a compressed, coiled arrangement thus making it particularly convenient to include in a consumer package. The top end of the top element 14 extends to a stalk 16 having at its opposite end a depending plate 30. In this configuration, the plate 30 is oblate in shape and is generally symmetrical about a center line (CL). The plate has a width dimension (W1) as well as a height dimension (H1). Further, the plate illustrates that it can be produced with perforations passing therethrough. Here, two similarly shaped, generally triangular passages 33, 33' are provided. As has been discussed previously in the specification, while it is contemplated that the plate of the hanger may include one or more perforations passing there through, for reasons observed although not yet fully understood by the applicants, it is believed that the use of plates having such perforations passing there through are to be preferably avoided as such may undesirably reduce the service life of the cageless lavatory dispensing device.

Figure 6:
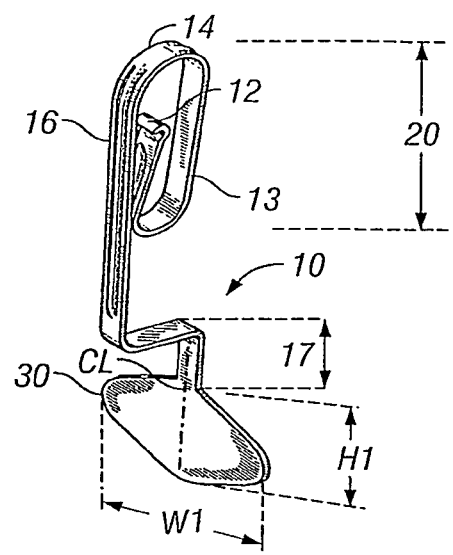
FIG. 6 depicts a further embodiment of a hanger.

FIG. 6 depicts a still further embodiment of a hanger 10 according to the invention. As is shown, the hanger includes a hook end 20 which is comprised of the end member 12, flexibly connected to element 13, which is in turn flexibly connected to a top element 14, which in turn is flexibly connected to a part of the stalk 16. The opposite end of the stalk terminates in a generally oblate shaped plate 30 having a width dimension (W1), a height dimension (H1) wherein the plate is generally symmetrically about the center line (CL) as depicted in the dotted line drawn on FIG. 6. Whereas the hanger is depicted in a folded or otherwise coiled configuration, it is to be understood that the hook end can be extended by a user of the hanger and the cageless lavatory dispensing device to reconfigure said hook end 20 to form a hook end which can be used to suspend the hanger and the cageless lavatory dispensing device upon a part of a sanitary device particularly a toilet bowl rim. The embodiment according to FIG. 6 also illustrates that, according to preferred embodiments, the plate 30 is substantially planar and as is shown in FIG. 6, it is of generally uniform thickness. The embodiment depicted in FIG. 6 is preferred in that the hook end is particularly well coiled when in its folded configuration, but when uncoiled or in its unfolded configuration, provides a significant degree of tension which is useful in retaining the respective position of the cageless lavatory dispensing device when installed upon a sanitary appliance, particularly when the hook is affixed on a part of a toilet bowl rim. Furthermore, FIG. 6 depicts that that embodiment also includes a bent neck 17 formed as part of the stalk 16 and immediately adjacent to the region of the plate 30 which is connected to the stalk 16. As depicted, the bent neck 17 positions the plate 30 at a position which is rearward of the major portion of the stalk 16 but retains the plate 30 as being generally parallel thereto. This positioning rearward of the major part of the stalk 16 is beneficial as ultimately, it acts to also thereby position the compressed solid block enrobing the plate 30 such that when mounted upon a toilet bowl, the compressed solid block is in contact with, or is in very proximity to the interior sloping side wall of a toilet bowl. Such positioning is advantageous in that it ensures that the compressed solid block remains in the flow path of the flush water throughout the useful service life of the cageless lavatory dispensing device.

Figure 7:
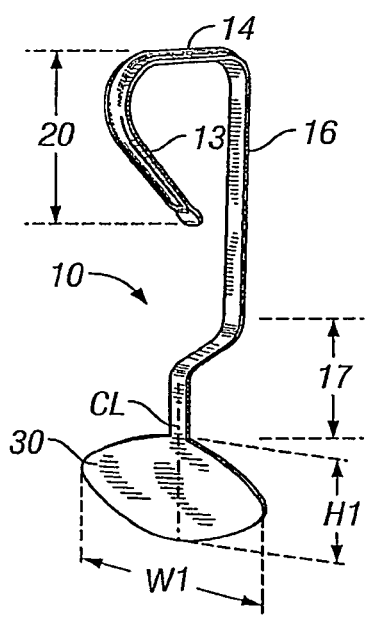
FIG. 7 depicts a further embodiment of a hanger.

FIG. 7 illustrates a yet further embodiment of a hanger 10 according to the invention. As is shown, the hanger includes a hook end 20 comprising an element 13, flexibly connected to a top element 14, which in turn is flexibly connected to a part of the stalk 16. The stalk 16 extends downwardly through a bent neck section 17 and terminates in a generally oblate shaped plate 30 having a width dimension (W1), a height dimension (H1) wherein the plate is generally symmetrically about the center line (CL) as depicted in the dotted line drawn on FIG. 6. Whereas the hanger is depicted in a folded configuration, it is to be understood that the hook end can be extended by a user of the hanger and the cageless lavatory dispensing device to flex and open said hook end 20 suspend the hanger and the cageless lavatory dispensing device upon a part of a sanitary device, particularly a toilet bowl rim. The embodiment according to FIG. 7 also illustrates that, according to preferred embodiments, the plate 30 is substantially planar and as is shown in FIG. 7, it is of generally uniform thickness. The embodiment depicted in FIG. 7 depicts that that embodiment also includes a bent neck section 17 formed as part of the stalk 16 and immediately adjacent to the region of the plate 30 which depends from the stalk 16. As illustrated, the bent neck 17 positions the plate 30 at a position which is rearward of the major portion of the stalk 16 but retains the plate 30 as being generally parallel thereto. This positioning rearward of the major part of the stalk 16 is beneficial as ultimately, it acts to also thereby position the compressed solid block enrobing the plate 30 such that when mounted upon a toilet bowl, the compressed solid block is in contact with, or is in very proximity to the interior sloping side wall of a toilet bowl. Such positioning is advantageous in that it ensures that the compressed solid block remains in the flow path of the flush water throughout the useful service life of the cageless lavatory dispensing device.

Figure 8:
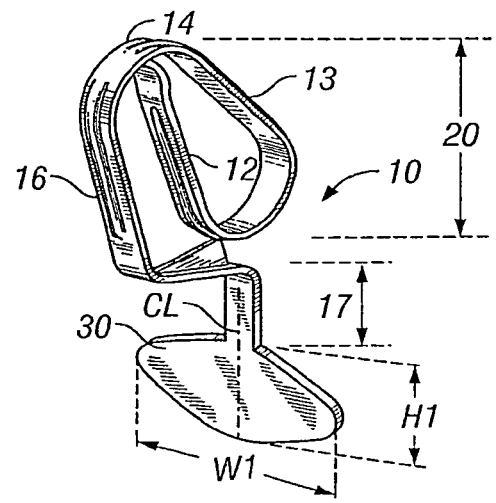
FIG. 8 depicts a further embodiment of a hanger.

FIG. 8 depicts a still further embodiment of a hanger 10 according to the invention. As is shown, the hanger includes a hook end 20 which is comprised of the end member 12, flexibly connected to element 13, which is in turn flexibly connected to a top element 14, which in turn is flexibly connected to a part of the stalk 16. The stalk extends downwardly through a neck section 17, and terminates at a generally oblate shaped plate 30 having a width dimension (W1), a height dimension (H1) wherein the plate is generally symmetrically about the center line (CL) as depicted in the dotted line drawn on FIG. 6. The illustrated embodiment includes a bent neck 17 which is angled, thereby configuring the major part of the stalk 16 to be non-parallel to the plane of the plate 30, but rather is angled with respect thereto. Whereas the hanger 20 is depicted in a folded or otherwise coiled configuration, it is to be understood that the hook end can be extended by a user of the hanger and the cageless lavatory dispensing device to reconfigure said hook end 20 to form a hook end which can be used to suspend the hanger and the cageless lavatory dispensing device upon a part of a sanitary device particularly a toilet bowl rim. The embodiment according to FIG. 8 illustrates that, according to preferred embodiments, the plate 30 is substantially planar and as is shown is of a generally uniform thickness. The embodiment depicted in FIG. 8 is preferred in that the hook end 20 is tightly coiled when in its folded configuration, but when uncoiled or in its unfolded configuration and suspended from a part of a lavatory appliance, provides a significant degree of tension which is useful in retaining the respective position of the cageless lavatory dispensing device when installed upon a sanitary appliance, particularly when the hook is affixed on a part of a toilet bowl rim. Furthermore, as seen the bent neck 17 positions the plate 30 at a position which is rearward of the major portion of the stalk 16 but retains the plate 30 as being generally parallel thereto. Such positioning of the plate rearward of the major part of the stalk 16 is beneficial as ultimately, it acts to also thereby position the compressed solid block enrobing the plate 30 such that when mounted upon a toilet bowl, the compressed solid block is in contact with, or is in very proximity to the interior sloping side wall of a toilet bowl. Such positioning is advantageous in that it ensures that the compressed solid block remains in the flow path of the flush water throughout the useful service life of the cageless lavatory dispensing device.

FIGS. 9A and 9B depict a hanger 10 comprising a hook end 20 comprising an end member 12 flexibly attached to a top member 14 as well as part of the stalk 16. Depending from the end of the stalk 16 distally from the hook end 20 is a plate 30. As can be seen from the perspective view provided by FIG. 1, the plate itself is generally planar and rectangular in configuration, and it is coplanar with the configuration and construction of both the stalk 16 and hook end 20. The plate 30 has a width dimension "W1" as well as a height dimension "H1" and as depicted, desirably the width is greater than the height. As is visible from the figure, the hanger 10 is generally symmetrical about a center line "CL" which is drawn with respect to the midline of the stalk 16. The center line does not exist as an actual element of the device but is illustrated for the sake of convenient reference. As is also visible in the figure, a portion of the stalk 16 is configured to extend rearwardly, namely in the direction of the hook end 20 to form a standoff section 80. In the embodiment depicted, the standoff section comprises a first stalk segment 82 which extends rearwardly from the stalk 16 to a peak point 86, and a second stalk segment 84 which extends rearwardly from the stalk 16 to the same peak point 86. As is visible in the depicted embodiment of FIG. 1. The stalk 16, first stalk segment 82, peak point 86, second stalk segment 84 and the plate 30 are all integrally formed as parts of the hanger 10. This is not required, but is preferred in certain embodiments as such requires no assembly subsequent to the initial fabrication of the hanger 10. As is also visible, the standoff section 80 is a conveniently formed by the shape of the hanger 10 to include the first stalk segment 82, second stalk segment 84 and intermediate peak point 86 which is formed by bends or other junctures between the respective segments and between the respective segments and the stalk 16 or plate 30. In the embodiment shown, the length of the first stalk segment 82 and the second stalk segment 84 of the standoff section 80 are of equal lengths. While not illustrated with sufficient particularity in the figure, it is of course understood that the plate, stalk 16 and the hook end 20 all have a thickness which may be consistent throughout, or which can vary.

FIG. 9B depicts a side view of the hanger of FIG. 9A. As is more clearly seen in this figure, the hook end 20 is formed from first and second elements 12, 14 and part of the stalk 16. In the embodiment shown, the length of the first stalk segment 82 and the second stalk segment 84 of the standoff section 80 are of different lengths, specifically the length of the first stalk segment 82 is greater than that of the second stalk segment 84. Depending from the stalk 16 is the plate 30. In this embodiment the plate 30 has a thickness "T1" which is equivalent to the thickness "T2" of the stalk 16 and the hook end 20. Of course, it will be understood that each of the hook end, stalk, and plate can have different thicknesses or can all share the same thickness as illustrated in FIG. 9A.

FIGS. 10A and 10B depicts a further embodiment of a hanger 10 according to the invention, in which the hook end 20 is a flexible element, and a standoff element 80 which is intermediate the hook end and the plate 30 of the hanger. The standoff element 80 extends rearwardly from a part of the stalk 16 in the same direction as the hook end 20 extends from the stalk 16. While the hook end is integrally formed with stalk 16 and is proximate to the plate 30 as is illustrated in the figures, it is to be understood that the standoff element 80 may be a discrete element which may be affixed to a part of the hanger 10, advantageously to a part of the stalk 16 by any suitable means. Inter alia, such means may be mechanical means such as interlocking elements such as cooperating snap-fittings and/or chemical means such as an adhesive or by welding or fusing of these elements. As can be seen from the figures, the hook end is comprised of an end element 12 flexibly connected to second hook element 13 which is in turn connected to a top element 14 which in turn is flexibly connected to the stalk 16. At the end of the stalk 16 opposite the hook end, viz, the distal end of the stalk depends the plate 30, here having an planar, oblate configuration. As is further visible from FIG. 3, the plate 30 is substantially planar in configuration has a width W1 as well as height H1 and is symmetric around the center line CL of the stalk 16. The plate 30 has a generally rectangular configuration and depends from the stalk 16 via an intermediate bent neck section 17 of the stalk 16.

While not specifically illustrated in FIGS. 10A and 10B it is to be understood that the hook end 20 of the hanger 10 is depicted in a first, "folded" configuration which permits for the hanger 10 to be compact and conveniently packaged. However, when at least the hook end 20 of the hanger 10 is fabricated of a flexible material, the elements of the hook end 20, especially the a end element 12 flexibly connected to second hook element 13 may be flexed to form the hook end 20 so that it may be placed about the rim of a portion of a sanitary device, i.e. a toilet bowl. Such elements form an articulated hook which may be extended from the stalk 16. This action imparts tension to the hook end 20 and also causes the hook end to 20 impart a degree of gripping to that portion of the rim upon which it is mounted. This is turn helps retain the relative position of the hook end, as well as that of the cageless lavatory device until repositioned, or removed by a consumer. At the same time however the peak point 86 of the standoff element 80 is adapted to contact a part of the sanitary appliance, typically a sidewall of a toilet bowl.

FIGS. 11A through 11G depict in various views an embodiment of a hanger 10 according to the invention which comprises a standoff section, both with and without the compressed solid block composition affixed to the plate 50.

Figure 11A:
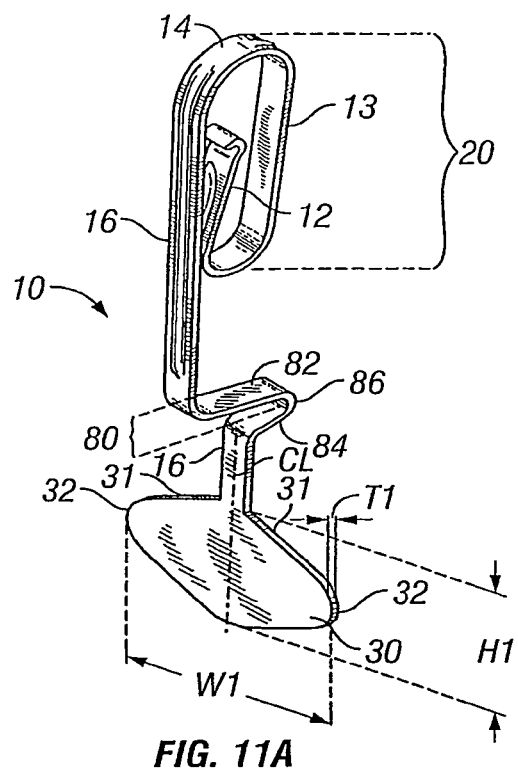
FIGS. 11A and 11G various views an embodiment of a hanger which comprises a standoff section, both with and without the compressed solid block composition affixed to the plate.

FIG. 11A depicts a one-piece hanger 10 formed of a flexible material, e.g., a thermoplastic polymer. The hanger 10 comprises a hook end 20 comprising a first hook element 12, a second hook element 13 and a top member 14 which in turn is connected to a downwardly extending stalk 16, which terminates in plate 30. Intermediate the hook end 20 and the plate 30, a portion of the stalk 16 is configured to extend rearwardly, namely in the direction of the hook end 20 to form a standoff section 80. As depicted, the standoff section comprises a first stalk segment 82 which extends rearwardly from the stalk 16 to a peak point 86, and a second stalk segment 84 which extends rearwardly from the stalk 16 to the same peak point 86. As is visible in the depicted embodiment of FIG. 11A the stalk 16, first stalk segment 82, peak point 86, second stalk segment 84 and the plate 30 are all integrally formed as parts of the hanger 10. Further as depicted, the length of the first stalk segment 82 and the second stalk segment 84 are unequal, with the former being greater than the latter. The plate 30 is a generally flat planar plate having a maximum width W1 which is at least 1.2 times the dimension of its maximum height H1. The plate 30 depends from a part of the stalk 16 and is a symmetrical about the center line "CL" of the stalk 16. The plate 30 also has a thickness T1, and as illustrated on the figure, has top edges 31 which are generally straight and are angled downwardly with respect to the stem 16. The top edges 31 continue to the region of the side vertices 32 of the plate 30 which are rounded. The plate 30 is also generally symmetrical about a line which would extend between the two side vertices 32 of the plate 30.

While not disclosed in the figure, it is to be understood that the hook end 20 is flexible and in the figures shown are in a folded configuration. However, the elements of the hook end may be readily unfolded by a consumer so to adapt the hanger 10 to be suspended upon a part of a sanitary appliance.

Figure 11B:
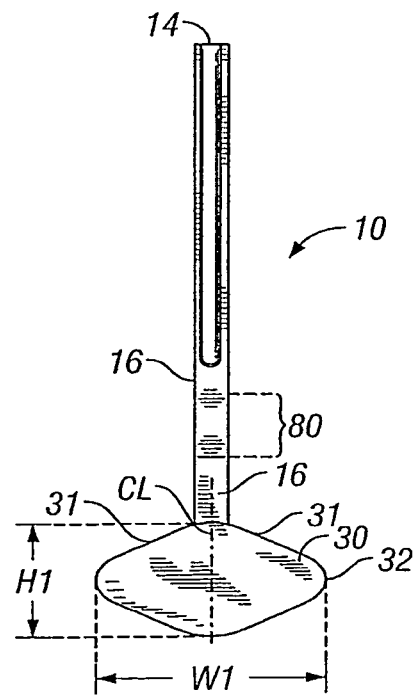

FIG. 11B depicts a frontal view of the hanger of FIG. 11A. As is visible in that figure, the plate 30 includes is essentially flat and planar, and excludes any perforations passing therethrough as well as excluding any outwardly extending from either the front face 37 or the rear face 37' of the plate 30.

Figure 11C:
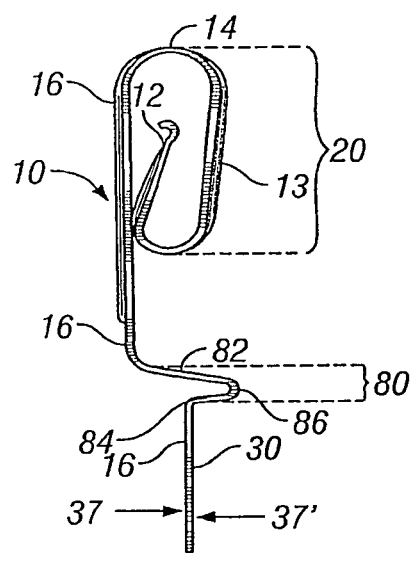

FIG. 11C depicts a side view of the hanger 10 of prior FIGS. 11A and 11B. As is more evident from the figure, the standoff section 80 extends in the same direction as that of the hook end 20, and particularly at least the top element 14 which extends rearwardly from the stalk 16. As may be also understood from the figure, in preferred embodiments the hook end 20 and the standoff section 80 are preferably coplanar with respect to one another, while the plate 30 is preferably approximately perpendicular to this plane within which the hook end 20 and the standoff section 80 are coincident. Also more clearly visible is the absence any outwardly extending from either the front face 37 or the rear face 37' of the plate 30.

Figure 11D:
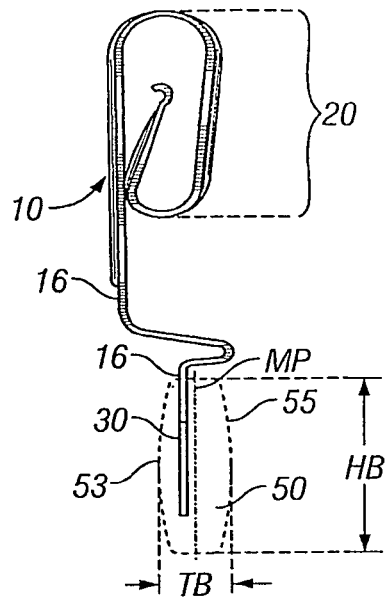

FIG. 11D is a further illustration of the hanger 10 of FIG. 11C however the figure further illustrates a compressed solid block 50 encasing the hanger 30 and here, also part of the stalk 16 immediately adjacent to the plate 30. The said block 50 is depicted in phantom for sake of convenient review of the features of the hanger 10. The compressed solid block 50 has a thickness "TB" as well as a height "HB". FIG. 11D illustrates a preferred embodiment of the invention, namely wherein the plate 30 is positioned on the interior of the block 50 and is in a plane parallel to the mid-plane "MP" which bisects the block 50 and particularly is between the mid-plane MP and the front face 53 of the block 50. The front face 53 of the block 50 is the face which faces the interior of a sanitary appliance, here the interior of a toilet bowl WC, while the back face 55 is intended to be positioned adjacent to or abutting the interior sidewall SW of a sanitary appliance, particularly that of a toilet bowl WC.

Figure 11E:
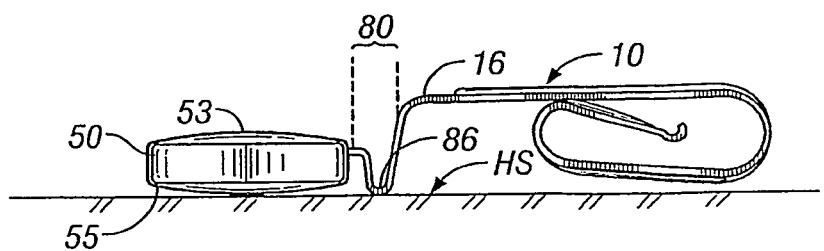

FIG. 11E depicts the embodiment depicted on FIG. 11D, however illustrates the compressed solid block 50 in solid lines. The depiction illustrates that in accordance with particularly preferred embodiments, when the device is laid upon a flat horizontal surface "HS", the standoff element 80 has a sufficient height such that the peak point 86 is sufficiently extended to raise at least a part of the rearward face 55 of the compressed solid block 50 from contacting the horizontal surface. In this figure, none of the compressed solid block 50 is in contact with the horizontal surface HS.

Figure 11F:
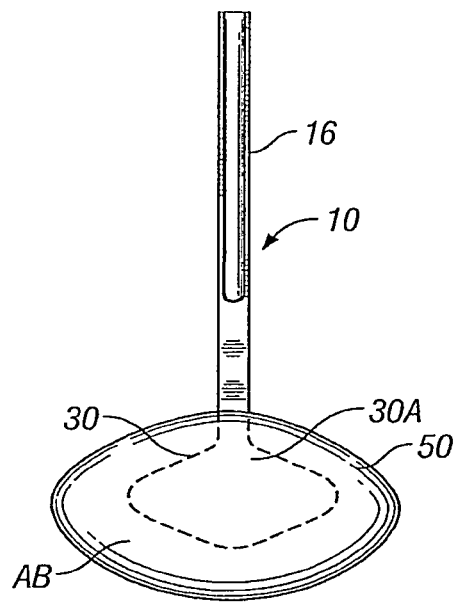

FIG. 11F illustrates a frontal view of the embodiment depicted on FIGS. 11D and 11E. For sake of convenience, the plate 30 embedded within the solid compressed block 50 is depicted in phantom. As is illustrated in the figure, the respective areas of the plate 30A and the area AB of the block 50 at the transverse plane coincident with a face of the plate 30A, further illustrating a preferred ratio of these two surface areas.

Figure 11G:
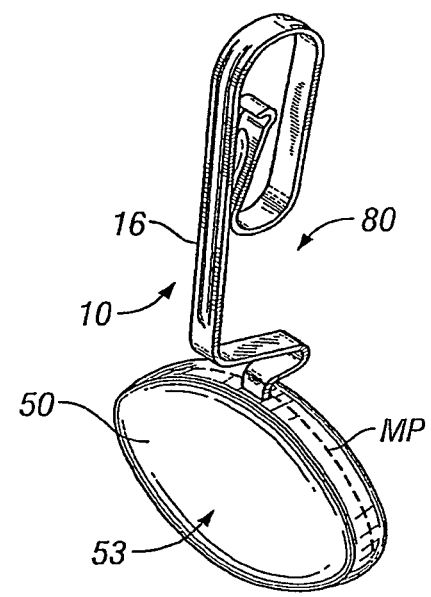

FIG. 11G illustrates a top and side perspective view of the lavatory dispensing device 80 of prior FIGS. 11D, 11E and 11F illustrating the relationship of the placement of the plate 30 within the block 50. More specifically the plane of the plate 30 is between the mid-plane MP and the front face 53 of the block 50. The embodiment of the lavatory dispensing device 80 illustrates a preferred embodiment of the invention.

Figure 12A:
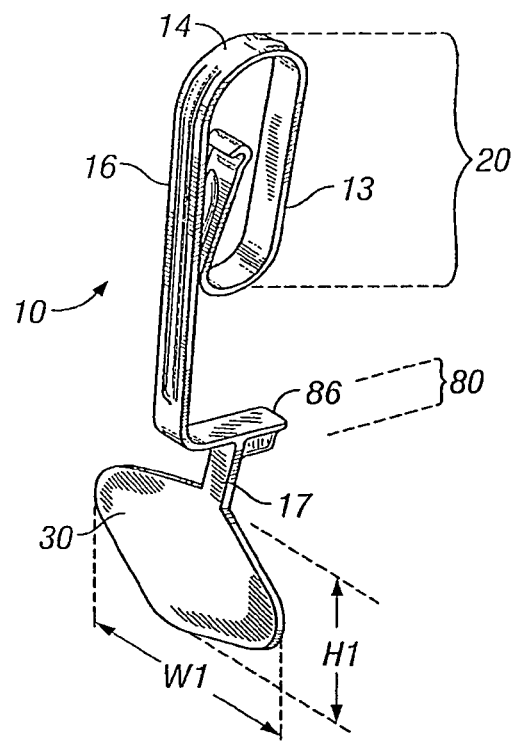
FIG. 12A and FIG. 12B depict a still further embodiment of a hanger according to the invention which comprises a standoff section.
Figure 12B:
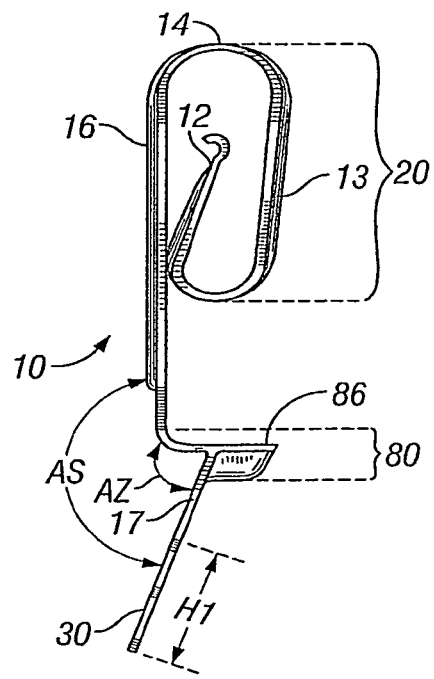

FIGS. 12A and 12B depicts a still further embodiment of a hanger 10 according to the invention which comprises a standoff section 80. As is shown, the hanger includes a hook end 20 which is comprised of the end member 12, flexibly connected to an intermediate element 13, which is in turn flexibly connected to a top element 14, which in turn is flexibly connected to a part of the stalk 16. The opposite end of the stalk terminates in a generally oblate (or "diamond") shaped plate 30 having a width dimension (W1), a height dimension (H1). Whereas the hanger is depicted in a folded or otherwise coiled configuration, it is to be understood that the hook end can be extended by a user of the hanger and the cageless lavatory dispensing device to reconfigure said hook end 20 to form a hook end which can be used to suspend the hanger and the cageless lavatory dispensing device upon a part of a sanitary device particularly a toilet bowl rim. The embodiments according to FIGS. 12A and 12B also illustrate that, according to preferred embodiments, the plate 30 is substantially planar and as is shown in the figures and is of generally uniform thickness. The embodiment of the hook end 20 as depicted in the figures is preferred in that the hook end 20 is particularly well coiled when in its folded configuration, but when uncoiled or in its unfolded configuration, provides a significant degree of tension which is useful in retaining the respective position of the cageless lavatory dispensing device when installed upon a sanitary appliance, particularly when the hook is affixed on a part of a toilet bowl rim. Furthermore, as is visible the stalk 16 extends downwardly and rearwardly such that it bends in the direction of the hook end 20 and defines a first stalk segment 82 which extends rearwardly from the stalk 16 to a peak point 86; said segment 82 defines a standoff section 80. Depending downwardly from the first stalk segment 82 is a bent neck 17 from which depends the plate 30. As depicted, the bent neck 17 forms an angle "AZ" with respect to the stalk 16 and also, forms a second angle "AS" between the face of the plate 30 and the stalk 16.

Desirably, in all embodiments of the invention (and not limited to the embodiment of FIGS. 12A and 12B) wherein the stalk 16 and the plate 30 are angled with respect to one another, as represented by angle AS, angle AS is between 90°-180°, but preferably is between 100° and 170°, and most preferably is between 105° and 145°. Such an angular relationship between the stalk 16 and the plate 30 are relevant to the invention wherein the hanger includes or excludes a standoff section 80. Similarly in all embodiments of the invention wherein the stalk 16 and the bent neck 17 are angled with respect to one another, as represented by angle AS, angle AS is between 0°-90°, but preferably is between 10° and 80°, and most preferably is between 15° and 55°. Such an angular positioning of the plate 30 which ultimately supports the a compressed solid block may be advantageous This positioning rearward of the major part of the stalk 16 is beneficial as ultimately, it acts to also thereby position the compressed solid block enrobing the plate 30 such that when the hanger 10 is mounted upon a toilet bowl, the compressed solid block may be positioned in the proximity to the interior sloping side wall of a toilet bowl but at an angle away therefrom. Such positioning is advantageous in that it ensures that the compressed solid block remains in the flow path of the flush water throughout the useful service life of the cageless lavatory dispensing device, but minimizes the likelihood of physical contact of the compressed solid block and the interior sidewall of a toilet bowl.

FIGS. 13A through 13D depict various alternate configurations which may also be used for the plate 30 for the hanger as described herein. FIG. 13A depicts a diamond-shaped plate 30 depending at one vertex from the stalk 16. FIG. 13B depicts a substantially circular plate 30 depending from one part of its circumference from the stalk 16. FIG. 13C depicts an equilateral-triangular shaped plate 30 depending at one vertex from the stalk 16. FIG. 13D depicts a further plate 30 which is generally rectangular but having two opposite semi-circular ends depending from the stalk 16. In each of the foregoing, it is seen that the configuration of the plates is generally symmetrical about the center line, CL.

FIG. 14 depicts an embodiment of a portion of the hanger wherein the plate 30 includes a series of perforations 33 passing therethrough. As is depicted, the perforations are not symmetrical with respect to either the center line CL or the configuration of the semi-circular shaped plate 30. As noted above, plates 30 having perforations passing there through are less preferred embodiments of the hangers and useful with the lavatory dispensing devices taught herein.

FIGS. 15A and 15B depict in two views an embodiment of a plate 30 depending from a stalk 16 wherein the plate comprises at least one, here a plurality of projections 35 extending outwardly from the generally planar and opposite faces 37, 37' of the plate. As is seen in particular in FIG. 15B, the projections 35 are in the form of generally cylindrical studs having a base coincident with the respective face 37, 37' of the plate 30. The studs terminate at flat ends, by may have different configurations, i.e., semicircular, conical or frustoconical. The studs, when present, advantageously have a height which is approximately equal to, or slightly greater than thickness of the plate 30. The studs 33 may extend outwardly from one, or both sides of the plate 30 the latter embodiment being illustrated on FIG. 15B. Again, while these figures depict the utility of outwardly extending elements extending outward from the plate, again, as noted above embodiments of the hanger having such outwardly extending elements from the plate are less preferred.

FIGS. 16A and 16B depict a hanger 10 including an embodiment of an air treatment dispenser 60. As is visible by inspection thereof the hanger 10 is similar in many respects to that described with reference to FIGS. 12A and 12B and are distinguishable thereover by the addition of the air treatment dispenser 60 which is shown generally depending from the stalk 16. The air treatment dispenser 60 illustrated is adapted to contain a quantity of an air treatment composition (not shown) in a cavity 62 which is defined by a sidewall 64 extending outwardly/upwardly from a bottom 65. The sidewall 64 depicted defines a fanciful "C" shaped cavity but any other shape might also be used. The cavity 62 further includes a series of upstanding tapered pins 66 which extend from the bottom 65 and are present in the interior of the cavity 62; the presence of such pins 66, while optional, provides a useful support for a gel type air treatment composition, or a solid air treatment composition, such as is the gel system described in U.S. Pat. No. 5,780,527. As is also evident, the cavity 62 is positioned such that it is adapted to be facing the interior of a toilet bowl or other sanitary appliance upon which the hanger 10 may be mounted, thus the contents of the cavity 62 provide a release of the air treatment composition in the direction of the interior of a toilet bowl or other sanitary appliance.

FIG. 16B illustrates a side view of the hanger 10 depicting the arrangement of the air treatment dispenser 60 with respect to the stalk 16 of the hanger 10. While not illustrated it is understood that the air treatment dispenser 60 is either integrally formed with the hanger 10 or is permanently affixed thereto such as by means of an adhesive or welding of portions of the air treatment dispenser 60 with the stalk 16.

While not illustrated, it is to be understood that the air treatment dispenser 60 may be repositioned with respect to the hanger 10. In one alternative the orientation of the air treatment dispenser 60 is reversed such that the cavity 62 faces the stalk 16 and the cavity faces the hook end 20. In a further alternative the air treatment dispenser 60 may be affixed to or suspended from the end member 12; in such a position the air treatment dispenser 60 is adapted to be exterior of the toilet bowl or sanitary appliance upon which the hanger 10 is mounted and emanates the fragrance or other air treatment composition to ambient environment exterior of the toilet bowl or other lavatory appliance.

FIG. 17 depicts a further hanger 10 including an embodiment of an air treatment dispenser 70. As is visible by inspection thereof the hanger 10 is similar in many respects to that described with reference to FIGS. 12A and 12B but are distinguishable thereover by the addition of the air treatment dispenser 70 which is shown generally depending from the stalk 16. The air treatment dispenser 70 is a housing which is adapted to contain a quantity of an air treatment composition, e.g., a fragrance, or other volatile material which may exit the interior of the air treatment dispenser 70 via the passages 72 present. As is understood from the figure, the passages 72 of the air treatment dispenser 70 are positioned such that they are adapted to face the interior of a toilet bowl or other sanitary appliance upon which the hanger 10 may be mounted, thus the air treatment dispenser 70 provide a release of the air treatment composition in the direction of the interior of a toilet bowl or other sanitary appliance.

While not illustrated, it is to be understood that the air treatment dispenser 70 may be repositioned with respect to the hanger 10. In one alternative the orientation of the air treatment dispenser 70 is reversed such that the passages 72 face the stalk 16 and the hook end 20. In a further alternative the air treatment dispenser 70 may be affixed to or suspended from the end member 12; in such a position the air treatment dispenser 70 is adapted to be exterior of the toilet bowl or sanitary appliance upon which the hanger 10 is mounted and emanates the fragrance or other air treatment composition to ambient environment exterior of the toilet bowl or other lavatory appliance.

In certain preferred embodiments the air treatment dispenser 70 may be replaceable upon the hanger 10 or may contain a refill cartridge (not shown) or other refill element which may be used to resupply the air treatment dispenser 70 with a further quantity of an air treatment composition, e.g., a fragrance when necessary, such as upon the prior exhaustion of a prior refill cartridge or air treatment dispenser 70.

Figure 18B:
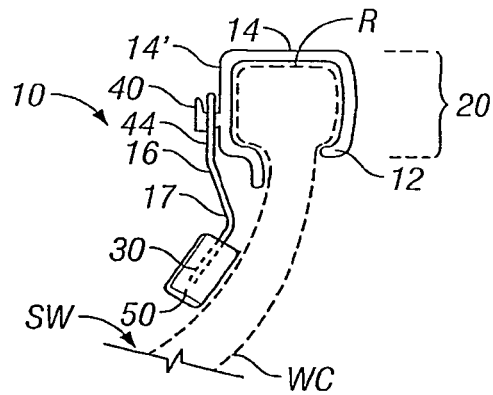
FIGS. 18A and 18B depicts two views of an embodiment of a two-part cageless lavatory dispensing device.
Figure 18A:
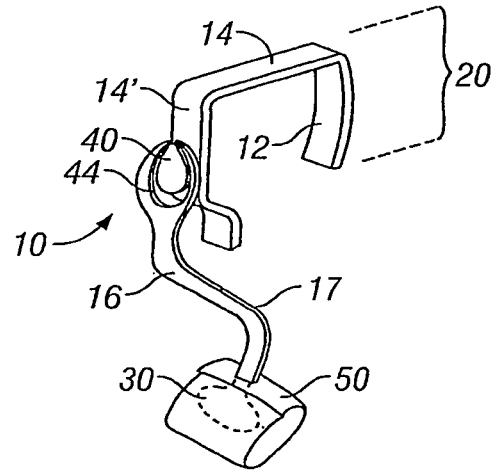

FIGS. 18A and 18B depict two views of an embodiment of a two-part cageless lavatory dispensing device 10 of the invention. FIG. 18A depicts a perspective view of a hook end 20 comprising an end member 12, a top element 14 and a front element 14' having extending from a part thereof a hanger peg 40. The hook end 20 is configured to be suspended upon the rim of a toilet bowl "WC" and may be used a single time but desirably is used several times by a consumer. The second part of the cageless lavatory dispensing device of the invention 10 includes a stalk 16 having at a proximal end an eyelet or loop 44 which is sufficiently sized so that the stalk 16 may be removably affixed to and suspended from the hanger peg 40. The stalk 16 extends downwardly from the proximal end to the distal end and includes a slanting neck 17, which terminates in plate 30 which is encased in a compressed solid block 50. This second part may be installed by a user, and when the compressed solid block 50 is consumed, this second part may be removed by the consumer and replaced with a further second part with a new compressed solid block 50 and utilized.

As is more clearly depicted on FIG. 18B, the hook end 20 is mounted upon a part of a rim "R" of a toilet bowl "WC". The second part is suspended by eyelet 44 such that the compressed solid block 50 is positioned adjacent to or upon the inner sidewall "SW" of the toilet bowl WC. In this manner, flush water released from the rim downwardly into the toilet bowl WC contacts the compressed solid block 50 to form a treatment composition which is used to treat the toilet bowl.

While a cooperating hanger peg 40 and eyelet 44 exemplified one embodiment of a useful fastener means which may be used to assemble a cageless lavatory dispensing device 10 within the meaning of the invention, it is contemplated that any other effective fastener means or cooperative fastener elements as discussed above, particularly mechanical means and/or chemical means may be used as well and is considered to be within the scope of the invention, although not specifically depicted in the figures. It is also contemplated that the dispensing devices 10 may also further include an air treatment dispenser which may be advantageously present on the stalk 16 and/or on the top element 14 or end element 12.

Figure 19:
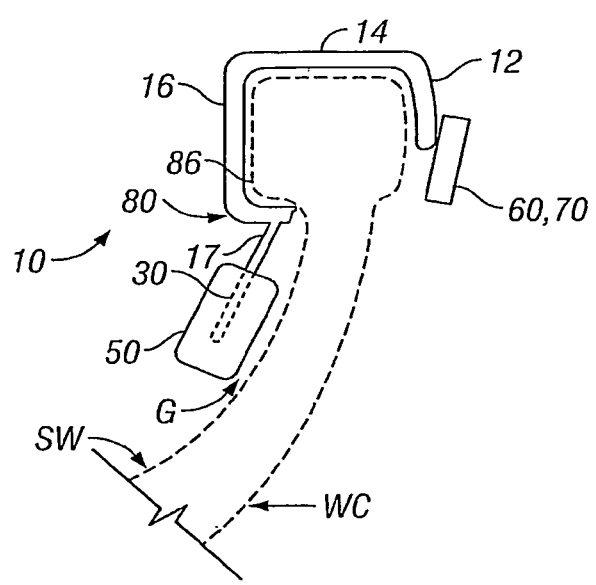
FIG. 19 illustrates an embodiment of a hanger mounted on a part of a toilet bowl.

FIG. 19 depicts an embodiment of a dispensing device 10 of the invention which includes a standoff section 80 configured for use as an ITB device, illustrating the device 10 mounted on the rim "R" of a toilet bowl "WC". As seen in the figure a hook end 20 comprising an end element 12, and a top element 14 are configured to be suspended upon the rim of a toilet bowl "WC". The hanger 10 includes a stalk 16 which extends downwardly and includes an integrally formed standoff section 80 comprising parts of the stalk 16 adjacent to the peak point 86, which stalk 16 continues to extend downwardly and terminates via a bent neck section 17 at plate 30 which is encased in a compressed solid block 50. As is seen from the figure, the dimensions of the hanger 10 are such that when it is installed in a toilet bowl, the peak point 86 contacts a part of the inner sidewall "SW" of the toilet bowl and lifts the block 50 from physical contact with said inner sidewall SW defining an intermediate gap "G". In this manner, flush water released from the rim downwardly into the toilet bowl WC contacts the compressed solid block 50 to form a treatment composition which is used to treat the toilet bowl. Part of the flush water also flows in the gap G wherein it flushes the rear face of the block 50 as well. Subsequent to the flush cycle, the block 50 rests out of contact with the sidewall SW and above the remaining water present in the toilet bowl WC thus providing an opportunity for the block to dry between flushes.

The figure further illustrates the position of an air treatment dispenser 60, 70 which is provided. As is seen, the air treatment dispenser 60, 70 is mounted via the hanger 10 on the exterior of the toilet bowl WC so to supply an air treatment benefit which is directed to the exterior ambient environment of the toilet bowl WC. Such may be beneficial to provide an air treatment benefit when the interior of the toilet bowl is covered between uses, such as by a toilet seat and/or toilet set cover. It is to be understood that while not depicted, that the air treatment dispenser 60, 70 may be mounted via the hanger 10 such that it is directed towards the interior of the toilet bowl WC so to supply an air treatment benefit which is directed to the interior ambient environment of the toilet bowl WC. For instance, the air treatment dispenser 60, 70 may be mounted on a further part of the hanger 10 such as upon the stalk 16 or bent neck 17 using suitable means. Such a configuration may be beneficial in order to provide an air treatment benefit to the interior of the toilet bowl especially when it is covered between uses, such as by a toilet seat and/or toilet set cover. In any case, the provision of an air treatment dispenser 60, 70 as illustrated and/or as described immediately above may be omitted from any embodiment of the hanger 10, particularly if no air treatment benefit is required or desired, or wherein the composition of the compressed block contains a fragrance or other constituent which may provide an air treatment benefit.

While the hanger depicted in FIG. 19 is similar to the hanger disclosed and discussed with reference to FIGS. 12A and 12B, such is to be understood by way of illustration and not by way of limitation and other hangers according to the invention, and advantageously those which comprise a standoff section may be suspended in a lavatory appliance and used in a similar manner although not specifically depicted in the figures.

Figure 20A:
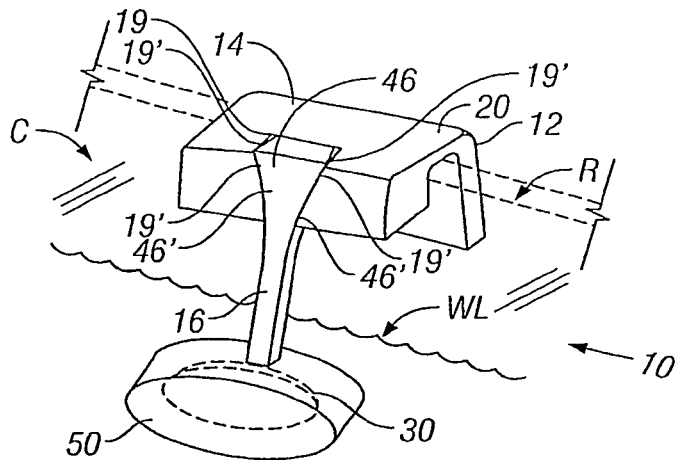
FIGS. 20A and 20B depicts a further embodiment of a two-part hanger configured for use as an ITC device.
Figure 20B:
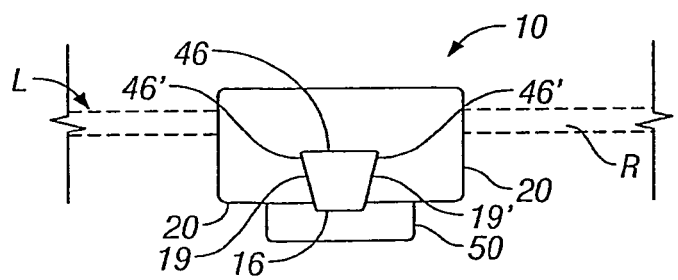

FIGS. 20A and 20B depict two views of an embodiment of a two-part cageless lavatory dispensing device 10 of the invention configured for use as an ITC device.

FIG. 20A depicts a perspective view of a two-part cageless lavatory dispensing device 10 comprising a first part, a rigid hook end 20 adapted to be suspended upon the rim "R" of a toilet cistern "C", and a second part, a stalk 16 having a sloped, tenon-shaped proximal end 46 inserted in a suitably shaped mortise 19 present in the hook end 20, and at its distal end a plate 30 encased by a compressed solid block 50. The stalk 16 is of sufficient length that between flushes of the toilet to which it is attached, the block 50 is submerged beneath the water line "WL" so that the water contacts the block 50 to form a treatment composition within the cistern C. As is more clearly visible from FIG. 20B, the mortise 19 includes two sloped mortise sidewalls 19' which abut correspondingly shaped tenon sidewalls 46' of the proximal end 46 of the stalk 16. Further, as is more apparent from FIG. 11A the tenon sidewalls 46' of the proximal end 46 of the stalk 16 are seen to taper inwardly toward one another as well, as well as the two sloped mortise sidewalls 19' which are configured to correspondingly conform.

Figure 21A:
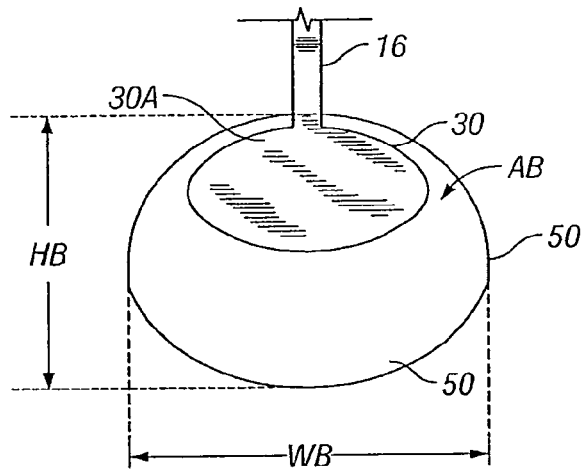
FIGS. 21A through 21C illustrates a potion of a hanger with a compressed solid block composition affixed to the plate.
Figure 21B:
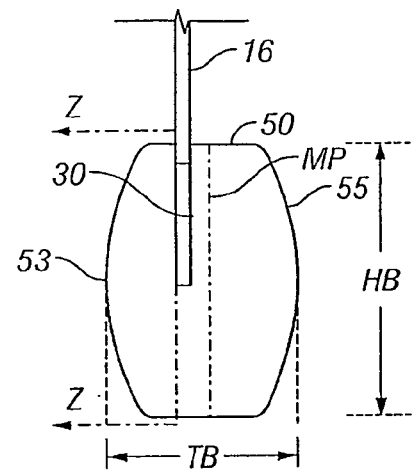
Figure 21C:
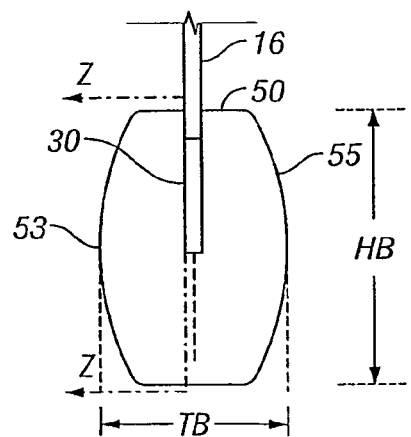

FIGS. 21A, 21B and 21C depict respectively a front sectional view of a compressed solid block 50 encasing/enrobing a plate 30 which depends from a stalk 16, while the latter two figures depict alternate side views of the foregoing. As is depicted on FIGS. 21B and 21C, there is depicted a compressed solid block 50 encasing the plate 30 as well as the stalk 16 extending outwardly from the compressed solid block. The compressed solid block has a thickness "TB" as well as a height "HB".

FIG. 21B illustrates one preferred embodiment of the invention, namely wherein the plate 30 is positioned on the interior of the block 50 and is in a plane parallel to the mid-plane "MP" which bisects the block 50 and is between the mid-plane MP and the front face 53 of the block 50. The front face 53 of the block 50 is the face which faces the interior of a sanitary appliance, here the interior of a toilet bowl WC, while the back face 55 is intended to be positioned adjacent to or abutting the interior sidewall SW of the toilet bowl WC. Further depicted on FIG. 21B is a sectional line "ZZ" which is intended to indicate a cross section of the block 50 coincident with a face of the plate 30. As can be understood with reference to the figure, the cross sectional area of the base has dimension 30A, which is less than about half of the surface area AB of the section of the compressed solid block 50 which is coincident with the face of the plate 30. More accurately, it should be understood that the calculation of respective ratios of the plate area, 30A to the cross sectional area of the block, AB, is made with the plate 30 being removed from the compressed solid block so that the area AB is unobscured.

FIG. 21C illustrates a further and more preferred embodiment of the invention similar to FIG. 21B but distinguishable in that the plate 30 is positioned on the interior of the block 50 and is in a plane coincident to the mid-plane "MP" which bisects the block between the front face 53 of the block 50 and the back face 55 of the block 50. The front face 53 of the block 50 is the face which faces the interior of a sanitary appliance, here the interior of a toilet bowl WC, while the back face 55 is intended to be positioned adjacent to or abutting the interior sidewall SW of the toilet bowl WC. Further depicted on FIG. 21B is a sectional line "ZZ" which is intended to indicate a cross section of the block 50 coincident with a face of the plate 30. As can be understood with reference to the figure, the cross sectional area of the base has dimension 30A, which is less than about half of the surface area AB of the section of the compressed solid block 50 which is coincident with the face of the plate 30. More accurately, it should be understood that the calculation of respective ratios of the plate area, 30A to the cross sectional area of the block, AB, is made with the plate 30 being removed from the compressed solid block so that the area AB is unobscured.

Figure 22:
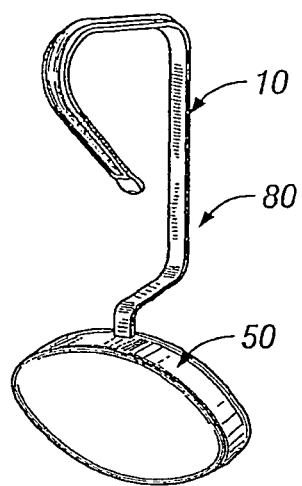
FIG. 22 depicts an embodiment of a hanger of a cageless lavatory device.

FIG. 22 depicts a further embodiment of a lavatory dispensing device 10 according to the invention including hanger 10 as previously described with reference to FIG. 7, a part of which is encased or enrobed in a compressed solid block composition 50.

Figure 23:
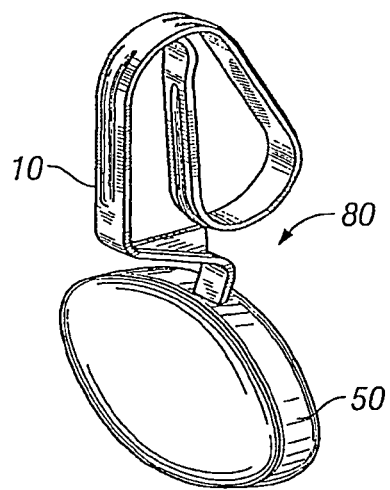
FIG. 23 depicts a further embodiment of a hanger of a cageless lavatory device.

FIG. 23 depicts a yet further embodiment of a lavatory dispensing device 80 according to the invention including hanger 10 as previously described with reference to FIG. 8, a part of which is encased or enrobed in a compressed solid block composition 50.

Figure 24:
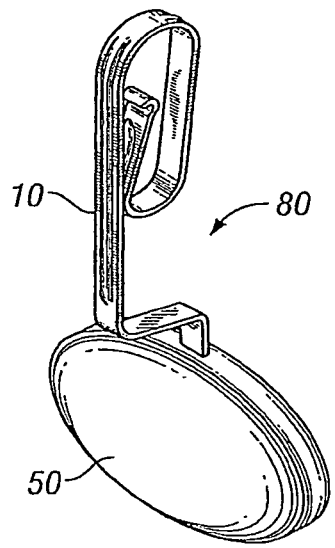
FIG. 24 depicts a further embodiment of a hanger of a cageless lavatory device.

FIG. 24 depicts a further embodiment of a lavatory dispensing device 80 according to the invention including hanger 10 as previously described with reference to FIG. 6, a part of which is encased or enrobed in a compressed solid block composition 50.

Figure 25:
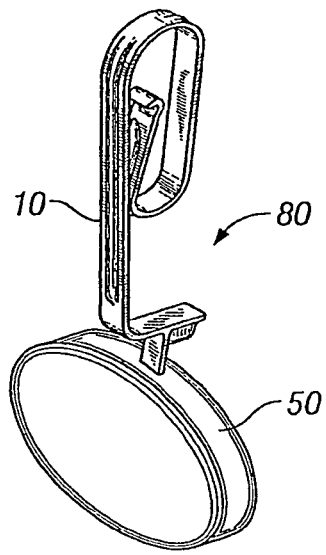
FIG. 25 depicts a further embodiment of a hanger of a cageless lavatory device.

FIG. 25 depicts a yet further embodiment of a lavatory dispensing device 80 according to the invention including hanger 10 as previously described with reference to FIGS. 12A and 12B, a part of which is encased or enrobed in a compressed solid block composition 50.

It is to be understood that a dispensing device according to the invention may also have a different geometry, configuration or and appearance than the embodiments described in the Figures and still be considered to fall within the scope of the invention. It is also to be understood that various elements of the lavatory dispensing devices according to the invention may be interchanged amongst the various embodiments illustrated or described, as may be desirable or necessary.

It is to be understood that cageless the lavatory device according to the invention as well as may be produced by a process according to the invention may also have a different geometry, configuration or and appearance than the embodiments described in the Figures and still be considered to fall within the scope of the invention.

Figure 26:
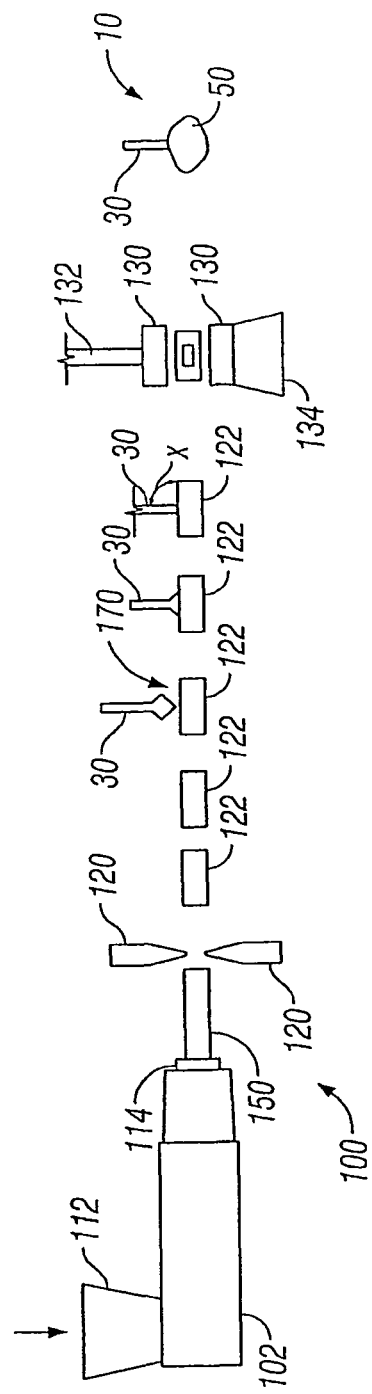
FIG. 26 illustrates a schematic of a series of process steps relating to a process for the manufacture of cageless lavatory devices.

FIG. 26 illustrates a series of process steps which illustrate a preferred embodiment of the improved process for the manufacture of cageless lavatory devices disclosed herein.

With reference to FIG. 26, thereon is depicted by virtue of schematic representations a process 100 for the manufacture of cageless lavatory devices disclosed herein.

Figure 28:
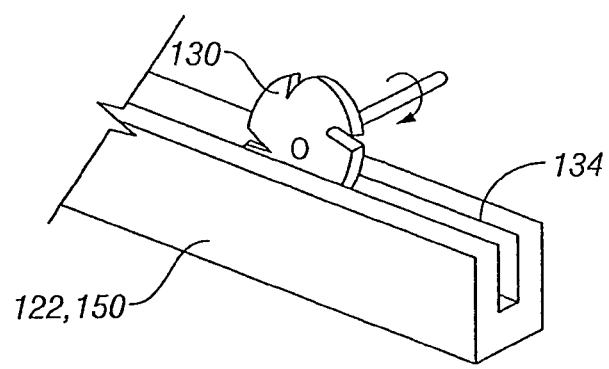
FIG. 28 illustrates a channel cutting means.

In accordance with the process, a premixed block composition or alternately the constituents required to form a block composition is provided to the inlet hopper 112 of an extruder 102. The extruder 102 may be a single screw extruder or a multiple screw extruder. Where plural screws are present, the screws may be co-rotating or may be counter-rotating. If not previously mixed or blended prior to introduction into the extruder, the block composition is formed into a generally homogeneous mass and exits the extruder via a suitable die 114 which has an orifice profile of suitable dimensions. Advantageously the die has a configuration as generally depicted on FIG. 27. After exiting the die 114, measured lengths or measured masses of the extrudate 150 are separated such as by cutting using a cutting blade 120, chain cutter or other suitable device into performs 122 of approximately like dimensions and/or mass.

Wherein the die does not shape the extrudate to include a cavity, channel or recess within the extrudate of suitable dimensions to accept at least the plate of a hanger, an additional process step may be practiced. In one such step, a channel-cutting step as depicted in FIG. 28, a channel cutting means such as a rotating winged cutter 130, saw, plough, blade or other cutting device is applied to or passed through the extrudate 150 or alternately to the preforms 122 in order to split or shape the extrudate 150 or performs 122 adequately to provide a channel 134 or recess suitably sized to later receive a portion of a hanger (not shown). Such a channel or recess advantageously extends longitudinally through the extrudate 150 and/or the perform 122 which facilitates convenient positioning of the plate of the hanger in a next process step.

Figure 29:
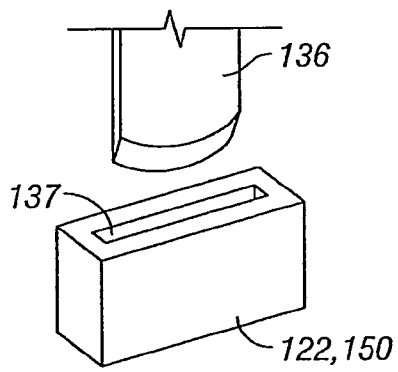
FIG. 29 depicts a perform and a plunging blade.

In an alternate process step, as depicted on FIG. 29, subsequent to extrusion, the extrudate 150 or perform 122 may be provided with a cavity, such as being partially split using an suitable tool means, such as a suitably dimensioned plunging blade 136 which may be used to partially split a portion of an extrudate 150 or a perform 122 in order to provide a cavity 137 or slot which is of sufficient width and depth to subsequently accommodate at least a part of a hanger, especially a plate of a hanger (not shown). Such a cavity 137 formed by such blade need not extend across the length of the preform nor through the ends thereof.

Figure 30:
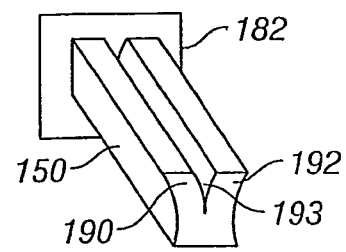
FIG. 30 depicts a partially split extrudate and a die.

Conveniently however, as the extrudate 150 exits the die 114 a channel is provided by extruding through a die which includes a blade or other cutter means which extends into the open cross-section of the die such that as the extrudate exits the die, it is provided with such a channel which partially splits the extrudate into the legs of a "V", which remain attached however at the base of each leg. Such a channel may extend across the length of the preform and through the ends thereof. Alternately, subsequent to extrusion a tool. An exemplary die comprising such a blade is depicted on FIG. 21. Therein is depicted a plan view of a flat die having a die body 182 and a shaped orifice 184 passing therethrough. Extending from one side 186 of the orifice 184 is a cutting member 188, here in the shape of a plough which extends into the interior of the orifice. Advantageously the cutting member 188 ploughs through the extrudate 150 passing through the die orifice 184 to form an extrudate which is partially split into the legs of a "V" such as is illustrated on FIG. 30. As is seen from FIG. 30, the hot extrudate tends to deform slightly and open up the distance between the two legs 190, 192 of the "V"-shaped channel 193 which is advantageous in that it often facilitates the later insertion of a part of a hanger, e.g., a plate prior to the subsequent die compression step of the process.

Returning to FIG. 26, in a next process step, the plate 30 of a hanger is inserted within the interior of the channel 170 or cavity such that the plate is preferably wholly encased within the interior of the preform. Preferably also the hanger 30 extends outwardly from the preform at an angle which is approximately perpendicular to, more specifically 90°±/−10°, preferably 90°±/−5°, with respect to tangent of the surface from which point the hanger extends outwardly therefrom. This angle is indicated in FIG. 26 as "x" for sake of convenient reference. Such ensures that consistent loading and proper weight distribution of the hanger 30, and ultimately the proper placement of the cageless device in the sanitary appliance, especially a toilet is maintained.

Optionally prior to introduction of the preform and hanger into a die in the next process step, the die compression step, one or more of the interior surfaces of the die 130 may be sprayed with a mold release material or other lubricant such as mineral oil or a paraffin oil. The die 130 is preferably a pair of opposing dies 130 which when compressed by a suitable compression means, such as a ram 132 and anvil 134 forms an intermediate die cavity of a suitable dimension within which the preform 122 may be placed. Thus, in the die compression step a preform 122 having an inserted hanger is introduced between the opposing dies 130 and the opposing dies 130 are brought together to both form the compressed solid block composition and adhere it to the plate 30, as well as to densify the composition of the compressed solid block by at least 1.5%, preferably at least 2% more than the density of the extrudate from which the compressed solid block 50 is formed. Advantageously the pressure of the die is 500-1500 psi.

The formed cageless lavatory device 10 is subsequently removed from the die and is ready for use, or alternately may be packaged in a suitable package in order to form a vendible article.

In order to further illustrate the present invention, various examples of preferred embodiments of the invention are described, following. In these examples, as well as throughout the balance of this specification and claims, all parts and percentages are by weight unless otherwise indicated.

EXAMPLES

Compressed solid blocks according to the invention were produced from the described on the following tables; examples according to the invention are indicated by a letter "E" preceding one or more digits. The compositions recited on Table 1 illustrated non-bleach containing compositions according to the invention.

TABLE 1

|  | E1 | E2 | E3 | E4 | E5 | E6 | E7 | E8 |
|---|---|---|---|---|---|---|---|---|
| sodium dodecyl benzene sulfonate (85%) | 35 | 35 | 35 | 35 | 23 | 23 | 27 | 29.2 |
| $C_{14}/C_{16}$ olefin sulfonate, sodium salt (80%) | 22 | 22 | 22 | 32 | 26.4 | 26.4 | 25 | 25.6 |
| sodium lauryl ether sulfate (80%) | — | — | — | 5 | — | — | — | — |
| anhydrous sodium sulfate | 19.9 | 20.9 | 22.91 | 21 | 41.9 | 42.02 | 39.92 | 37.7 |
| lauryl monoenthanolamide | 15 | 15 | 15 | 5 | — | — | — | — |
| anhydrous silica | 2 | 2 | 2 | 2 | 2 | 2 | 2 | — |
| fragrance | 3 | 3 | — | — | 4 | 4 | 4 | 6.298 |
| colorant | 0.1 | 0.1 | — | — | 0.20 | 0.08 | 0.08 | 0.002 |
| mineral oil | 3 | 2 | 3.09 | — | 2.5 | 2.5 | 2 | 1.2 |

TABLE 1-continued

|  | E9 | E10 | E11 | E12 | E13 | E14 | E15 | E16 |
|---|---|---|---|---|---|---|---|---|
| sodium dodecyl benzene sulfonate (85%) | 27 | 23 | 23 | 23.5 | 23 | 29 | 23 | 23 |
| $C_{14}/C_{16}$ olefin sulfonate, sodium salt (80%) | 25 | 26.42 | 26.42 | 26.42 | 26.4 | 27 | 26.4 | 26.4 |
| sodium lauryl ether sulfate (80%) | — | — | — | — | — | — | — | — |
| anhydrous sodium sulfate | 39.92 | 42.5 | 42 | 41 | 42 | 35.93 | 41.9 | 42.1 |
| lauryl monoenthanolamide | — | — | — | — | — | — | — | — |
| anhydrous silica | 2 | 2 | 2 | 2 | 1.5 | 2 | 2 | 2 |
| fragrance | 4 | 4 | 4 | 4 | 4 | 4 | 4 | 4 |
| colorant | 0.08 | 0.08 | 0.08 | 0.08 | 0.1 | 0.066 | 0.2 | 0.001 |
| mineral oil | 2 | 2 | 2.5 | 3 | 2.5 | 2.5 | 2.5 | 2.5 |

|  | E17 | E18 | E19 | E20 | E21 | E22 | E23 |
|---|---|---|---|---|---|---|---|
| sodium dodecyl benzene sulfonate (85%) | 23 | 23 | 23 | 23 | 23 | 23 | 23 |
| $C_{14}/C_{16}$ olefin sulfonate, sodium salt (80%) | 26.4 | 26.4 | 26.4 | 26.4 | 26.4 | 26.4 | 26.4 |
| sodium lauryl ether sulfate (80%) | — | — | — | — | — | — | — |
| anhydrous sodium sulfate | 42.1 | 42.1 | 42.1 | 41.96 | 42.03 | 41.47 | 41.98 |
| lauryl monoenthanolamide | — | — | — | — | — | — | — |
| anhydrous silica | 2 | 2 | 2 | 2 | 2 | 2 | 2 |
| fragrance | 4 | 4 | 4 | 4 | 4 | 4 | 4 |
| colorant | 0.0022 | 0.0019 | 0.084 | 0.136 | 0.065 | 0.126 | 0.1155 |
| mineral oil | 2.5 | 2.5 | 2.5 | 2.5 | 2.5 | 3 | 2.5 |

|  | E24 | E25 | E26 | E27 |
|---|---|---|---|---|
| sodium dodecyl benzene sulfonate (85%) | 23 | 23 | 23 | 23 |
| $C_{14}/C_{16}$ olefin sulfonate, sodium salt (80%) | 26.4 | 26.4 | 26.4 | 26.4 |
| sodium lauryl ether sulfate (80%) | — | — | — | — |
| anhydrous sodium sulfate | 42.49 | 42.49 | 42.49 | 41.49 |
| lauryl monoenthanolamide | — | — | — | — |
| anhydrous silica | 2 | 2 | 2 | 2 |
| titanium dioxide | 0.1 | 0.1 | 0.1 | 0.1 |
| fragrance | 4.5[1] | 4.5[2] | 4.5[3] | 4.5[4] |
| colorant | 0.0022 | 0.0019 | 0.084 | 0.136 |
| mineral oil or paraffin oil | 1.5 | 1.5 | 1.5 | 1.5 |

The identity of the constituents used to form the forgoing compressed solid blocks are identified more specifically on the following Table 2. The individual constituents were used "as supplied" from their respective suppliers and may constitute less than 100% wt, or 100% wt. of the named compound, as indicated on Table 1. If less than 100%, the amount of actives present in the "as supplied" material are indicated in Table 1 and 2.

TABLE 2

| | |
|---|---|
| sodium dodecyl benzene sulfonate (85%) | sodium dodecyl benzene sulfonate (85% wt. actives), supplied as UFARYL DL85 |
| $C_{14}/C_{16}$ olefin sulfonate, sodium salt (80%) | $C_{14}/C_{16}$ olefin sulfonate, sodium salt (80% wt. actives), supplied as Nansa LSS 480/H, or other source |
| sodium lauryl ether sulfate (80%) | sodium lauryl ether sulfate (80% wt. actives), supplied as EMPICOL ESB 70 |
| anhydrous sodium sulfate | anhydrous sodium sulfate |
| lauryl monoethanolamide | lauryl monoethanolamide, supplied as COMPERLAN WB, or other source |
| anhydrous silica | supplied as MICROSIL ED, or other source |
| titanium dioxide | titanium dioxide, powder |
| fragrance | proprietary composition of its respective supplier; (specific fragrances in E24, E25, E26 and E27 included:<br>(1) a lavender fragrance composition;<br>(2) a citrus fragrance composition;<br>(3) a pine fragrance composition;<br>(4) a 'marine' fragrance composition) |
| colorant | proprietary composition of its respective supplier |
| mineral oil | technical grade mineral oil and/or technical grade paraffin oil |

Certain of the foregoing example compositions were subjected to service life testing to evaluate compressed solid block compositions used as ITB cageless lavatory dispensing devices. In accordance with the tests, ITB cageless lavatory dispensing device were produced in accordance with the foregoing discussion in the specification wherein a mass of the compressed solid block compositions were extruded into a preform, a slot was provided in the preform, and a hanger generally in accordance with that illustrated in FIG. 7 was provided such that the plate of the hanger was fully inserted into the slot of the preform. The preform was then subjected to a single compression operation in a suitable die to compress and form the compressed solid block composition into a block having a configuration also generally as depicted on FIG. 22. The initial mass of the compressed solid block composition varied slightly from sample to sample, but initial mass is indicated on the following table.

In accordance with the test samples ITB cageless lavatory dispensing devices were supplied to a toilet, either to a "Remo" model toilet bowl, (ex. Shires Co., Ireland), or an "Alto" model toilet bowl (ex. Ideal Standard Co, UK). The placement of the ITB device varied but once positioned prior to the test was not moved until the test was concluded. The test was performed over a number of successive days, and all testing was performed at approximately room temperature (19-22° C.). Each of the toilets were periodically and automatically flushed by a machine-controlled device which operated the toilets to flush 12 times daily at intervals of 60 minutes between flushes. The appearance of the compressed solid blocks during the duration of the test were observed, and prior to each new day's testing and the initial flush of the day's tests each of the ITB cageless lavatory dispensing devices were removed, weighed, and then replaced in their prior position suspended from the rim of a toilet bowl. In this manner, the loss of the mass of generally dry compressed solid blocks were evaluated at regular intervals. In the following test, four sample devices including a compressed solid block composition according to E3, as well as four sample devices including a compressed solid block composition according to E4 were tested. The results of the test are indicated on the following Table 3.

TABLE 3

| Sample #/ composition | Initial mass of compressed solid block (grams) | % mass loss of compressed solid block following 159 flushes | % mass loss of compressed solid block following 205 flushes | % mass loss of compressed solid block following 253 flushes |
|---|---|---|---|---|
| 1/E4 | 112.3 | 26.19 | 36.82 | 82.14 |
| 2/E4 | 104.9 | 4.69 | 7.05 | 47.49 |
| 3/E4 | 106.2 | 28.96 | 38.11 | 85.95 |
| 4/E4 | 110 | 4.44 | 6.50 | 44.45 |
| 5/E3 | 98.9 | 1.62 | 4.16 | 49.73 |
| 6/E3 | 109.5 | 10.90 | 18.53 | 60.76 |
| 7/E3 | 107.2 | 3.97 | 9.29 | 55.80 |
| 8/E3 | 100.8 | 13.98 | 20.25 | 65.80 |

During the test and following the conclusion of the test, no breaking off of the compressed solid block compositions were observed, demonstrating surprisingly effective adhesion of the compositions to the plate notwithstanding multiple flush cycles wherein flowing water delivered from the rim of the toilet impinging directly on the plate and the respective compositions. The compositions also delivered an effective amount of the surfactants present in the blocks as evidenced by the formation of bubbles or foam at the waterline of the toilet bowl following a flush cycle.

The disparities in the rate of dissolution of the tested sample devices at like numbers of flushes may often attributed to the placement of the sample with respect to specific positions on the rim of the toilet bowl, as in some positions greater volumes of water were released with each flush and tended to erode or dissolve the compressed block composition more quickly than at other positions. Such is not considered to be a detriment, but rather permits the consumer to selectively place the ITB cageless lavatory dispensing devices to provide a degree of control over the useful life of the block, and upon the degree of foaming which is desired following individual flushes of the toilet bowl.

Additional sample ITB cageless lavatory dispensing devices based on compressed block compositions according to further examples described on Table 1 were also subjected to testing generally according to the procedure outlined above. In accordance with the test, samples were supplied to an "Alto" model toilet bowl (ex. Ideal Standard Co, UK). The placement of the ITB device varied but once positioned prior to the test was not moved until the test was concluded. The test was performed over a number of successive days, and all testing was performed at approximately room temperature (19-22° C.). Each of the toilets were periodically and automatically flushed by a machine-controlled device which operated the toilets to flush 16 times during each day of testing at intervals of approximately 60 minutes between flushes. The appearance of the compressed solid blocks during the duration of the test were observed, and prior to each new day's of testing and the initial flush of the day's tests each of the ITB cageless lavatory dispensing devices were removed, weighed, and then replaced in their prior position suspended from the rim of a toilet bowl. In this manner, the loss of the mass of generally dry compressed solid blocks were evaluated at regular intervals. The results of the test are outlined on the following Table 4. Multiple replicate samples of each cageless lavatory dispensing device of respective compressed lavatory block compositions were produced and individually tested.

TABLE 4

| Sample #/ composition | Initial mass of compressed solid block (grams) | % mass loss of compressed solid block following 195 flushes | % mass loss of compressed solid block following 338 flushes | % mass loss of compressed solid block following 354 flushes |
|---|---|---|---|---|
| 1/E9 | 34.87 | — | 48.9 | — |
| 2/E9 | 38.62 | — | 46.22 | — |
| 3/E9 | 40.83 | — | 70.78 | — |
| 4/E9 | 39.11 | — | 65.53 | — |
| 5/E9 | 40.81 | — | 69.35 | — |

TABLE 4-continued

| Sample #/composition | | | | |
|---|---|---|---|---|
| 6/E9 | 40.29 | — | 43.93 | — |
| 7/E9 | 39.47 | — | 31.67 | — |
| 8/E9 | 38.82 | 39.09 | — | — |
| 9/E9 | 39.68 | 35.91 | — | — |
| 10/E9 | 35.55 | 63.28 | — | — |

| Sample #/composition | Initial mass of compressed solid block (grams) | % mass loss of compressed solid block following 150 flushes | % mass loss of compressed solid block following 165 flushes |
|---|---|---|---|
| 1/E13 | 65.10 | 25.94 | — |
| 2/E13 | 75.58 | 44.92 | — |
| 3/E13 | 68.90 | 41.34 | — |
| 4/E13 | 64.53 | — | 27.45 |
| 5/E13 | 64.18 | — | 21.14 |
| 6/E13 | 66.58 | — | 29.68 |
| 7/E13 | 66.38 | — | 31.89 |

| Sample #/composition | Initial mass of compressed solid block (grams) | % mass loss of compressed solid block following 172 flushes |
|---|---|---|
| 1/E14 | 64.09 | 21.86 |
| 2/E14 | 66.69 | 5.45 |
| 3/E14 | 62.73 | 21.44 |
| 4/E14 | 68.86 | 14.91 |
| 5/E14 | 63.51 | 10.94 |

Again, perceived disparities in the rate of dissolution of the tested sample devices at like numbers of flushes may often attributed to the placement of the sample with respect to specific positions on the rim of the toilet bowl. Such is not considered to be a detriment, but rather permits the consumer to selectively place the ITB cageless lavatory dispensing devices to provide a degree of control over the useful life of the block, and upon the degree of foaming which is desired following individual flushes of the toilet bowl.

Still further sample ITB cageless lavatory dispensing devices based on compressed block compositions according to further examples described on Table 1 were also subjected to an "accelerated" testing protocol generally according to the procedure outlined above except that the toilets were flushed 40 times per each day of the test. In accordance with the test, samples were supplied to a Brazilian toilet bowl. The test was performed over a number of successive days, and all testing was performed at approximately room temperature (19-22° C.). The placement of the ITB device varied but once positioned prior to the test was not moved until the test was concluded. Each of the toilets were periodically and automatically flushed by a machine-controlled device which operated the toilets to flush 40 times during each day of the test at intervals of 30 minutes between flushes. The appearance of the compressed solid blocks during the duration of the test were observed, and prior to each new day's of testing and the initial flush of the day's tests each of the ITB cageless lavatory dispensing devices were removed, weighed, and then replaced in their prior position suspended from the rim of a toilet bowl. In this manner, the loss of the mass of generally dry compressed solid blocks were evaluated at regular intervals. The results of the test our outlined on the following Table 5.

TABLE 5

| Sample #/composition | Initial mass of compressed solid block (grams) | % mass loss of compressed solid block following 165 flushes |
|---|---|---|
| 1/E20 | 37.89 | 54.84 |
| 2/E20 | 37.07 | 20.9 |
| 3/E20 | 37.53 | 72.92 |
| 4/E20 | 39.88 | 36.83 |
| 5/E20 | 37.84 | 19.47 |
| 6/E21 | 38.07 | 25.48 |
| 7/E21 | 39.39 | 39.42 |
| 8/E21 | 34.47 | 40 |
| 9/E21 | 38.37 | 26.55 |
| 10/E21 | 38.06 | 23.14 |
| 11/E21 | 37.69 | 28.04 |

Yet again, perceived disparities in the rate of dissolution of the tested sample devices at like numbers of flushes may often attributed to the placement of the sample with respect to specific positions on the rim of the toilet bowl, as in some positions greater volumes of water were released with each flush and tended to erode or dissolve the compressed block composition more quickly than at other positions. Such is not considered to be a detriment, but rather permits the consumer to selectively place the ITB cageless lavatory dispensing devices to provide a degree of control over the useful life of the block, and upon the degree of foaming which is desired following individual flushes of the toilet bowl.

Yet further sample ITB cageless lavatory dispensing devices based on compressed block compositions according to further examples described on Table 1 were also subjected to an "accelerated" testing protocol generally according to the procedure outlined above except that the toilets were flushed 40 times per each day of the test. In accordance with the test, samples were supplied to a model "Alto" toilet bowl as described above. The test was performed over a number of successive days, and all testing was performed at approximately room temperature (19-22° C.). Each of the toilets were periodically and automatically flushed by a machine-controlled device which operated the toilets to flush 40 times during each day of the test at intervals of 30 minutes between flushes. The placement of the ITB device varied but once positioned prior to the test was not moved until the test was concluded. The appearance of the compressed solid blocks during the duration of the test were observed, and prior to each new day's of testing and the initial flush of the day's tests each of the ITB cageless lavatory dispensing devices were removed, weighed, and then replaced in their prior position suspended from the rim of a toilet bowl. In this manner, the loss of the mass of generally dry compressed solid blocks were evaluated at regular intervals. The results of the test our outlined on the following Table 6.

TABLE 6

| Sample #/<br>composition | Initial mass<br>of compressed<br>solid block<br>(grams) | % mass loss<br>of compressed<br>solid block<br>following<br>172 flushes |
|---|---|---|
| 1/E22 | 39.54 | 54.29 |
| 2/E22 | 37.79 | 44.40 |
| 3/E22 | 37 | 13.62 |
| 4/E22 | 38.69 | 37.96 |
| 5/E22 | 38.6 | 54.55 |
| 6/E22 | 38.41 | 48.89 |
| 7/E22 | 37.63 | 10.37 |
| 8/E23 | 36.88 | 48.69 |
| 9/E23 | 36.63 | 37.45 |
| 10/E23 | 36.42 | 20.86 |
| 11/E23 | 38.48 | 39.83 |
| 12/E23 | 35.85 | 36.93 |
| 13/E23 | 38.53 | 57.69 |
| 14/E23 | 37.88 | 36.35 |

Yet again, perceived disparities in the rate of dissolution of the tested sample devices at like numbers of flushes may often attributed to the placement of the sample with respect to specific positions on the rim of the toilet bowl, as in some positions greater volumes of water were released with each flush and tended to erode or dissolve the compressed block composition more quickly than at other positions. Such is not considered to be a detriment, but rather permits the consumer to selectively place the ITB cageless lavatory dispensing devices to provide a degree of control over the useful life of the block, and upon the degree of foaming which is desired following individual flushes of the toilet bowl.

Still further samples of foregoing example compositions were subjected to service life testing to evaluate compressed solid block compositions used as ITB cageless lavatory dispensing devices. In accordance with the tests, ITB cageless lavatory dispensing device were produced in accordance with the foregoing discussion in the specification wherein a mass of the compressed solid block compositions were extruded into a preform, a slot was provided in the preform, and a hanger generally in accordance with that illustrated in FIGS. 12A and 12B was provided such that the plate of the hanger was fully inserted into the slot of the preform. The preform was then subjected to a single compression operation in a suitable die to compress and form the compressed solid block composition into a block having a configuration also generally as depicted on FIG. 25. For each indicated composition at least four replicates or samples were produced and tested in the manner outlined. The initial mass of the compressed solid block composition varied slightly from sample to sample, but the average value of the initial mass for each set of replicates as well as the average value of the later mass for each set of replicates of each type of block as measured during the test is indicated on the following Table 7.

Figure 31:
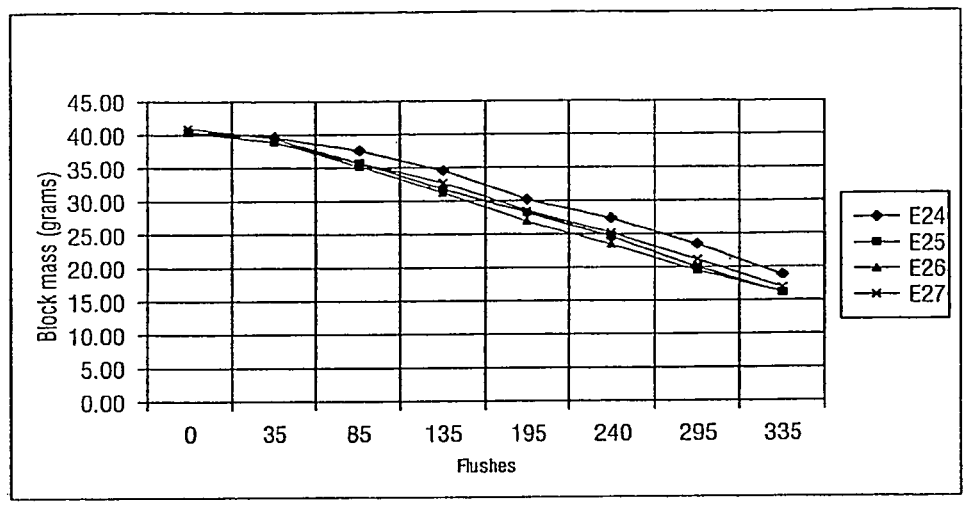
FIGS. 31, 32 and 33 are graphs illustrating the results of flush testing of various embodiments of cageless lavatory devices.
Figure 32:
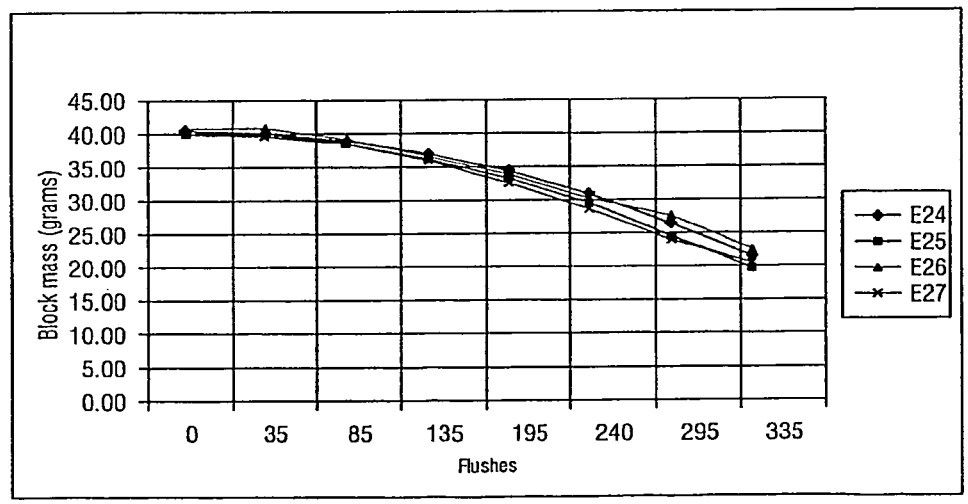
Figure 33:
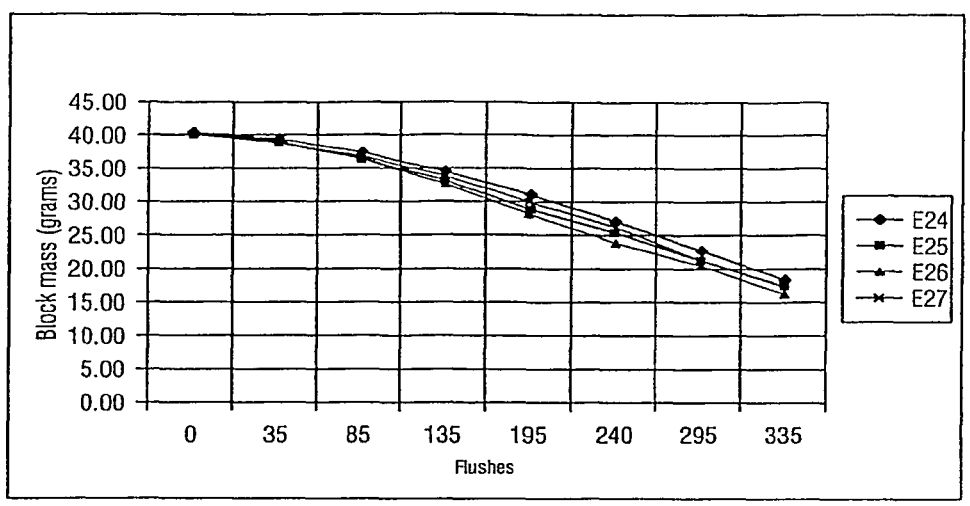

In accordance with the test samples ITB cageless lavatory dispensing devices were supplied to a toilet, either to a "Remo" model toilet bowl, (ex. Shires Co., Ireland), or an "Alto" model toilet bowl (ex. Ideal Standard Co, UK), or a "Jacob Delafon" toilet bowl (ex. Delafon, France). The placement of the ITB device varied but once positioned prior to the test was not moved until the test was concluded. The test was performed over a number of successive days, and all testing was performed at approximately room temperature (19-22° C.). Each of the toilets was periodically and automatically flushed by a machine-controlled device which operated the toilets to flush 12 times daily at intervals of approximately 60 minutes between flushes. The appearance of the compressed solid blocks during the duration of the test were observed, and prior to each new day's testing and the initial flush of the day's tests each of the ITB cageless lavatory dispensing devices were removed, weighed, and then replaced in their prior position suspended from the rim of a toilet bowl. In this manner, the loss of the mass of generally dry compressed solid blocks were evaluated at regular intervals. The results of the test are indicated on the following Table 7 as well as on the accompanying FIGS. 31, 32 and 33.

TABLE 7

| | Total flushes | | | | | | |
|---|---|---|---|---|---|---|---|
| | 0 | 35 | 85 | 135 | 195 | 240 | 295 | 335 |
| Remo toilet; (average) block mass (grams) | | | | | | | |
| E24 | 40.29 | 39.55 | 37.45 | 34.47 | 30.20 | 27.29 | 22.94 | 18.88 |
| E25 | 40.17 | 38.65 | 35.50 | 32.04 | 28.66 | 24.69 | 19.68 | 16.25 |
| E26 | 40.65 | 39.71 | 35.66 | 31.58 | 27.15 | 23.75 | 20.09 | 16.12 |
| E27 | 40.58 | 39.03 | 35.46 | 32.59 | 28.67 | 25.24 | 20.77 | 17.16 |
| Alto toilet; (average) block mass (grams) | | | | | | | |
| E24 | 40.36 | 40.23 | 39.20 | 37.55 | 35.27 | 32.24 | 28.19 | 23.98 |
| E25 | 40.10 | 39.79 | 38.73 | 36.83 | 34.20 | 31.16 | 26.58 | 22.17 |
| E26 | 40.65 | 40.79 | 39.28 | 37.01 | 34.63 | 31.50 | 29.13 | 24.39 |
| E27 | 40.38 | 40.32 | 39.05 | 36.78 | 33.35 | 30.15 | 25.91 | 22.80 |
| Jacob Delafon toilet; (average) block mass (grams) | | | | | | | |
| E24 | 40.36 | 40.23 | 39.20 | 37.55 | 35.27 | 32.24 | 28.19 | 23.98 |
| E25 | 40.10 | 39.79 | 38.73 | 36.83 | 34.20 | 31.16 | 26.58 | 22.17 |
| E26 | 40.65 | 40.79 | 39.28 | 37.01 | 34.63 | 31.50 | 29.13 | 24.39 |
| E27 | 40.38 | 40.32 | 39.05 | 36.78 | 33.55 | 30.15 | 25.91 | 22.80 |

Figure 27:
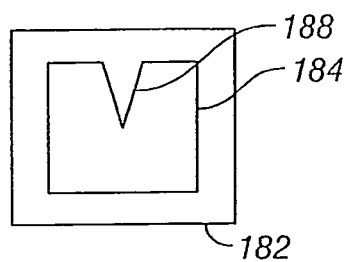
FIG. 27 illustrates a die.

As can be seen from the foregoing the compressed solid block compositions according to E24 through E27 exhibited a good service life and as is evident from the above table as well as the accompanying FIGS. 26, 27 and 28, the block compositions also delivered a satisfactory amount of a surfactant to the toilet bowl during its service life, which provided a cleaning benefit to the toilet bowl with each flush.

It is to be specifically noted that each of the foregoing tested sample ITB cageless lavatory devices exhibited a satisfactory service life and none of the tested samples exhibited breakage or delamination of the compressed solid block composition from the plate of the hanger.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

The invention claimed is:

1. A method for the manufacture of a cageless lavatory dispensing device adapted for the delivery of at least one treatment composition to a sanitary appliance wherein said cageless lavatory dispensing device comprises a hanger having a hook end adapted to be suspended from part of a sanitary appliance, and a compressed solid block comprising at least one chemical agent adapted to be suspended within the interior of the sanitary appliance, wherein the hanger extends outwardly from the compressed solid block, and wherein said method of manufacture comprises the steps of:
   (a) forming a shaped preform from an extruded mass of a composition comprising at least one or more chemical constituents; and,
   (b) compressing the preform to encase at least a portion of the hanger wherein the density of the compressed solid block is at least 1% greater, than the density of the extruded mass.

2. A method according to claim 1 wherein the device comprises a hanger having a hook end, a stalk depending therefrom and a plate depending from the stalk.

3. A method according to claim 1 wherein the device comprises a hanger having a hook end, a stalk depending therefrom which includes a standoff section and a plate depending from the stalk.

4. A method according to claim 2 wherein the compressed solid block composition enrobes or encases part of the hanger.

5. A method according to claim 2 wherein the compressed solid block composition enrobes or encases the plate.

6. A method according to claim 1 wherein the device further includes an air treatment dispenser.

7. A method according to claim 1 wherein the compressed solid block composition comprises one or more chemical constituents such that when the block is immersed, rinsed or washed with water, said chemical constituents are eluted or dissolved into said water and forms a treatment composition which provides a cleaning and/or sanitizing and/or disinfecting benefit to the toilet or other sanitary appliance being treated with the treatment composition.

8. A method according to claim 1 wherein the compressed solid block comprises at least one surfactant.

9. A method according claim 1 wherein the method of manufacture comprises the steps of:
   mixing a chemical composition in an extruder to form the mass;
   extruding a mass;
   forming one or more shaped performs from the extruded mass;
   subsequently placing a portion of the hanger adjacent to at least one perform; and,
   compressing the perform and the portion of the hanger in a die to provide the final form of the compressed solid block composition of the cageless lavatory dispensing device.

10. A method according to claim 9, wherein the process includes the step of:
    compressing the perform shape in a die to provide the final form of the compressed solid block composition of the cageless lavatory dispensing device, which compressed solid block composition enrobes or encases a part of the hanger.

11. A method according to claim 10, wherein the compressed solid block composition is a cleaning composition and/or a sanitizing composition.

12. A method according to claim 10, wherein the cageless lavatory dispensing device comprises a hanger having a hook end adapted to be suspended from the rim of a toilet bowl.

13. A method according to claim 10, wherein the cageless lavatory dispensing device further comprises a coating film or coating layer.

14. A method according claim 1 wherein the method of manufacture comprises the steps of:
    mixing a first chemical composition in an extruder to form a first mass;
    extruding the first mass;
    forming one or more first shaped performs from the extruded first mass;
    providing and mixing a second chemical composition in an extruder to form a second mass;
    extruding the second mass;
    forming one or more second shaped performs from the extruded second mass;
    subsequently placing a portion of the hanger adjacent to and between a first preform formed from the first chemical composition and a second preform formed from the second mass; and,
    subsequently compressing the two performs which surround a portion of the hanger in a die to provide the final form of the compressed solid block composition of the cageless lavatory dispensing device.

15. A method according to claim 14, wherein at least one of the first chemical composition and the second chemical is a cleaning composition and/or a sanitizing composition.

16. A method according to claim 14, wherein the first chemical composition and the second chemical composition are the same.

17. A method according to claim 14, wherein the first chemical composition and the second chemical composition are different.

18. A method according to claim 14, wherein the process includes the step of:
    compressing the shaped preform in a die to provide the final form of the compressed solid block composition of the cageless lavatory dispensing device, which resultant compressed solid block composition enrobes or encases a part of the hanger.

19. A method according to claim 14, wherein the cageless lavatory dispensing device comprises a hanger having a hook end adapted to be suspended from the rim of a toilet bowl.

20. A method according to claim 14, wherein the cageless lavatory dispensing device further comprises a coating film or coating layer.

21. A method according to claim 1, wherein the wherein the density of the compressed solid block is at least 1.5% greater, than the density of the formed mass.

22. A method according to claim 21, wherein the wherein the density of the compressed solid block is at least 2% greater, than the density of the formed mass.

23. A method according to claim 9, wherein the wherein the density of the compressed solid block is at least 1.5% greater, than the density of the extruded mass.

24. A method according to claim 23, wherein the wherein the density of the compressed solid block is at least 2% greater, than the density of the extruded mass.

* * * * *

UNITED STATES PATENT AND TRADEMARK OFFICE
CERTIFICATE OF CORRECTION

PATENT NO. : 8,685,304 B2
APPLICATION NO. : 13/430962
DATED : April 1, 2014
INVENTOR(S) : Nevin Arora et al.

Page 1 of 1

It is certified that error appears in the above-identified patent and that said Letters Patent is hereby corrected as shown below:

On the title page of the patent under the heading Related U.S. Application Data, item [60], "Provisional application No. 60/784,686, filed on March 11, 2006" should read -- Provisional application No. 60/784,686, filed on March 22, 2006 --

Signed and Sealed this
Seventeenth Day of June, 2014

Michelle K. Lee
*Deputy Director of the United States Patent and Trademark Office*